US012735720B2

(12) United States Patent
Long et al.

(10) Patent No.: US 12,735,720 B2
(45) Date of Patent: Sep. 15, 2026

(54) GENE EDITING OF MONOGENIC DISORDERS IN HUMAN HEMATOPOIETIC STEM CELLS—CORRECTION OF X-LINKED HYPER-IGM SYNDROME (XHIM)

(71) Applicant: The Regents of the University of California, Oakland, CA (US)

(72) Inventors: Joseph Long, Studio City, CA (US); Donald B. Kohn, Tarzana, CA (US); Caroline Y. Kuo, Beverly Hills, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 1316 days.

(21) Appl. No.: 17/059,191

(22) PCT Filed: May 30, 2019

(86) PCT No.: PCT/US2019/034713
§ 371 (c)(1),
(2) Date: Nov. 25, 2020

(87) PCT Pub. No.: WO2019/232251
PCT Pub. Date: Dec. 5, 2019

(65) Prior Publication Data

US 2023/0158110 A1 May 25, 2023

Related U.S. Application Data

(60) Provisional application No. 62/760,448, filed on Nov. 13, 2018, provisional application No. 62/678,218, filed on May 30, 2018.

(51) Int. Cl.

| | |
|---|---|
| ***C12N 15/86*** | (2006.01) |
| ***A61K 38/17*** | (2006.01) |
| ***A61K 40/11*** | (2025.01) |
| ***A61K 40/40*** | (2025.01) |
| ***A61K 48/00*** | (2006.01) |
| ***A61P 37/04*** | (2006.01) |
| ***C12N 5/0783*** | (2010.01) |
| ***C12N 9/22*** | (2006.01) |
| ***C12N 15/11*** | (2006.01) |
| ***C12N 15/90*** | (2006.01) |

(52) U.S. Cl.
CPC .......... *C12N 15/86* (2013.01); *A61K 38/1793* (2013.01); *A61K 40/11* (2025.01); *A61K 40/40* (2025.01); *A61K 48/0066* (2013.01); *A61P 37/04* (2018.01); *C12N 5/0636* (2013.01); *C12N 9/22* (2013.01); *C12N 15/11* (2013.01); *C12N 15/907* (2013.01); *C12N 2310/14* (2013.01); *C12N 2310/20* (2017.05); *C12N 2740/15043* (2013.01); *C12N 2750/14143* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 3,106,831 | A | 10/1963 | Behrens |
| 6,106,832 | A | 8/2000 | Spriggs et al. |
| 2016/0208243 | A1 | 7/2016 | Zhang et al. |
| 2017/0101641 | A1 | 4/2017 | Vorechovsky et al. |
| 2017/0121693 | A1 | 5/2017 | Liu et al. |
| 2017/0335011 | A1 | 11/2017 | Conklin et al. |
| 2018/0002719 | A1 | 1/2018 | Roeth et al. |
| 2020/0325458 | A1 | 10/2020 | Rawlings et al. |
| 2021/0324381 | A1* | 10/2021 | Rawlings ............... C12N 15/86 |
| 2021/0379105 | A1 | 12/2021 | Kohn et al. |

FOREIGN PATENT DOCUMENTS

| | | |
|---|---|---|
| GB | 2338237 | 12/1999 |
| WO | WO 2002/077227 | 10/2002 |
| WO | WO-2016182959 A1 | 11/2016 |
| WO | WO-2016186772 A2 | 11/2016 |
| WO | WO-2016201047 A1 | 12/2016 |
| WO | WO-2017053729 A1 | 3/2017 |

(Continued)

OTHER PUBLICATIONS

Genome assembly GRCh37.p13. National Library of Medicine (accessed at: https://www.ncbi.nlm.nih.gov/datasets/genome/GCF_000001405.25/) (Year: 2013).*

(Continued)

*Primary Examiner* — Valerie E Bertoglio
*Assistant Examiner* — Briana N Ebbinghaus
(74) *Attorney, Agent, or Firm* — Mark S. Cohen; PEARL COHEN LLP

(57) ABSTRACT

Described herein are methods of treating X-Linked Hyper-IgM Syndrome (XHIM) in a mammal. Methods include: (i) providing differentiated T cells and/or stem/progenitor cells obtained from the mammal; and (ii) performing a targeted insertion of a corrective CD40L cDNA at the CD40LG gene locus in the differentiated T cells and/or stem/progenitor cells. The targeted insertion provides a corrected CD40LG gene and places the corrective CD40L cDNA downstream and operably linked to the endogenous CD40LG enhancer/promoter. The method further includes (iii) introducing these recombinant cells into the mammal, wherein the corrected CD40LG gene is expressed in a physiologically regulated manner.

5 Claims, 50 Drawing Sheets

Specification includes a Sequence Listing.

(56) References Cited

FOREIGN PATENT DOCUMENTS

WO WO-2017143071 A1 8/2017
WO WO-2018232356 A1 12/2018
WO WO-2019084168 A1 5/2019
WO WO-2019210216 A2 10/2019
WO WO-2019232251 A1 12/2019
WO WO-2019232253 A1 12/2019

OTHER PUBLICATIONS

Seyema et al. Mutations of the CD40 Ligand Gene and Its Effect on CD40 Ligand Expression in Patients With X-Linked Hyper IgM Syndrome. Blood. Oct. 1, 1998;92(7):2421-34. (Year: 1998).*
Barrett et al. Regulation of eukaryotic gene expression by the untranslated gene regions and other non-coding elements. Cell Mol Life Sci. Nov. 2012;69(21):3613-34. Epub Apr. 27, 2012. (Year: 2012).*
Leppek et al. Functional 5' UTR mRNA structures in eukaryotic translation regulation and how to find them. Nat Rev Mol Cell Biol. Mar. 2018;19(3):158-174. Epub Nov. 22, 2017. (Year: 2018).*
Clerte et al. The domains of polypyrimidine tract binding protein have distinct RNA structural preferences. Biochemistry. Mar. 17, 2009;48(10):2063-2074 (Year: 2009).*
Liu et al. J Biol Chem. Feb. 14, 2017;292(14):5624-5633. Biallelic insertion of a transcriptional terminator via the CRISPR/Cas9 system efficiently silences expression of protein-coding and non-coding RNA genes (Year: 2017).*
Clough, C. et al., "132. Targeting the BTK Locus in Primary Human Hematopoietic Cells with TALENs and AAV Donor Template", Molecular Therapy, May 1, 2016, vol. 24, No. Suppl. 1, pp. S54.
Dye, M.J., "Terminal Exon Definition Occurs Cotranscriptionally and Promotes Termination of RNA Polymerase II," Molecular Cell, Mar. 1999, vol. 3, pp. 371-378.
EP Search Report dated Feb. 23, 2022, in Application No. EP19812414.1.
Extended European Search Report dated Apr. 25, 2022, in Application No. EP19810629.6.
Hermaszewski, R.A ., & Webster, A.D.B., "Primary Hypogammaglobulinaemia: a Survey of Clinical Manifestations and Complications," QJM: An International Journal of Medicine, Jan. 1993, vol. 86(1), pp. 31-42.
Hubbard, N. et al., "Targeted gene editing restores regulated CD40L function in X-linked hyper-IgM syndrome", Blood, May 26, 2016, vol. 127, No. 21, pp. 2513-2522.
International Preliminary Report on Patentability dated Dec. 10, 2020 in PCT Application No. PCT/US2019/034713.
International Preliminary Report on Patentability dated Dec. 10, 2020 in PCT Application No. PCT/US2019/034715.
International Search Report and Written Opinion dated Oct. 9, 2019 in PCT Application No. PCT/US2019/034713.
International Search Report and Written Opinion dated Oct. 18, 2019 in PCT Application No. PCT/US2019/034715.
Kohn, D.B. et al., "New Frontiers in the Therapy of Primary Immunodeficiency: From Gene Addition to Gene Editing", The Journal of allergy and clinical immunology, Mar. 2017, vol. 139, No. 3, pp. 726-732.
Kuo, C.Y. et al., "Site-Specific Gene Editing of Human Hematopoietic Stem Cells for X-Linked Hyper-IgM Syndrome", Cell reports, May 29, 2018, vol. 23, No. 9, pp. 2606-2616.
Kuo, C.Y., et al., "Targeted Gene Therapy in the Treatment of X-linked Hyper-IgM Syndrome," Gene Targeting and Gene Correction I, May 2014, vol. 22(1), p. S36.
Ng. Y.Y. et al., "Correction of B-cell Development in Btk-deficient Mice Using Lentiviral Vectors With Codon-optimized Human BTK", Leukemia, 2010, vol. 24, pp. 1617-1630.
Ravin, S.S.De., et al., "Lentiviral Hematopoietic Stem Cell Gene Therapy for X-linked Severe Combined Immunodeficiency," Science translational medicine, Apr. 20, 2016, vol. 8(335): 33ra57, 12 pages.
Seyama, K. et al., "Mutations of the CD40 ligand gene and its effect on CD40 ligand expression in patients with X-linked hyper IgM syndrome", Blood, Oct. 1, 1998, vol. 92, No. 7, pp. 2421-2434.
Shaul, O., "How Introns Enhance Gene Expression," The international journal of biochemistry & cell biology, Oct. 2017, vol. 9(Pt B), pp. 145-155.
Siegal, F.P, et al., "Lymphocytes in Human Immunodeficiency States: a Study of Membrane-associated Immunoglobulins," European Journal of Immunology, 1971, vol. 1(6), pp. 482-486.
Tsukada, S., et al., "Deficient Expression of a B Cell Cytoplasmic Tyrosine Kinase in Human X-linked Agammaglobulinemia," Cell, Jan. 29, 1993, vol. 279-290.
Brown et al., "Thymic lymphoproliferative disease after successful correction of CD40 ligand deficiency by gene transfer in mice", Nature Medicine, Nov. 1998; 4(11): 1253-1260.
De La Morena, et al., "Long-term outcomes of 176 patients with X-linked hyper-IgM syndrome treated with or without hematopoietic cell transplantations", Journal of Allergy and Clinical Immunology, Apr. 2017; 139(4):1282-1292.
Dull et al., "A third-generation lentivirus vector with a conditional packaging system", Journal of Virology, Nov. 1998, 72(11): 8463-8471.
Ebina et al., "Harnessing the CRISPR/Cas9 system to disrupt latent HIV-1 provirus", Scientific Reports, Aug. 26, 2013; 3: 2510.
Gennery et al., "Treatment of CD40 ligand deficiency by hematopoietic stem cell transplantation: a survey of the European experience, 1993-2002", Blood, Oct. 2, 2003; 103(3):1152-1157.
Hayward et al., "Cholangiopathy and tumors of the pancreas, liver, and biliary tree in boys with X-linked immunodeficiency with hyper-Ig,M", Journal of Immunology, Jan. 15, 1997; 158(2): 977-983.
Hollenbaugh et al., "The random inactivation of the X chromosome carrying the defective gene responsible for X-linked hyper IgM syndrome (X-HIM) in female carriers of HIGM1", The Journal of Clinical Investigation, Aug. 1994; 94(2): 616-622.
Hu et al., "Heritable gene-targeting with gRNA/Cas9 in rats", Cell Research, Oct. 22, 2013; 23:1322-1325.
Levy et al., "Clinical spectrum of X-linked hyper-IgM syndrome", The Journal of Pediatrics, Jul. 1997; 131(1): 47-54.
Mitsui-Sekinaka et al., "Clinical features and hematopoietic stem cell transplantations for CD40 ligand deficiency in Japan", Journal of Allergy and Clinical Immunology, Mar. 31, 2015; 136(4): 1018-1024.
Saifuddin et al., "Phosphorylation and the regulation of CD40L mRNA stability by polypyrimidine tract binding protein (P1394)", J. Immunol., May 1, 2013; 190(1_Supplement): 203.14. (abstract only).
Tsai et al., "GUIDE-seq enables genome-wide profiling of off-target cleavage by CRISPR-Cas nucleases", Nat. Biotechnol., Feb. 2015; 33(2):187-197. doi: 10.1038/nbt.3117.
Zufferey et al., "Self-inactivating lentivirus vector for safe and efficient in vivo gene delivery", Journal of Virology, Dec. 1998; 72(12): 9873-9880.
Follenzi et al., "Gene transfer by lentiviral vectors is limited by nuclear translocation and rescued by HIV-1 pol sequences", Nature Genetics, Jun. 2000; 25: 217-222.
Gundry et al., "Technical considerations for the use of CRISPR/Cas9 in hematology research", Experimental Hematology (2017) 54:4-11.
Arai et al., "Genetic analysis of contiguous X-chromosome deletion syndrome encompassing the BTK and TIMM8A genes", Journal of Human Genetics (2011) 56:577-582.
Huang et al., "ExUTR: a novel pipeline for large-scale prediction of 3'-UTR sequences from NGS data", BMC Genomics (2017) 18:847.
Pesole et al., "Structural and functional features of eukaryotic mRNA untranslated regions", Gene (2001) 276(1-2):73-81.
Mignone et al., "Untranslated regions of mRNAs", Genome Biology (2002) 3(3):reviews0004.1-0004.10.
Laughlin et al., "Functional analysis of a tripartite stability element within the CD40 ligand 3' untranslated region", Immunology (2008) 124(3):368-379.

* cited by examiner

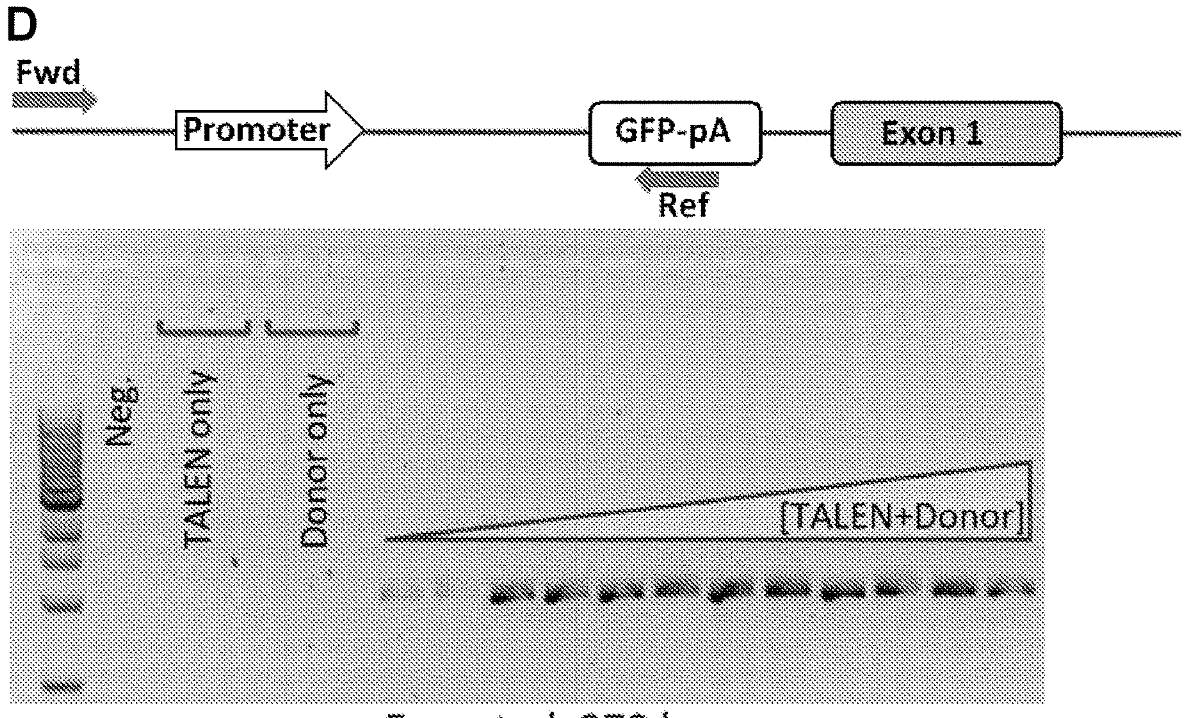
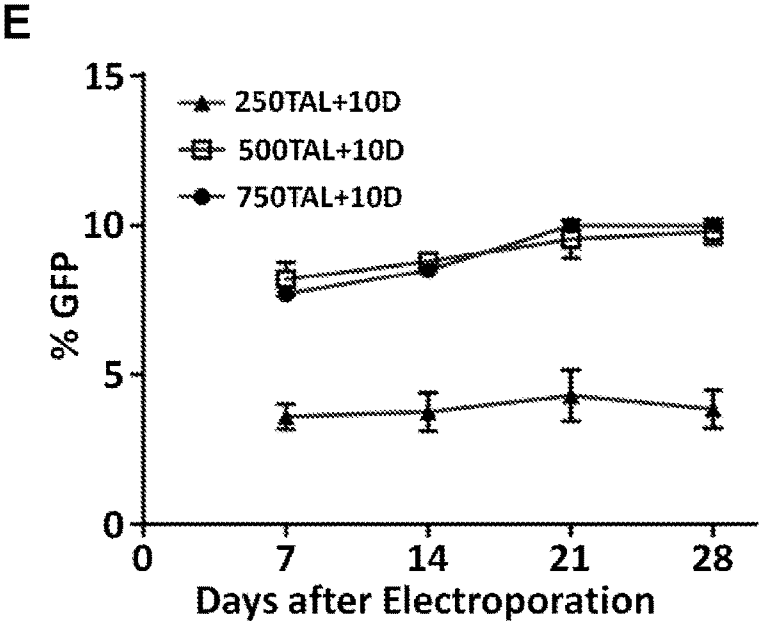
*Fig. 1, cont'd.*

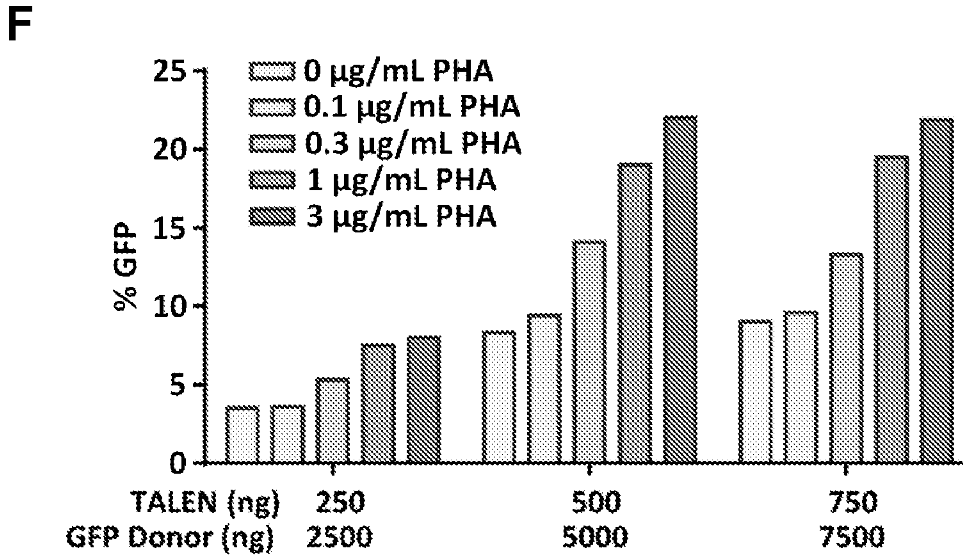
*Fig. 1, cont'd.*

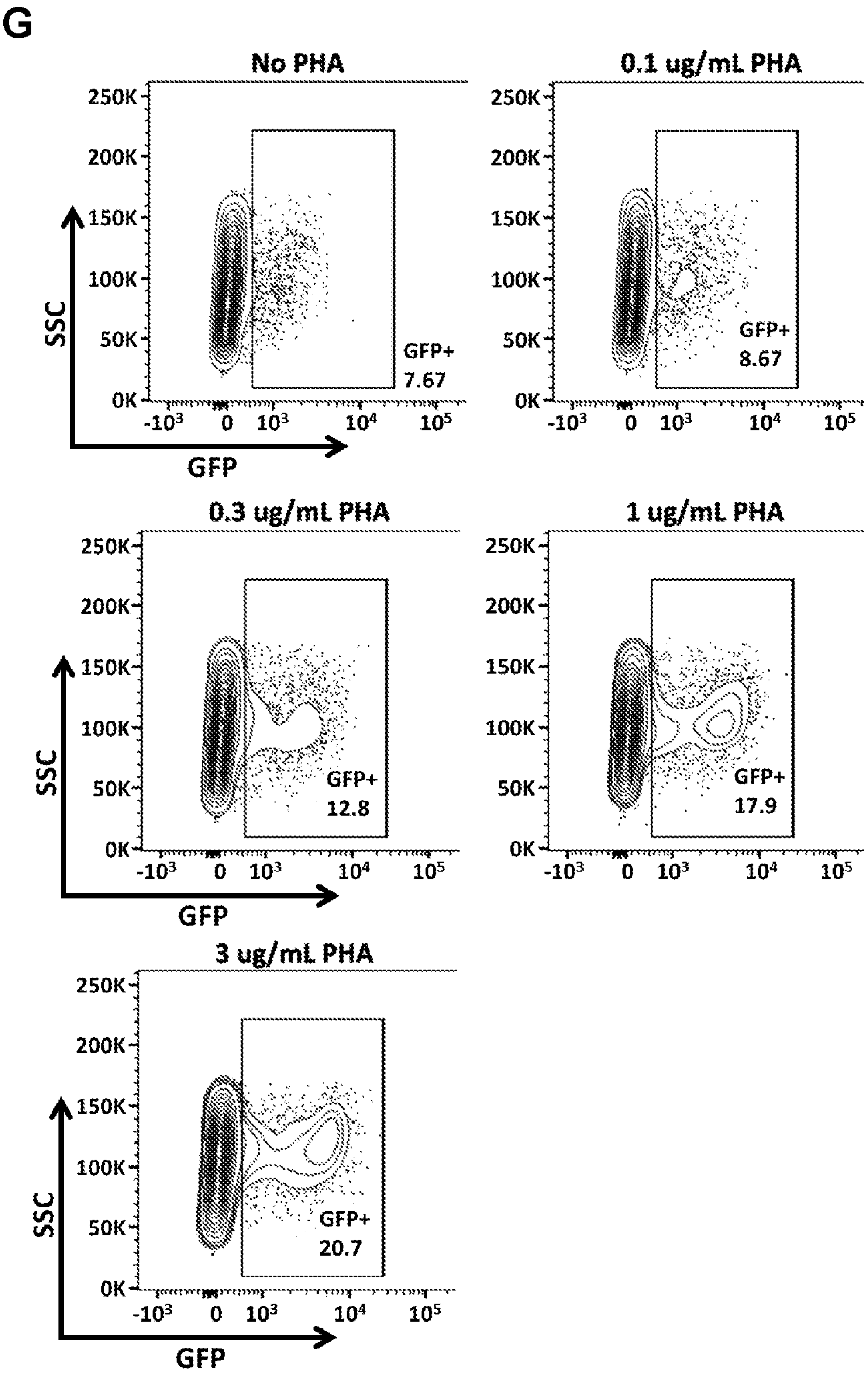
*Fig. 1, cont'd.*

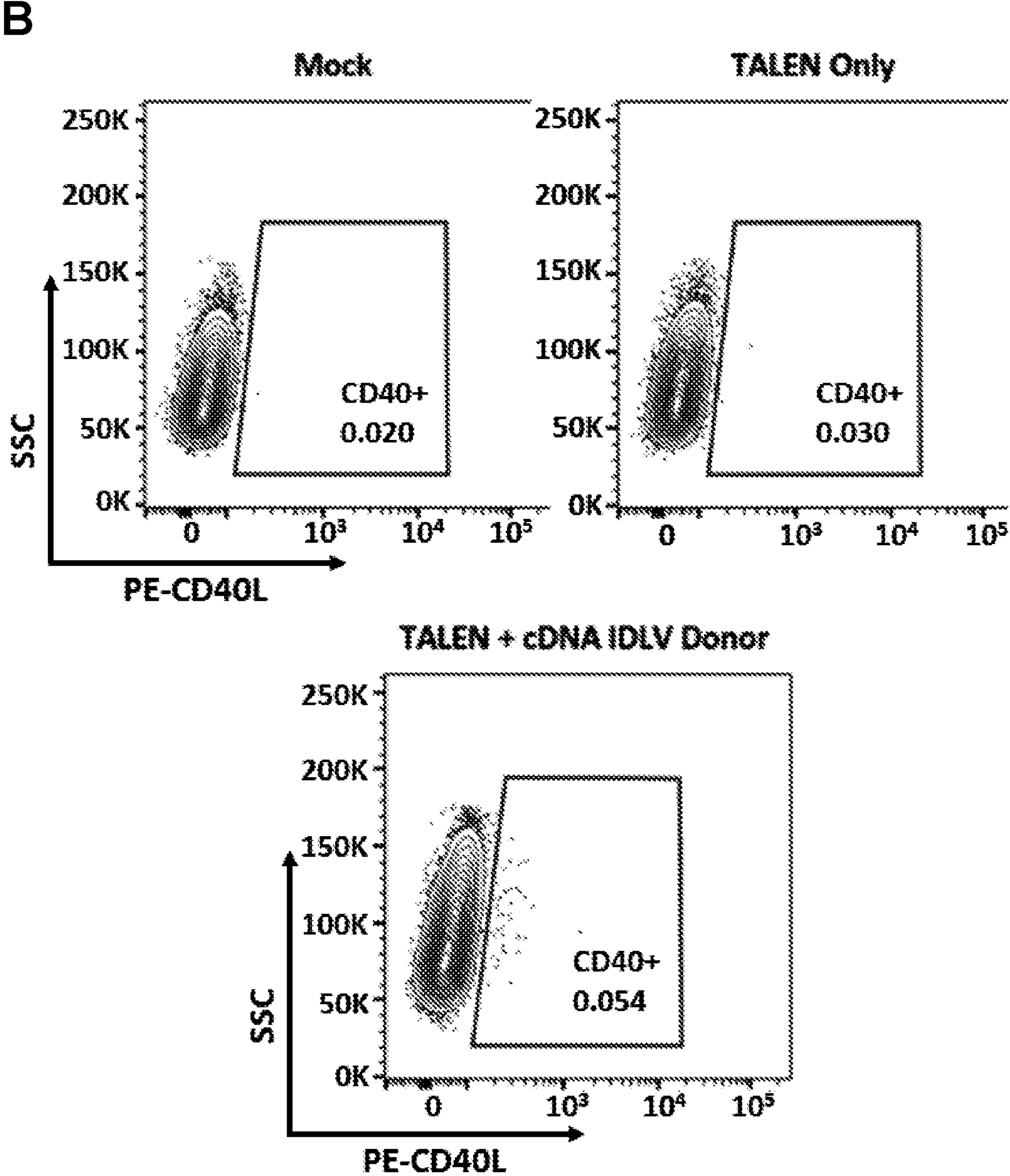
*Fig. 2, cont'd.*

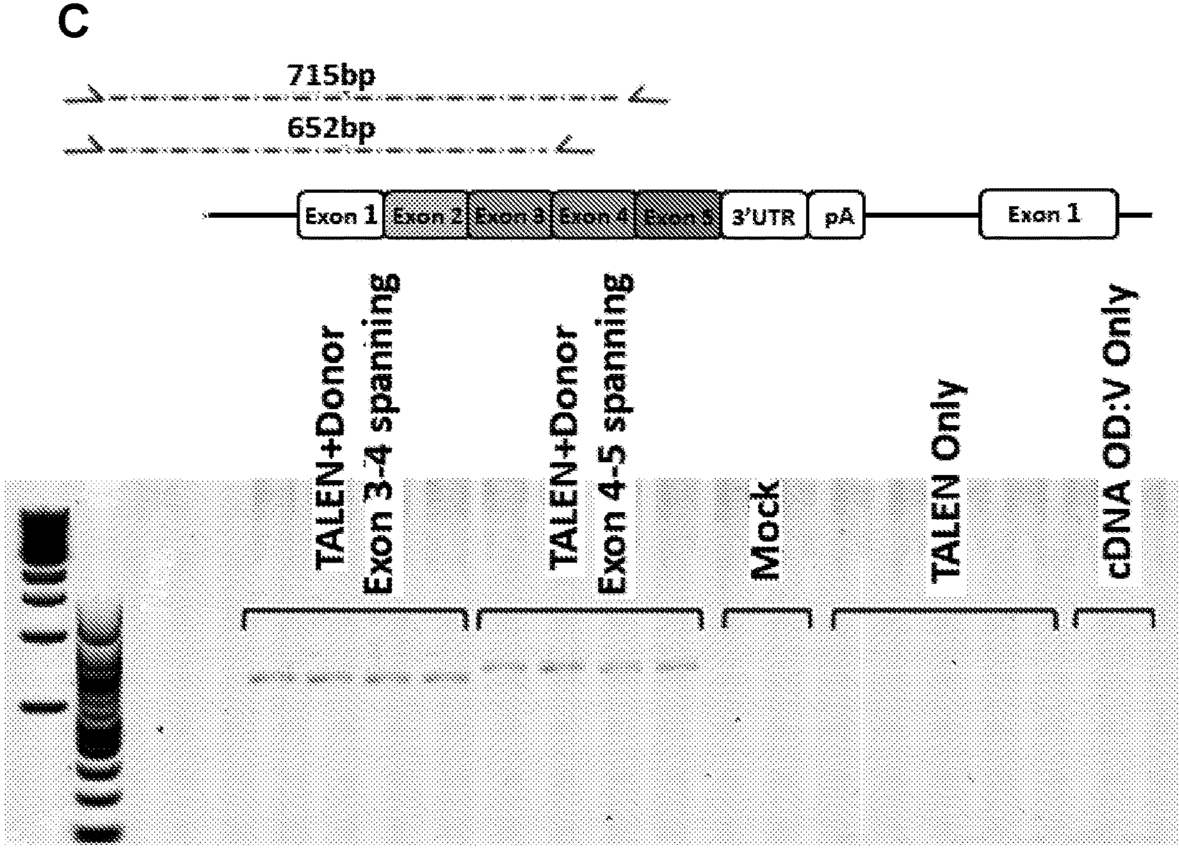
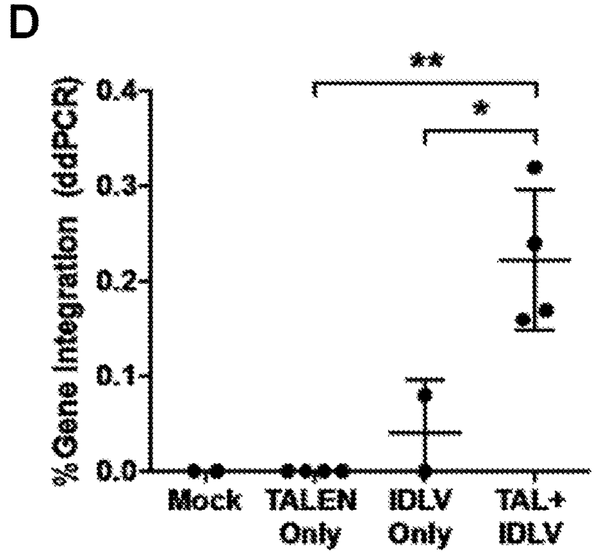
*Fig. 2, cont'd.*

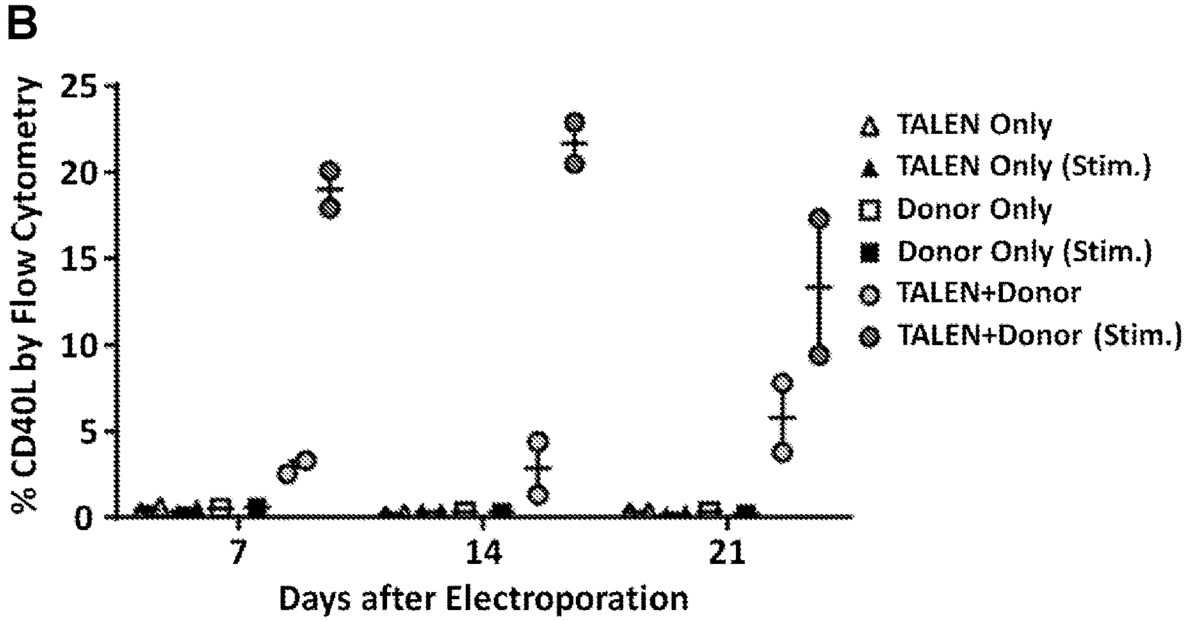
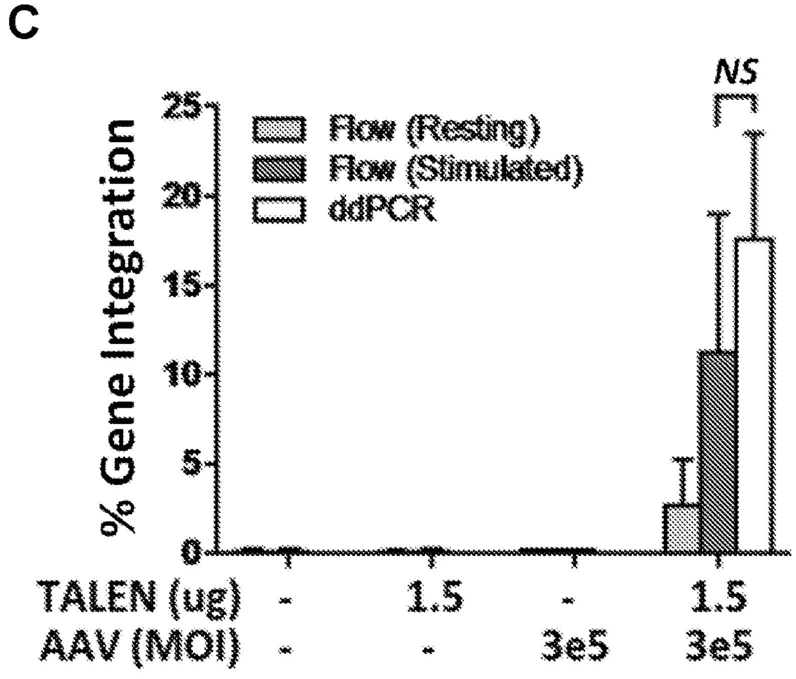
*Fig. 3, cont'd.*

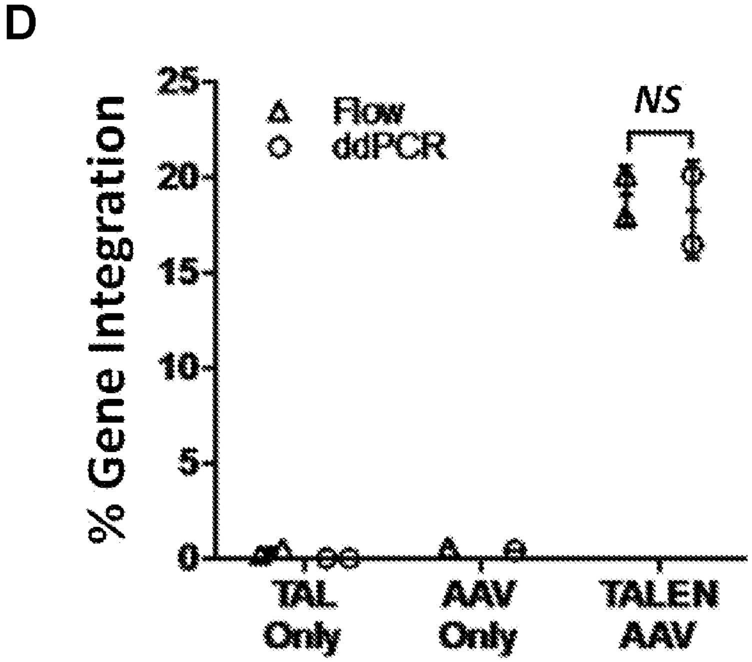
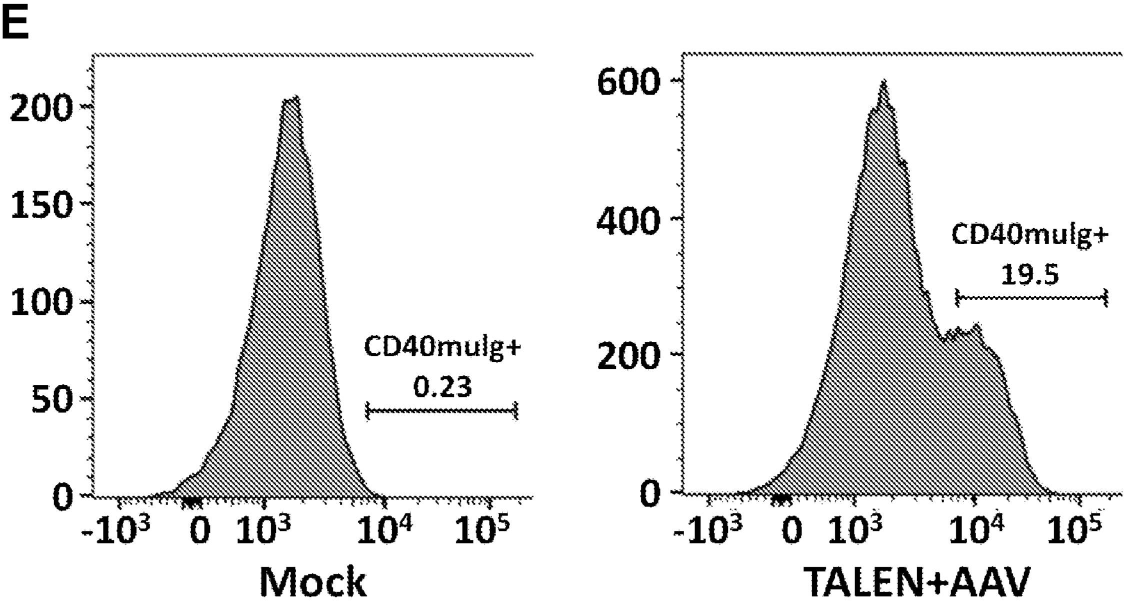
*Fig. 3, cont'd.*

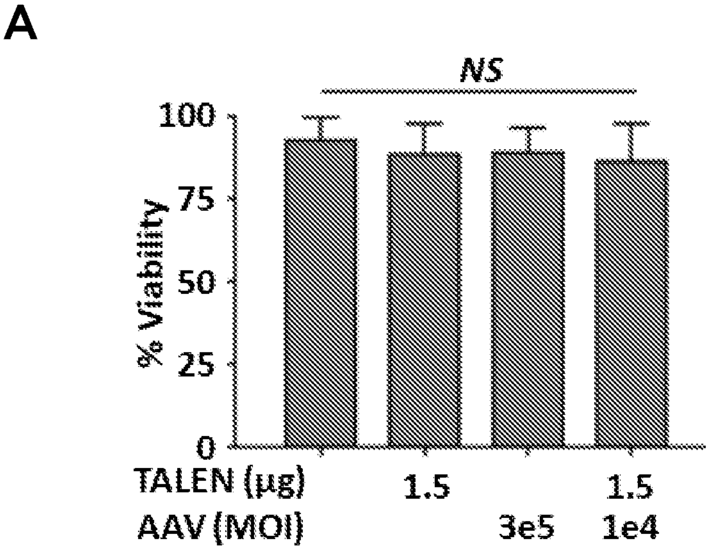
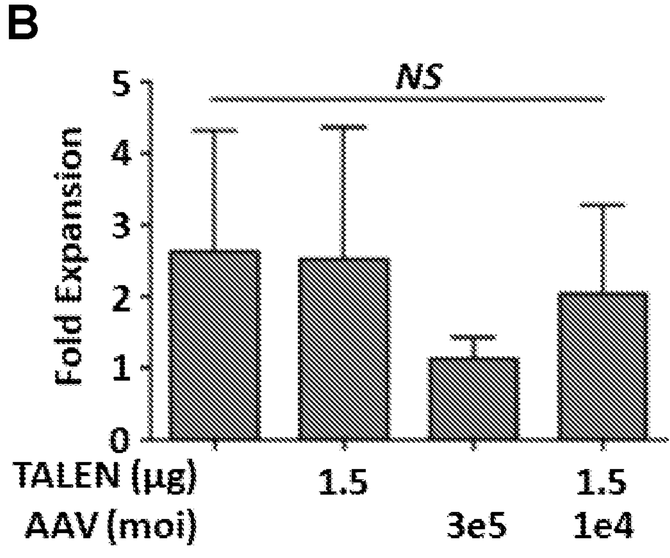
*Fig. 4*

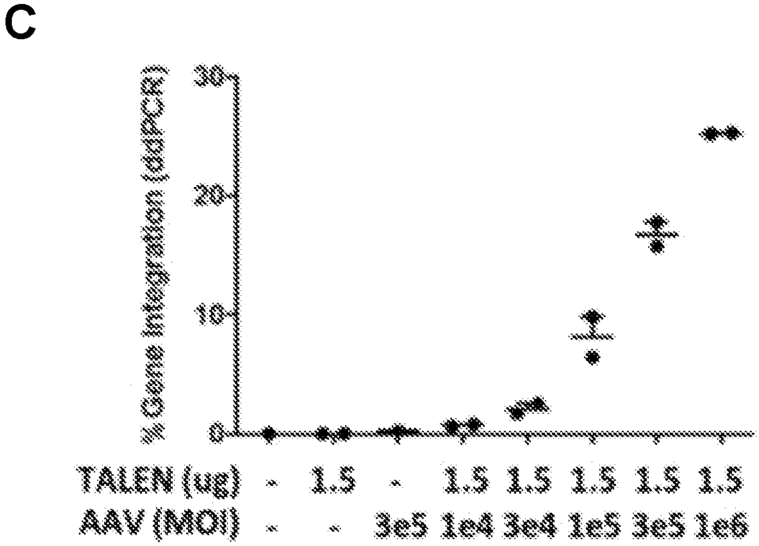
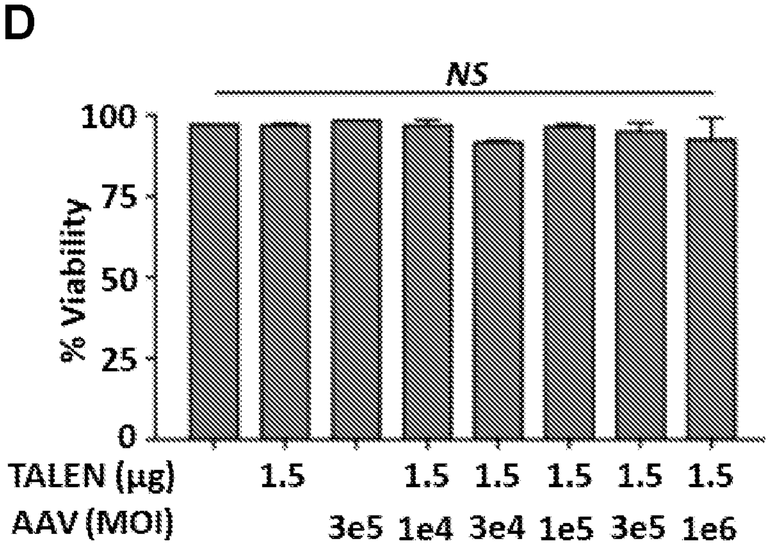
*Fig. 4, cont'd.*

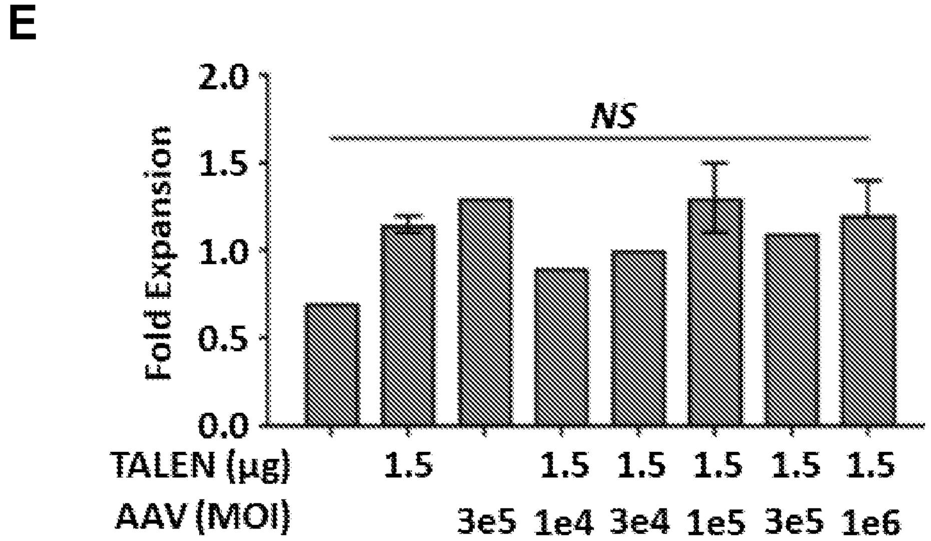
*Fig. 4, cont'd.*

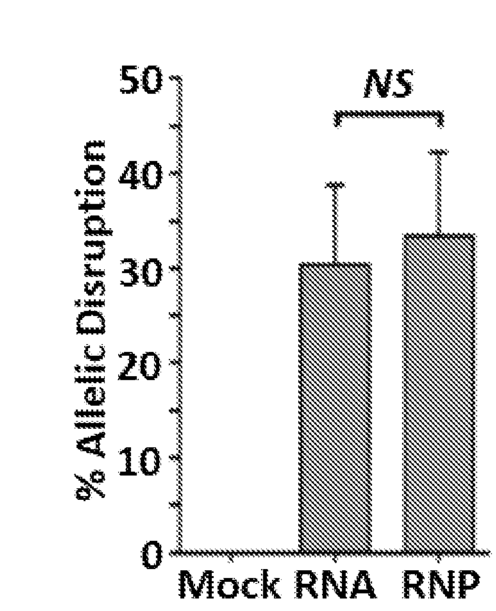
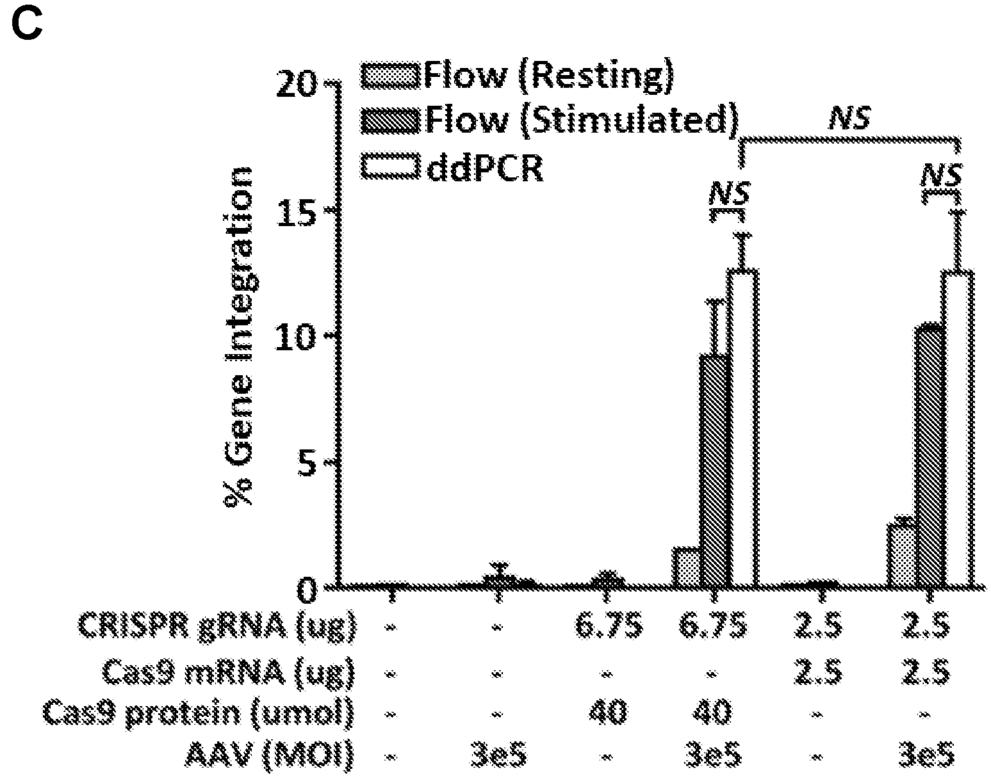
*Fig. 5, cont'd.*

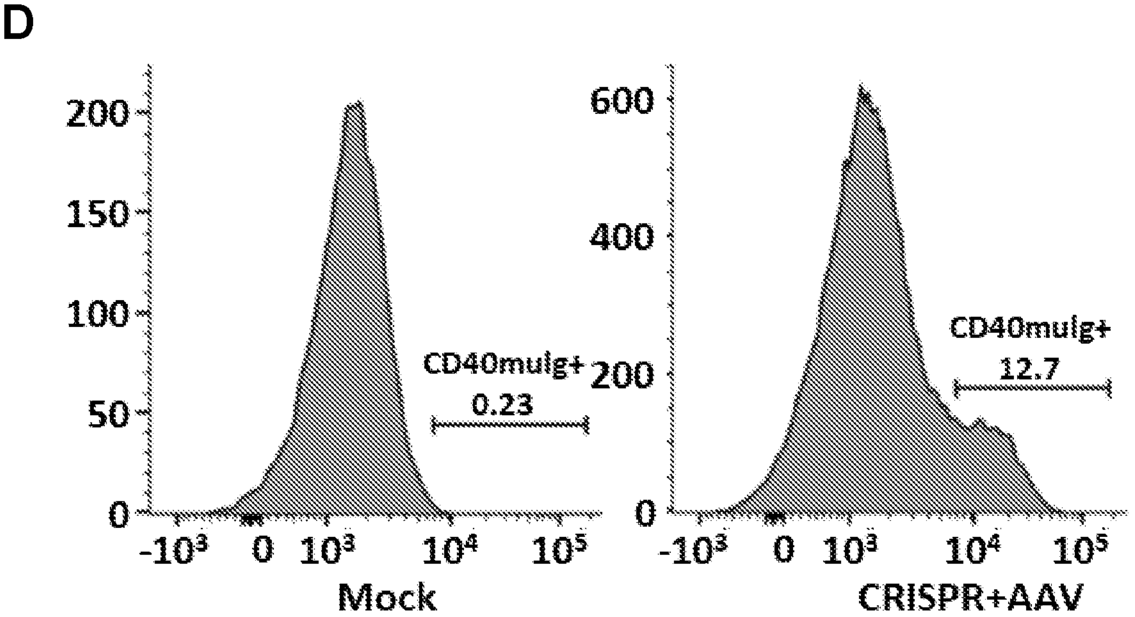
*Fig. 5, cont'd.*

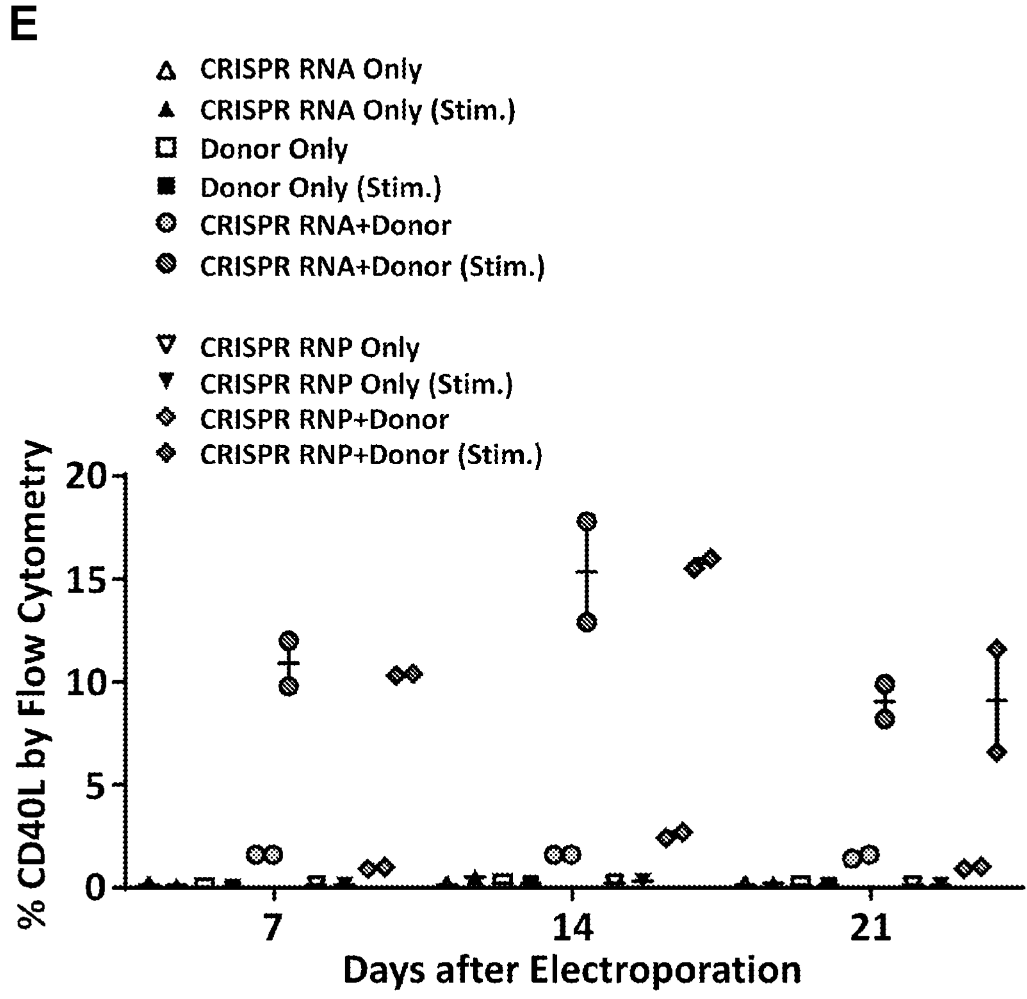
*Fig. 5, cont'd.*

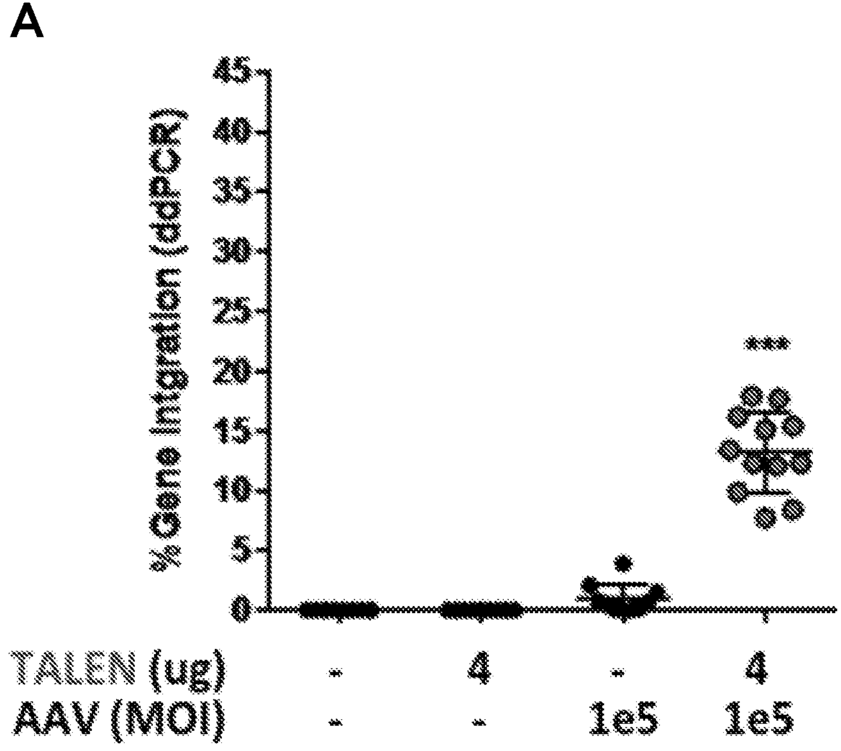
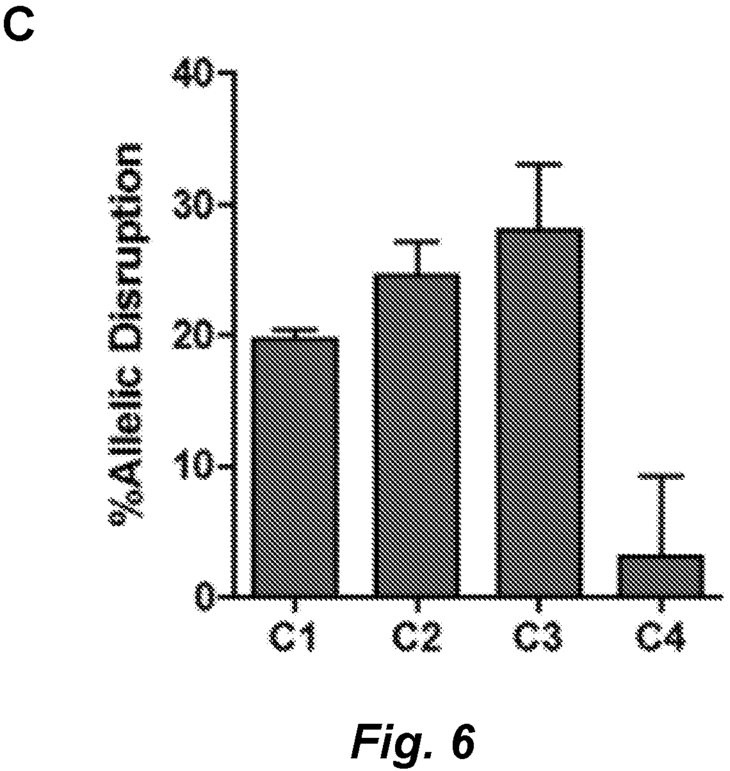
*Fig. 6*

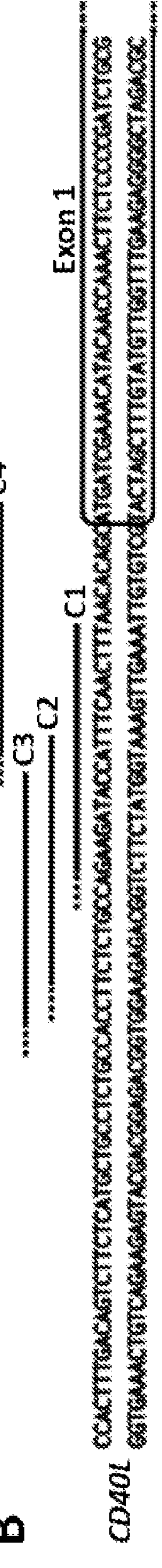
Fig. 6, cont'd.

D
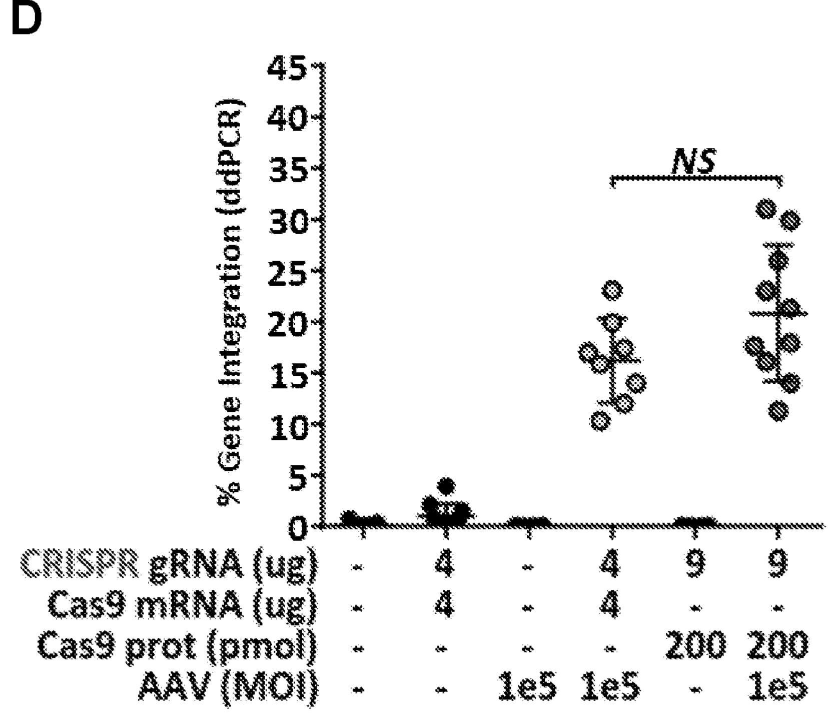
E
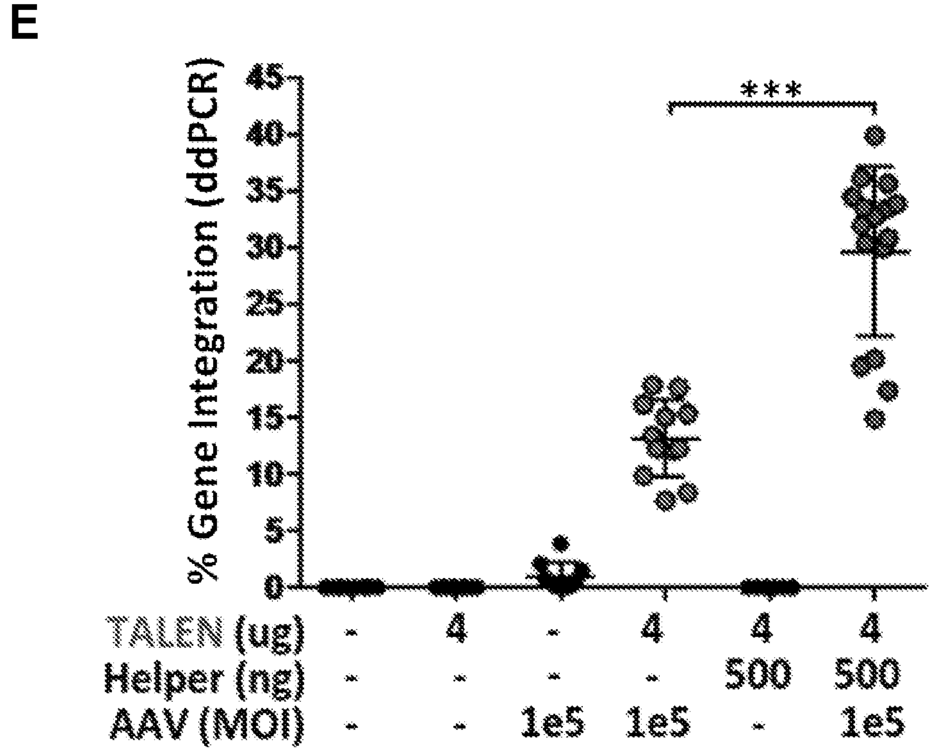
*Fig. 6, cont'd.*

F
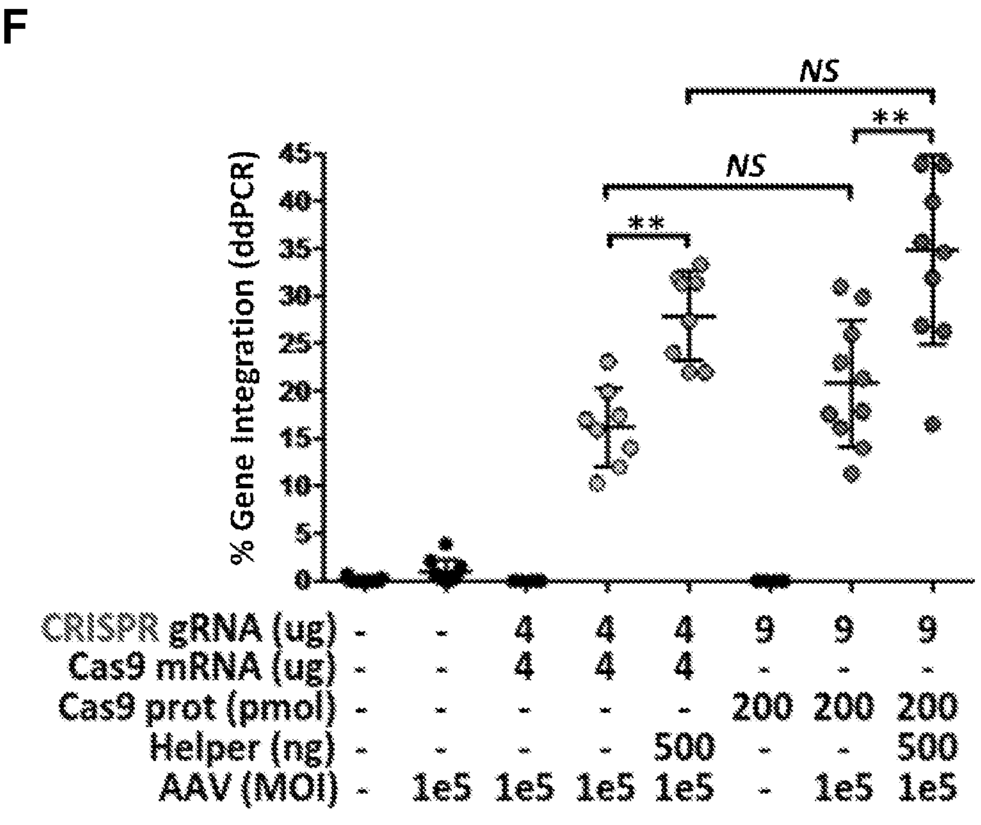
G
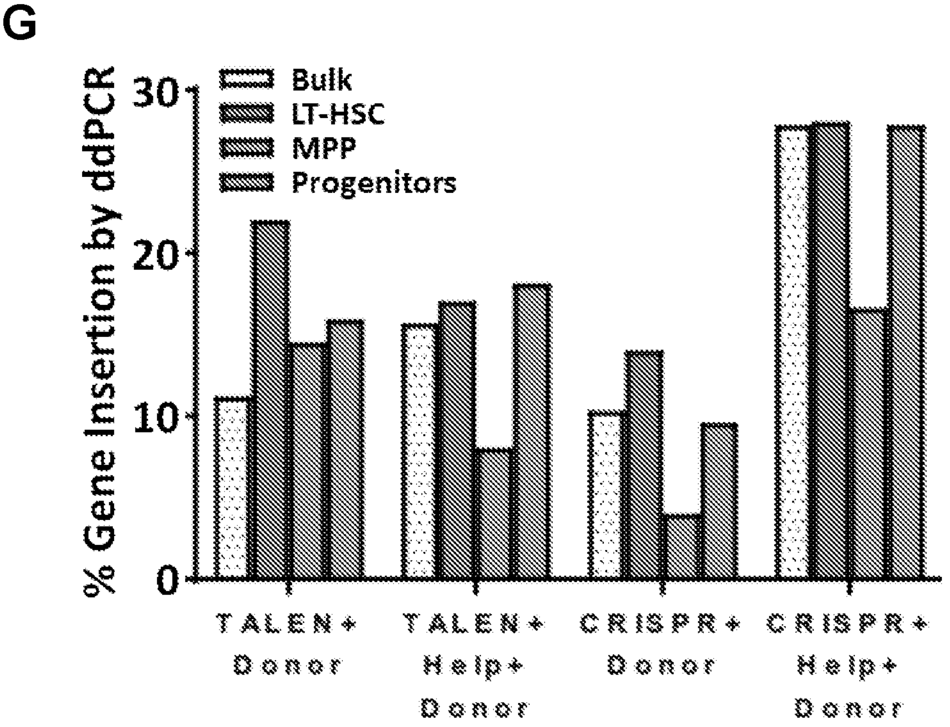
*Fig. 6, cont'd.*

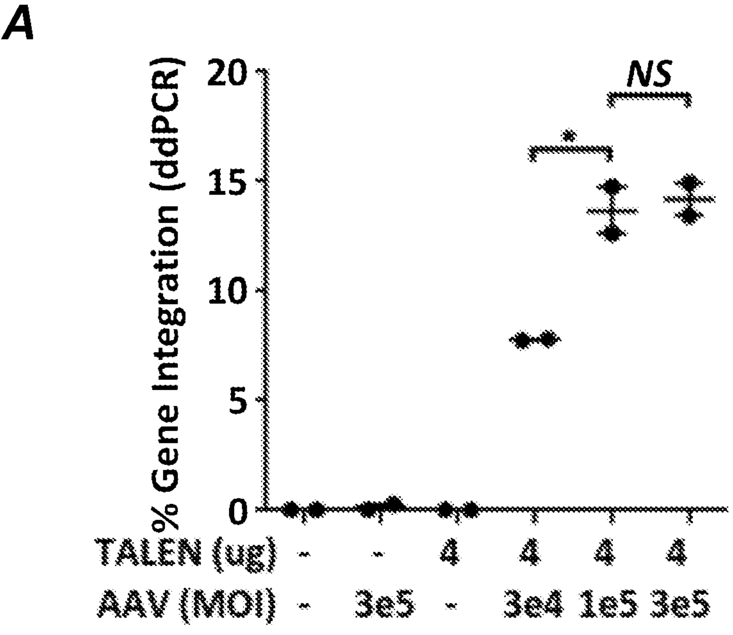
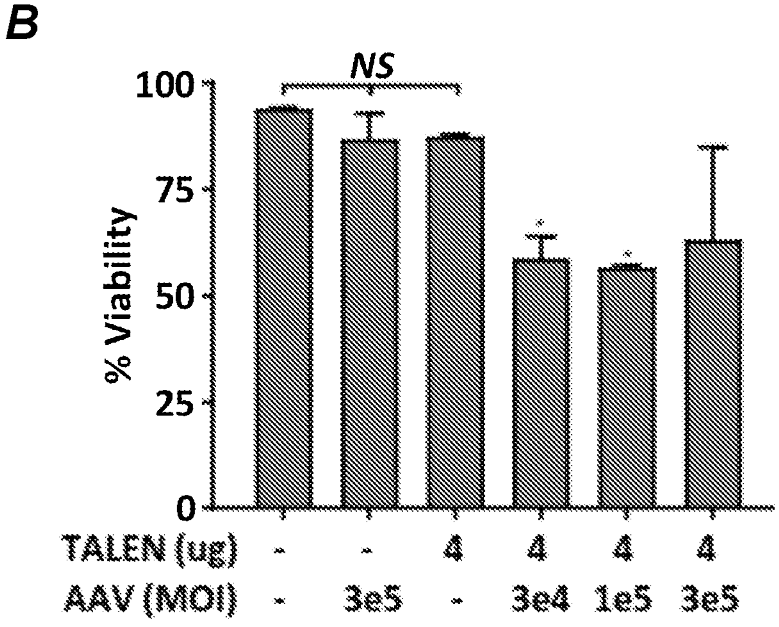
*Fig. 7*

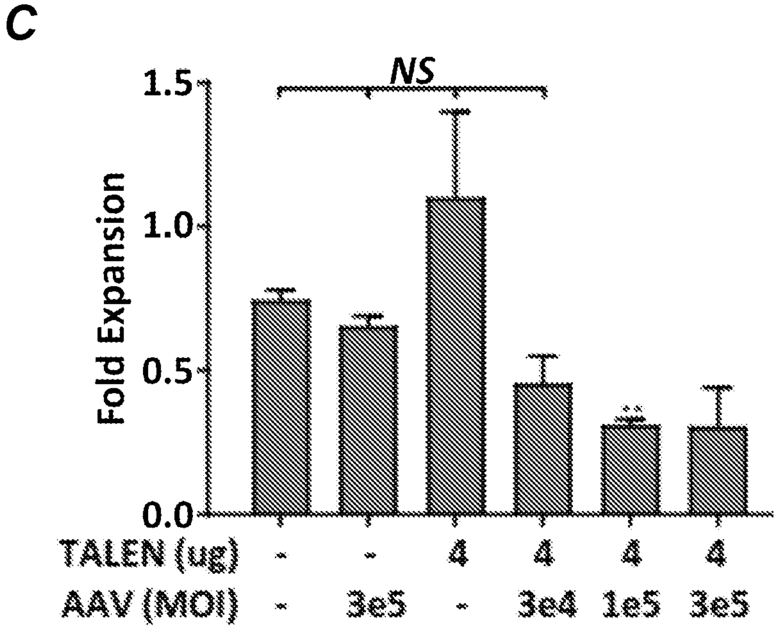
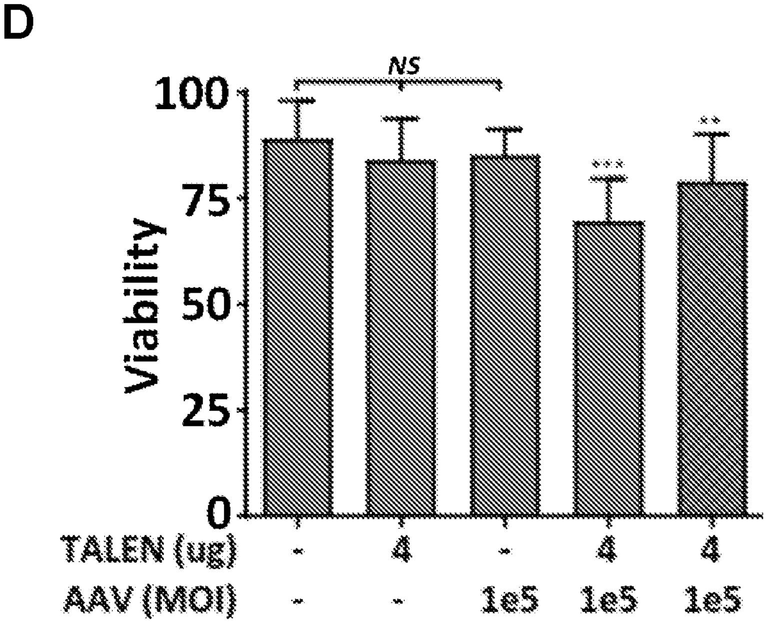
*Fig. 7, cont'd.*

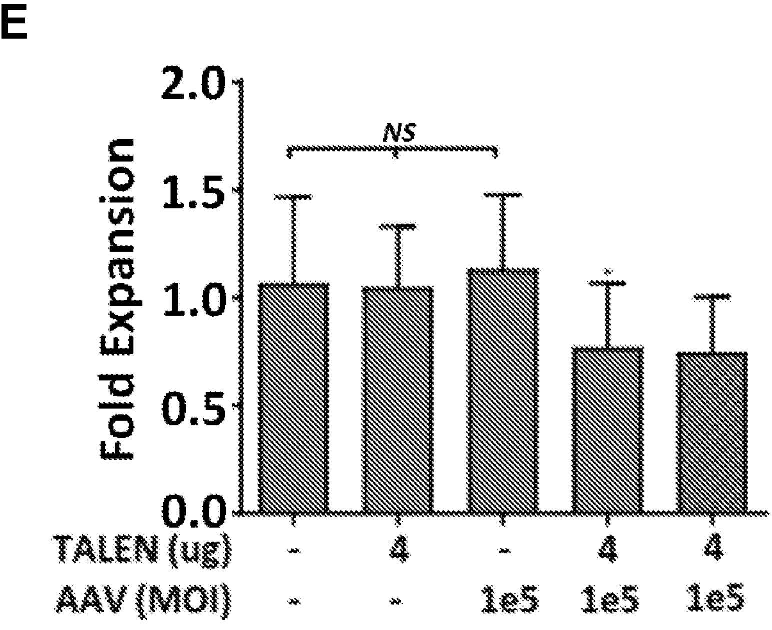
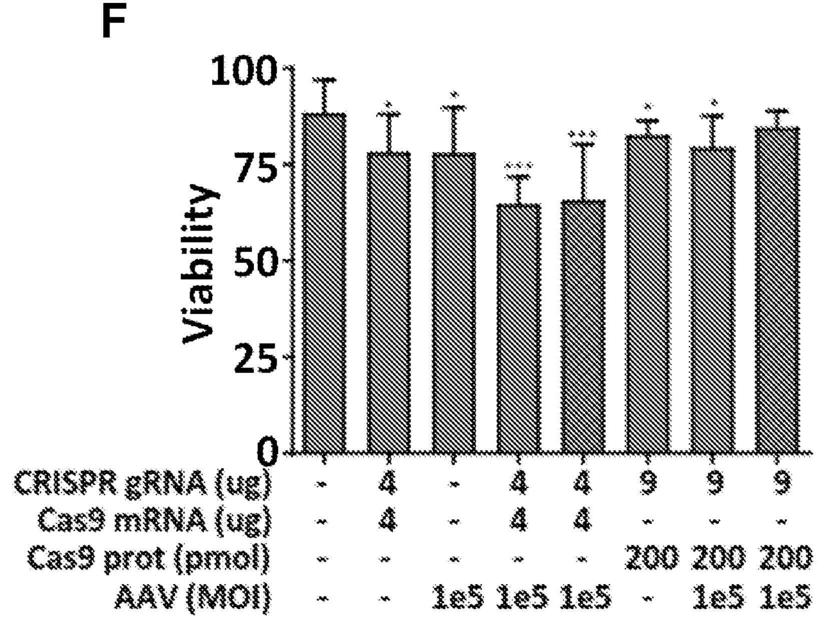
*Fig. 7, cont'd.*

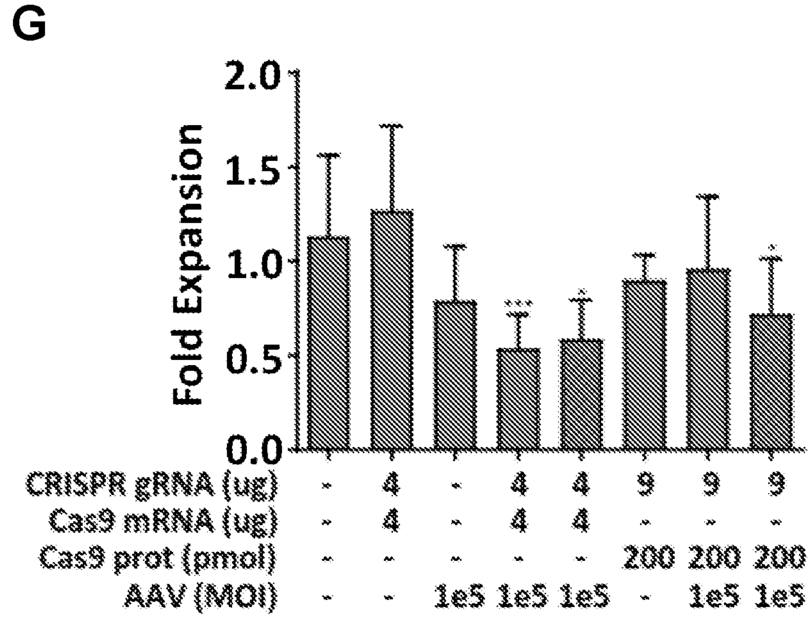
*Fig. 7, cont'd.*

A
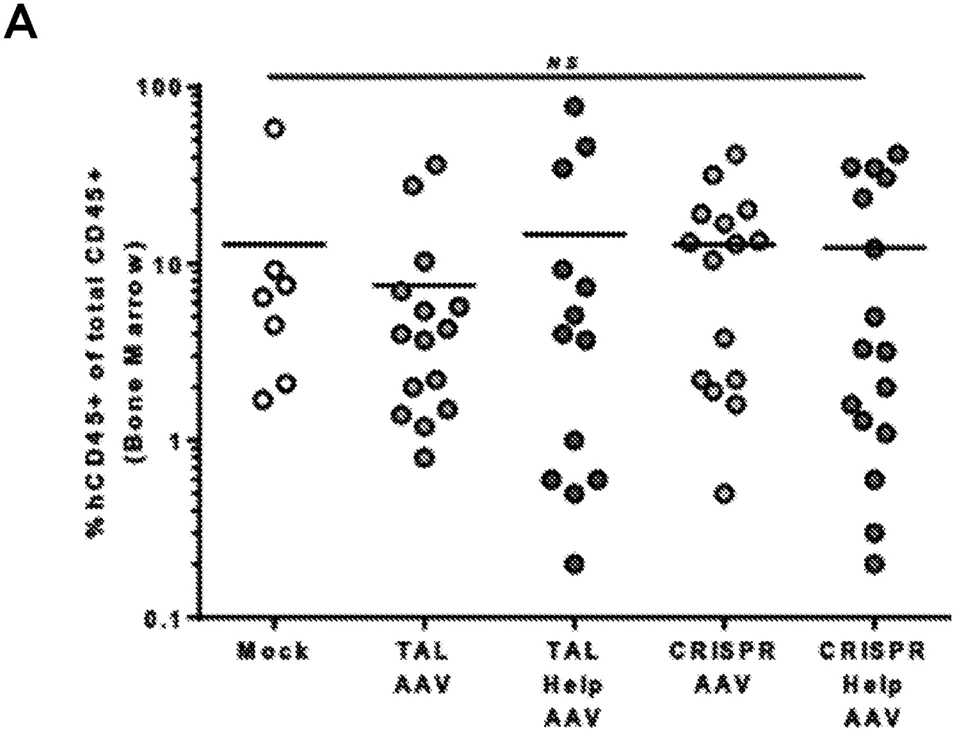
B
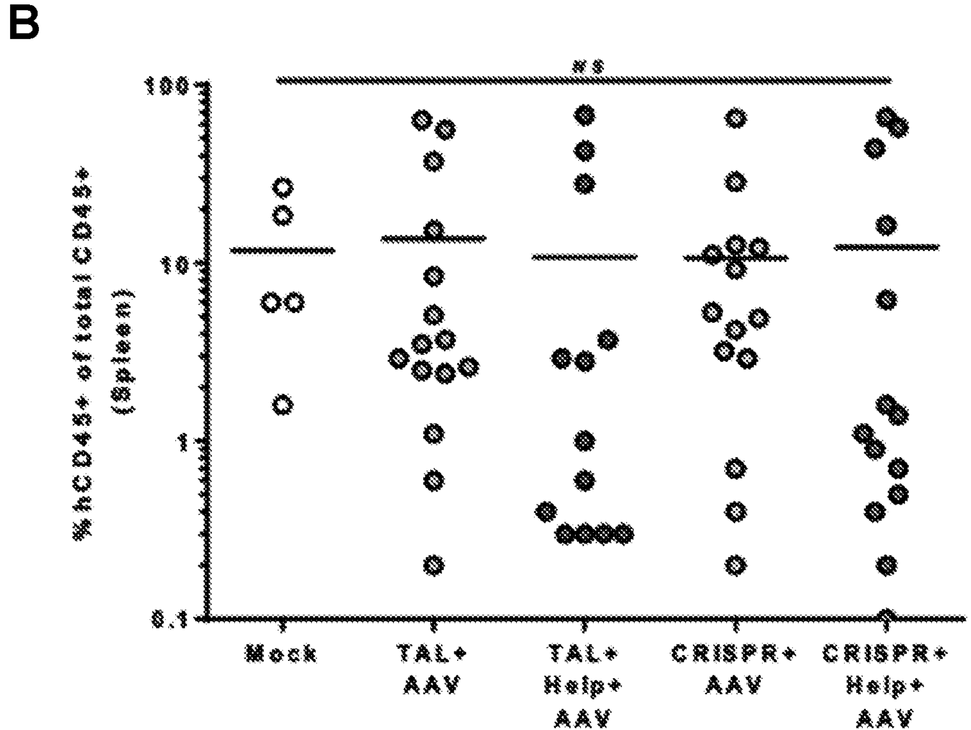
*Fig. 9*

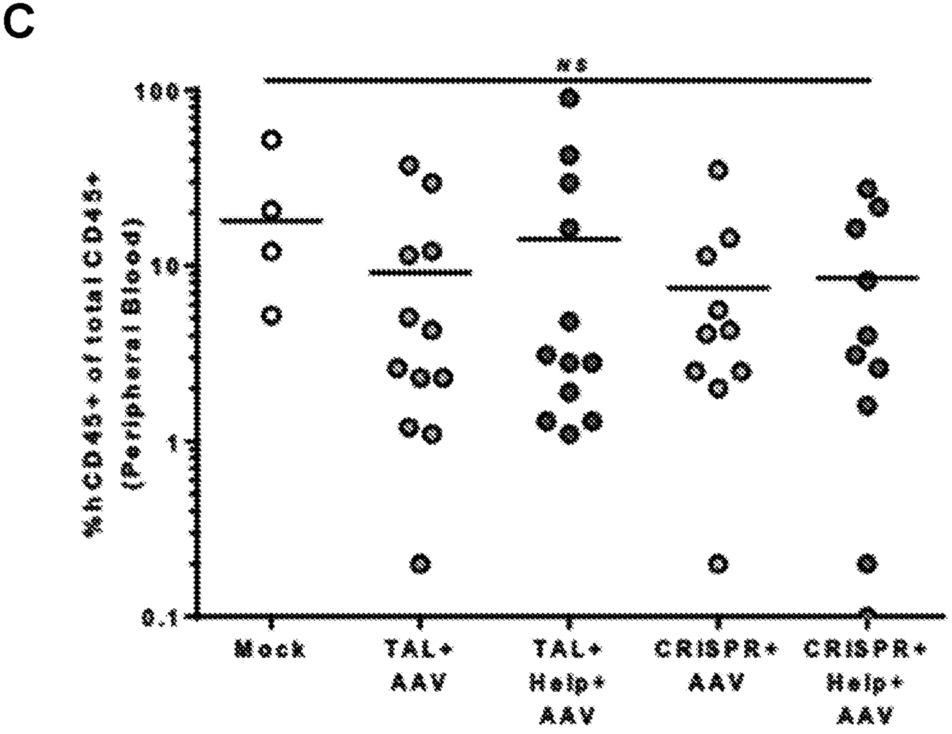
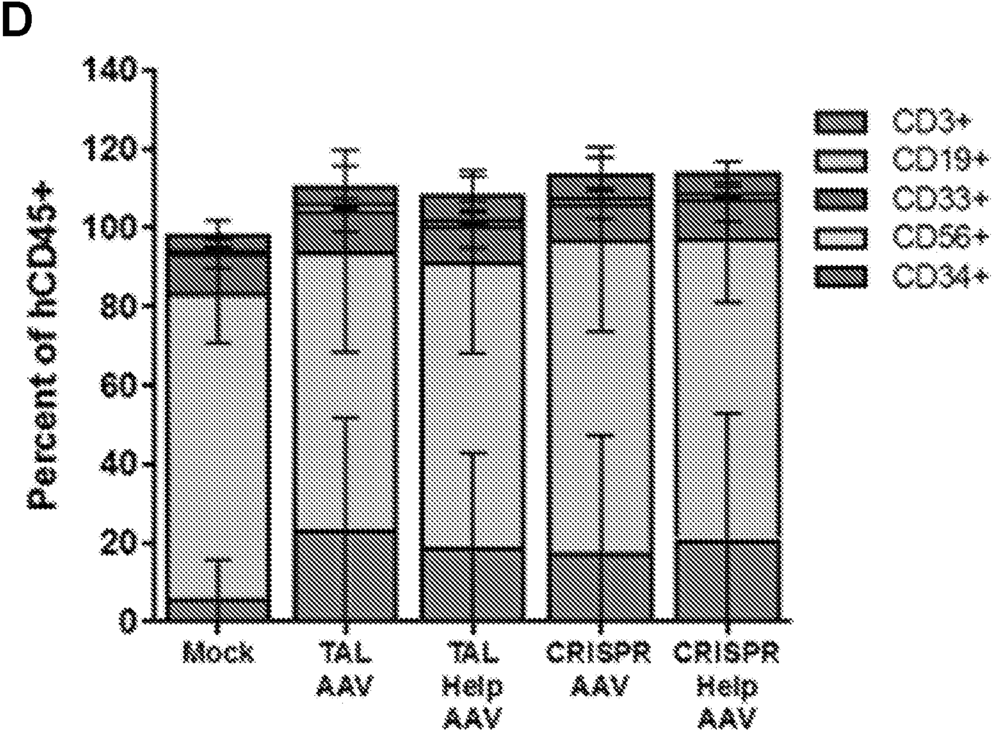
*Fig. 9, cont'd.*

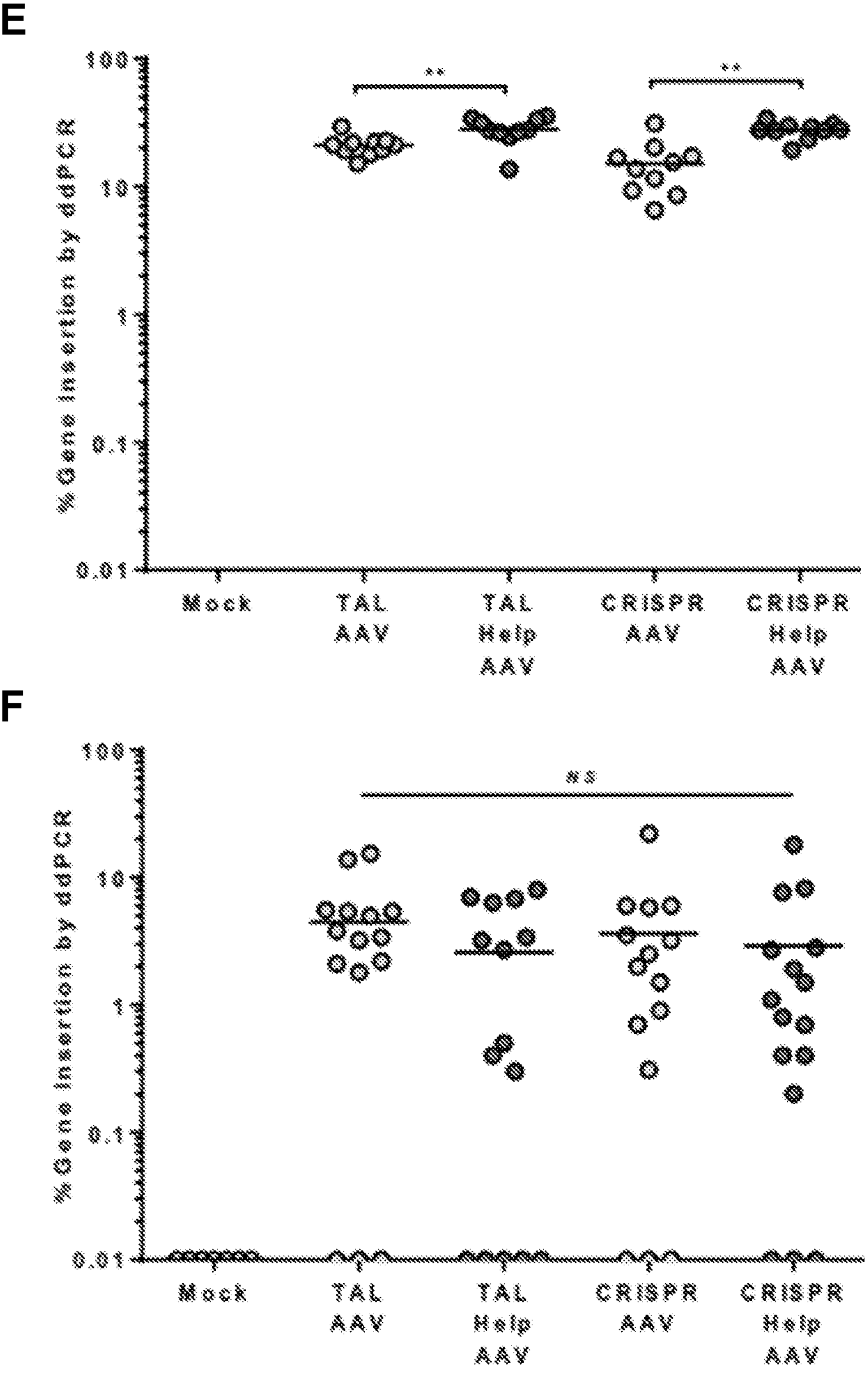
*Fig. 9, cont'd.*

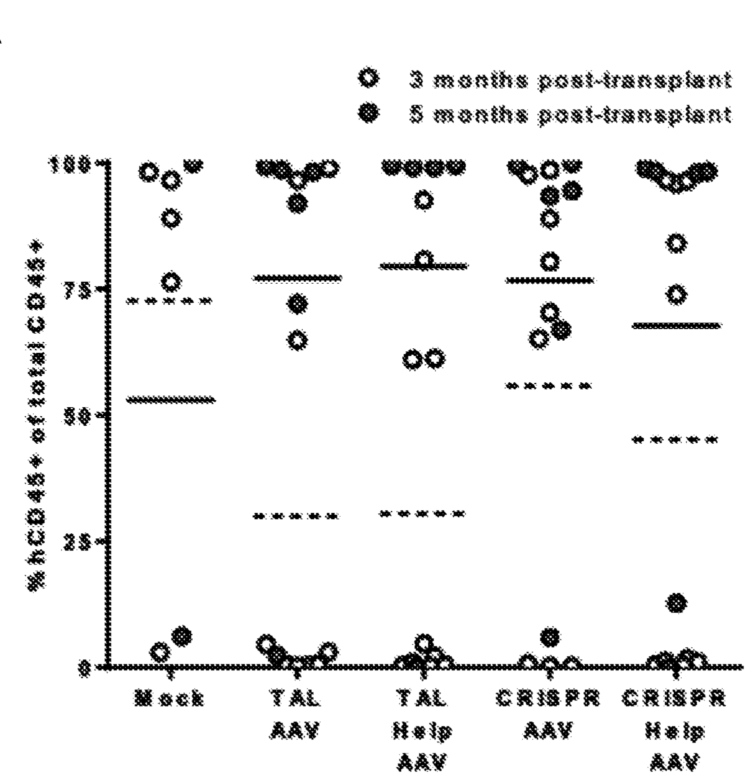
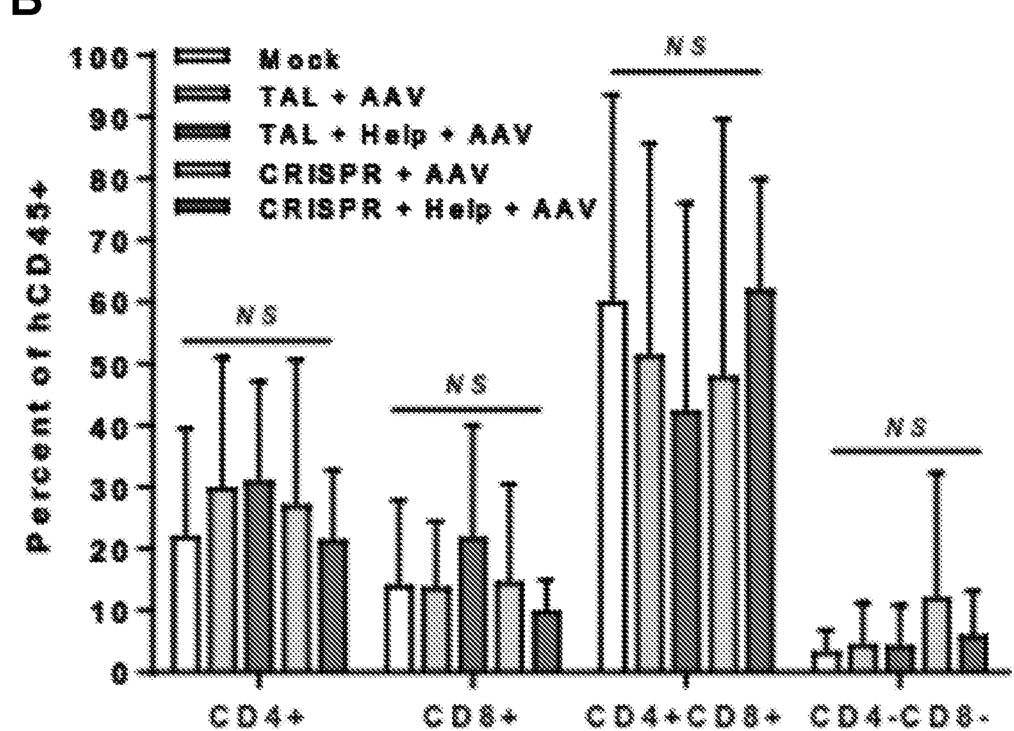
*Fig. 10*

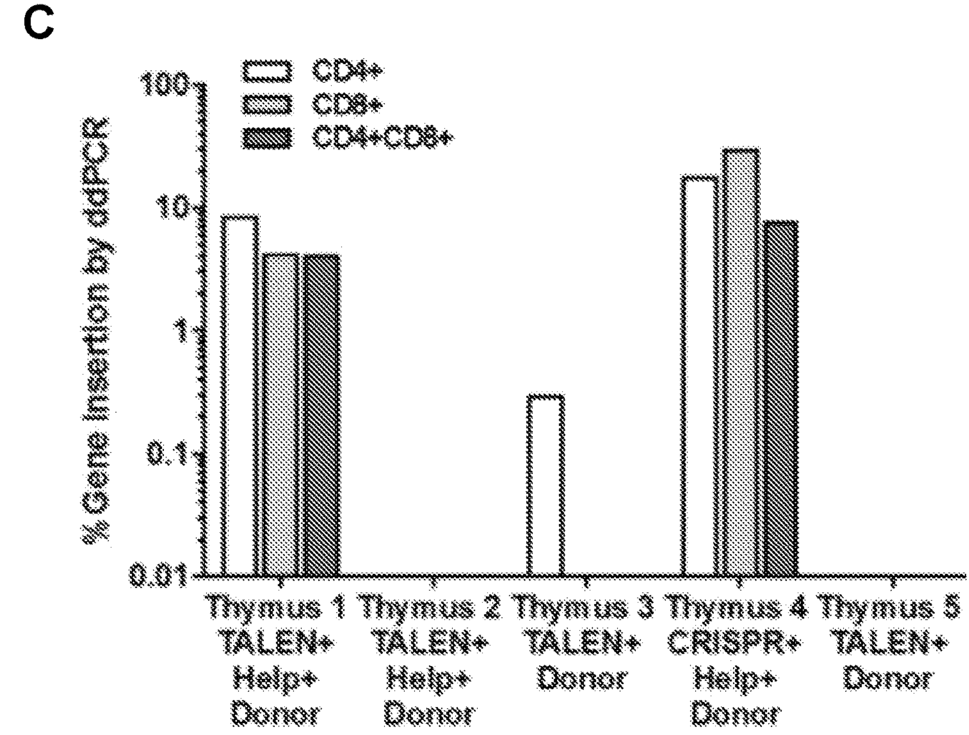
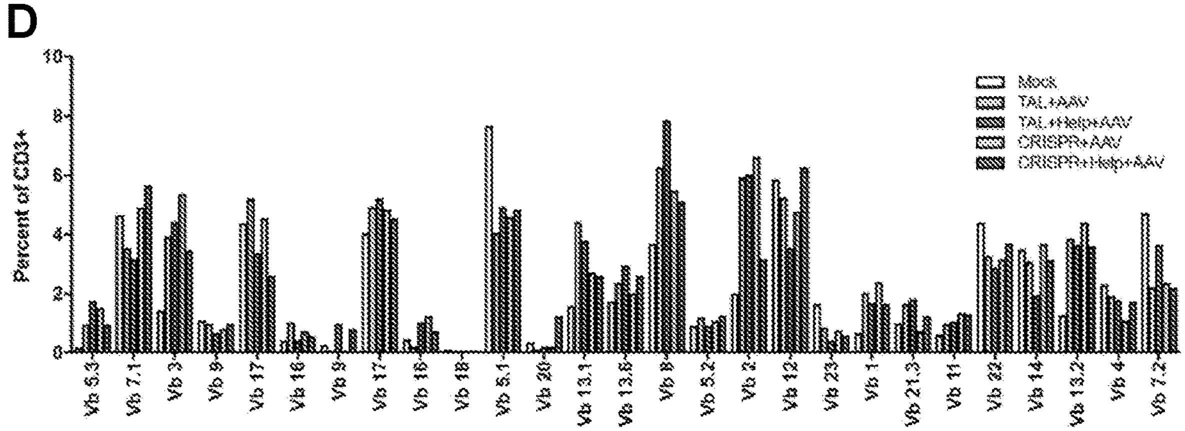
*Fig. 10, cont'd*

A
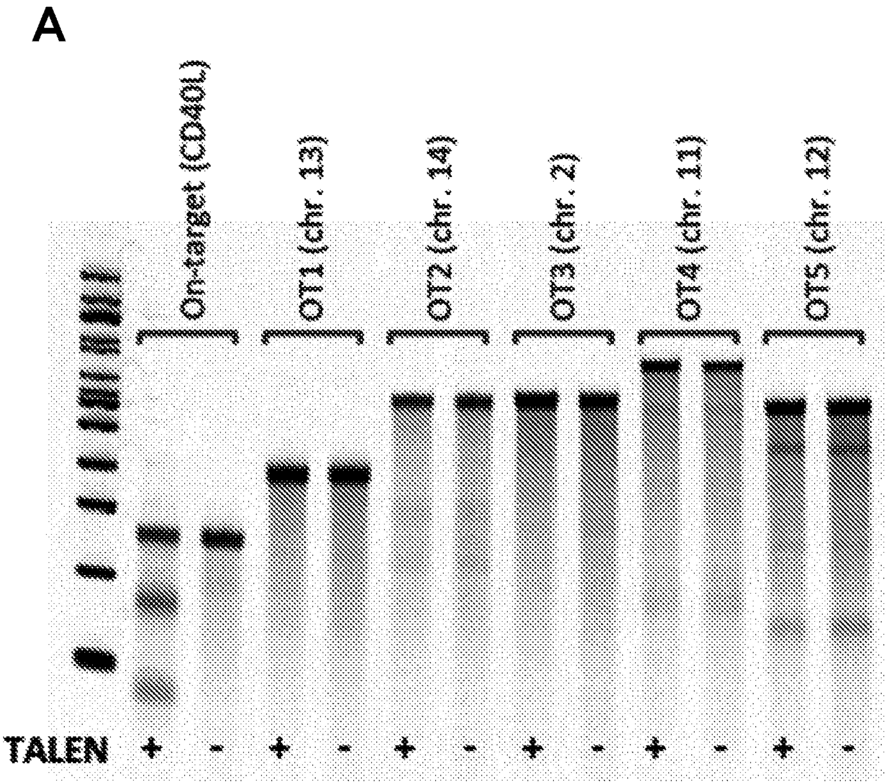
B
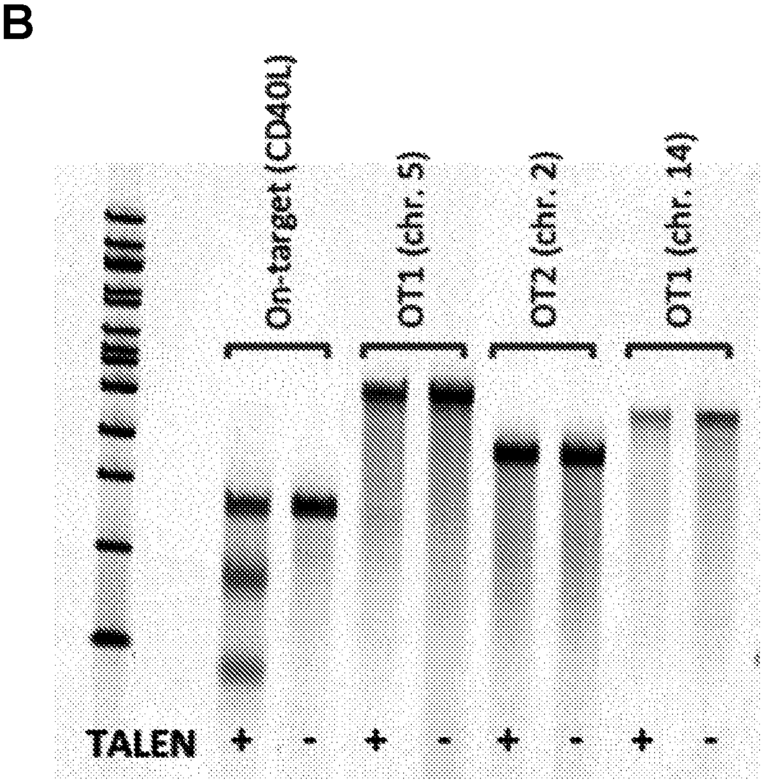
*Fig. 11*

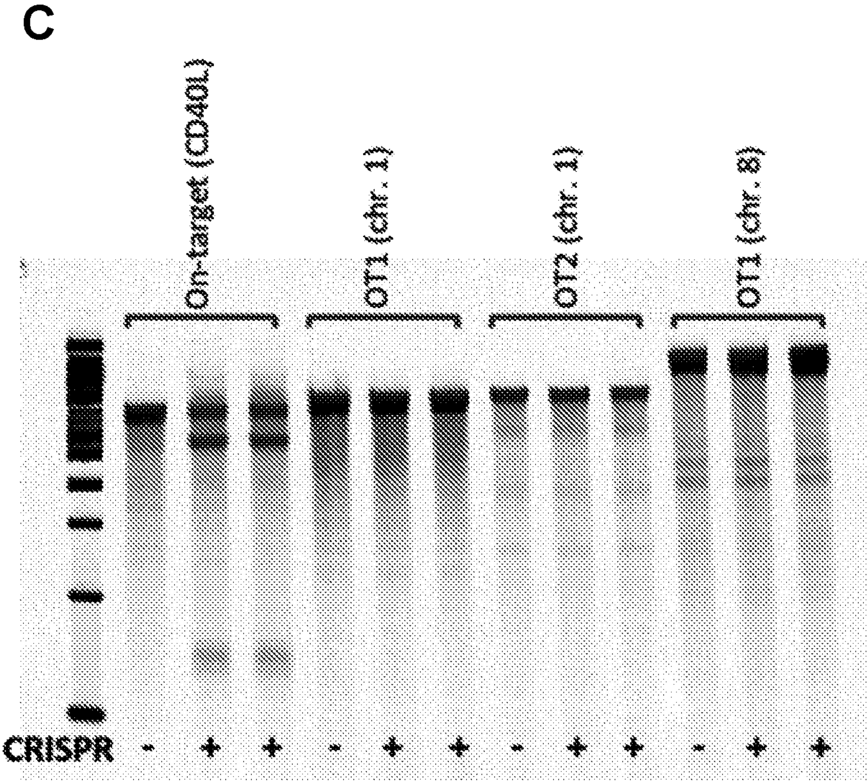
*Fig. 11, cont'd.*

A

| TAL1: GCCTCTGCCACCTTCTCTG<br>TAL2: CAACTTTAACACAGC | | | | |
|---|---|---|---|---|
| Site | chr | TALEN pair | | homology |
| CD40L | X | TAL1: ................... | TAL2: ............... | 100% |
| OT1 | 5 | TAL2: A.....AC....... | TAL2: .....G......... | 88.24% |
| OT2 | 2 | TAL1: ................A.T | TAL2: ATC............ | 82.35% |
| OT3 | 14 | TAL2: .....G......... | TAL2: A.....AC....... | 82.35% |

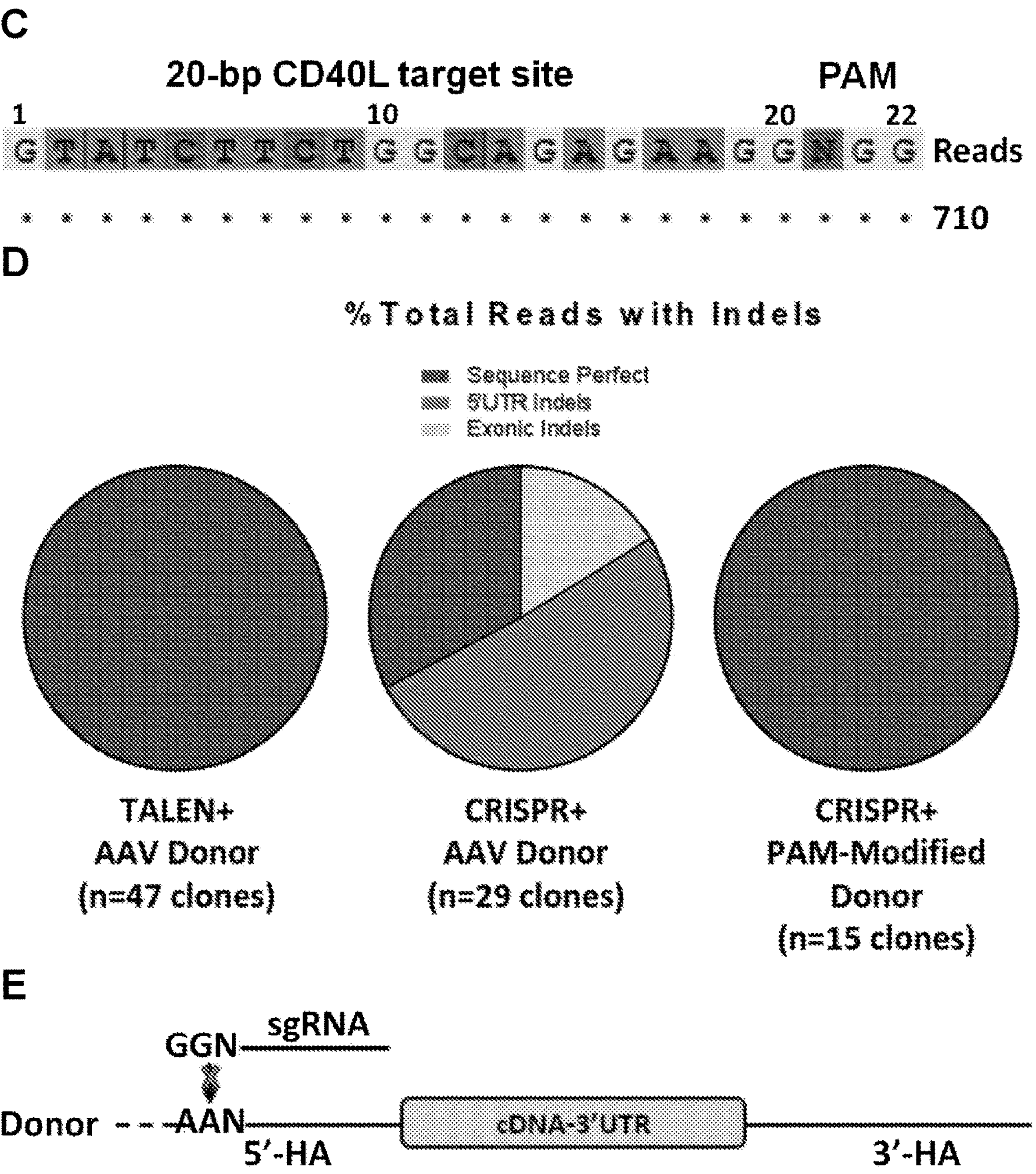
*Fig. 12, cont'd.*

Hyper-Immunoglobulin M Syndromes

Heterogenous group of genetic disorders resulting in defects of immunoglobulin class switch recombination +/- defects of somatic hypermutation (est incidence 1/500,000 males)

Clinical Presentation:

- Bacterial sinopulmonary infections
- Pneumonias
- Gastrointestinal infections

Concerns with HSCT

- Reactivation of chronic infections
- Worsening of pre-existing lung damage
- Graft-versus-host disease
- Unstandardized conditioning regimen and timing of transplant X-Linked Hyper IgM Syndrome – a sever primary immune deficiency.

XHIM is due to mutations of the CD40 ligand gene (*CD40LG aka CD154*) which drives B lymphocyte Ig class switching (IgM-> IgG) (and other things)

CD40LG is an excellent candidate for gene editing because:

(1) It requires precise and tight regulation of its expression ; and (2) There are many different mutations in different patients.

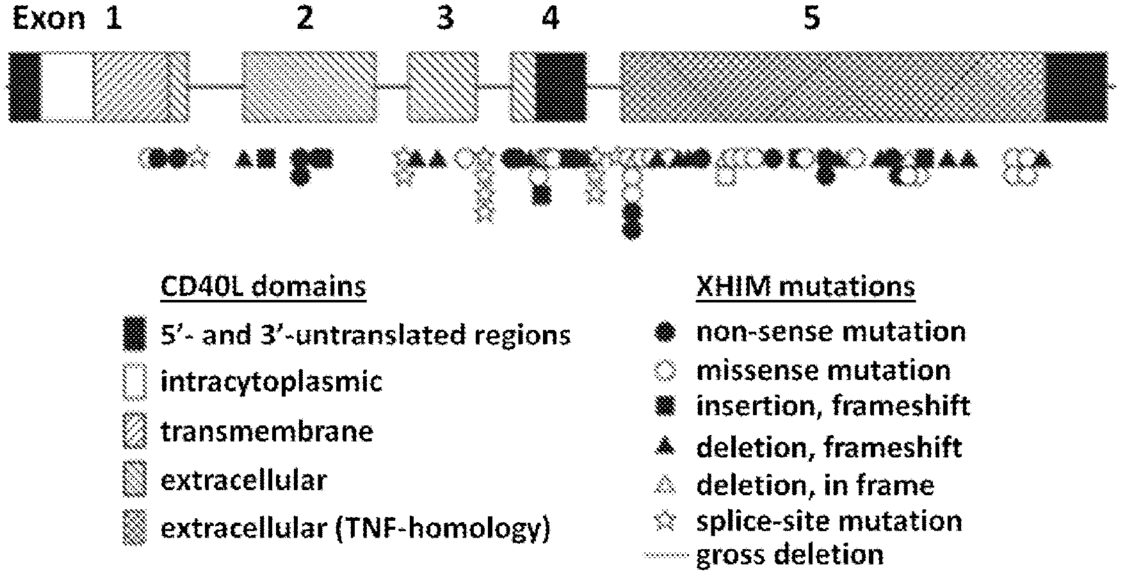

*Fig. 15*

CD40LG Gene Edited 1° XHIGM T Cells Bind rCD40uIg and Respond Physiologically to Stimulation

A

XHIM nano-Int4 Donor

5' homology arm:
CTTTACGTAACGTTTTTGCTGGGAGAGAAGACTACGAAGCACATTTTCCAGGAAGTGTGGGCTGCAACG
ATTGTGCGCTCTTAACTAATCCTGAGTAAGGTGGCCACTTTGACAGTCTTCTCATGCTGCCTCTGCCACCT
TCTCTGCCAGAAGATACCATTTCAACTTTAACACAGC

Exon 1 (endogenous sequence):
ATGATCGAAACATACAACCAAACTTCTCCCCGATC

Codon optimized cDNA (exons 1-4):
CGCCGCCACAGGCCTGCCTATCAGCATGAAGATCTTTATGTACCTGCTGACCGTGTTCCTGATCACCCAG
ATGATCGGCAGCGCCCTGTTCGCCGTGTACCTGCACAGACGGCTGGACAAGATCGAGGACGAGCGGAA
CCTGCACGAGGACTTCGTGTTCATGAAGACCATCCAGCGGTGCAACACCGGCGAGAGAAGCCTGAGCC
TGCTGAACTGCGAGGAAATCAAGAGCCAGTTCGAGGGCTTCGTGAAGGACATCATGCTGAACAAAGAG
GAAACTAAGAAAGAAAACAGCTTCGAGATGCAGAAGGGCGACCAGAACCCCCAGATTGCCGCCCACGT
GATCAGCGAGGCCAGCAGCAAGACCAC

Intron 4 (Nano):
AtctgGTAAGTCACACAGCATCTGAGCGGTAGCCACCCAAGGGGAAAGGCTGGGATGCCGGATCTTGTG
CCCTGATAGACCTAAGACTATCGAATAGGAATTATTTTTTAAAAAGCTCAAGGAAGCAAACACATCAGTA
CTTTCACTTTTCCTCAACCCTCACCCCCATCAGTCAGTCTAGCTTTCTGTGGGAGCTGAGATTTCAAGTCG
GGTGCACACACTACTTTGAACCCACTCAACATCTCAGCCGAGAAAATGGCACACTGTTGGTGGGTACTCT
GGCTTAGCCACAAGAATACTGGTACTTTCAAGTTGGTGGCGCCCACTACAATGGGAGATCAAAACATAC
CGTGAAATGAGCACACAGTTTATTTTCATACTTCCTTGCCTAATTTTAGTCCTTGCTGGGGGAGGCAGAT
CAGGTTTGCAACAGTTGTCAGAATGTGAACCATGCTCTGCTTCACCTCACCACAAACTTTCCCTTTCTTTG
TAACAGtgtta

Codon optimized cDNA (exon 5):
CAGTGGGCCGAGAAGGGCTACTACACCATGAGCAACAACCTCGTGACCCTGGAAAACGGCAAGCAGCT
GACAGTGAAGCGGCAGGGCCTGTACTACATCTACGCCCAAGTGACCTTCTGCAGCAACAGAGAGGCCA
GCTCCCAGGCCCCCTTTATCGCCAGCCTGTGCCTGAAGTCCCCCGGCAGATTCGAGAGAATCCTGCTGAG
AGCCGCCAACACCCACAGCAGCGCCAAGCCTTGTGGCCAGCAGTCTATCCACCTGGGCGGCGTGTTCGA
ACTGCAGCCTGGCGCCTCCGTGTTCGTGAACGTGACCGATCCTAGCCAGGTGTCCCACGGCACCGGCTT
CACAAGCTTCGGACTGCTGAAGCTGTGA

XHIM nano-Int4 Donor, cont'd.

CD40L 3'UTR:

ACAGTGTCACCTTGCAGGCTGTGGTGGAGCTGACGCTGGGAGTCTTCATAATACAGCACAGCGGTTAAG
CCCACCCCCTGTTAACTGCCTATTTATAACCCTAGGATCCTCCTTATGGAGAACTATTTATTATACACTCCA
AGGCATGTAGAACTGTAATAAGTGAATTACAGGTCACATGAAACCAAAACGGGCCCTGCTCCATAAGAG
CTTATATATCTGAAGCAGCAACCCCACTGATGCAGACATCCAGAGAGTCCTATGAAAAGACAAGGCCAT
TATGCACAGGTTGAATTCTGAGTAAACAGCAGATAACTTGCCAAGTTCAGTTTTGTTTCTTTGCGTGCAG
TGTCTTTCCATGGATAATGCATTTGATTTATCAGTGAAGATGCAGAAGGGAAATGGGGAGCCTCAGCTC
ACATTCAGTTATGGTTGACTCTGGGTTCCTATGGCCTTGTTGGAGGGGGCCAGGCTCTAGAACGTCTAA
CACAGTGGAGAACCGAAACCCCCCCCCCCCCCGCCACCCTCTCGGACAGTTATTCATTCTCTTTCAATCTC
TCTCTCTCCATCTCTCTCTTTCAGTCTCTCTCTCTCAACCTCTTTCTTCCAATCTCTCTTTCTCAATCTCTCTGT
TTCCCTTTGTCAGTCTCTTCCCTCCCCCAGTCTCTCTTCTCAATCCCCCTTTCTAACACACACACACACACAC
ACACACACACACACACACACACACACACACACAGAGTCAGGCCGTTGCTAGTCAGTTCTCTTCTTTCCAC
CCTGTCCCTATCTCTACCACTATAGATGAGGGTGAGGAGTAGGGAGTGCAGCCCTGAGCCTGCCCACTC
CTCATTACGAAATGACTGTATTTAAAGGAAATCTATTGTATCTACCTGCAGTCTCCATTGTTTCCAGAGTG
AACTTGTAATTATCTTGTTATTTATTTTTTGAATaataaagacctcttaacattatcg

3' Homology Arm:

TGCGGCCACTGGACTGCCCATCAGCATGAAAATTTTTATGTATTTACTTACTGTTTTTCTTATCACCCAGAT
GATTGGGTCAGCACTTTTTGCTGTGTATCTTCATAGAAGGTTGGACAAGGTAAGATGAACCACAAGCCTT
TATTAACTAAATTTGGGGTCCTTACTAATTCATAGGTTGGTTCTACCCAAATGATGGATGATGGTAGAAA
CCAAATAGAAGAATGGTCTTGTGGCATAATGTTTGTTGCCTAGTCAATGAAGTCTCATATTCTTGTCTCTG
GTTAGGATCTTGGGATCTGGAGTCAGACTGCCTGGGTTCAAATCTTGGCTCTGCCCATACCATCTCTGTT
ATCCTGGGGCAAGTGCCTCAGTTTCCACATCTGAGAAATGGGGATGGTATTGGTGTCCATTTCATAGATT
AAGTGAGTTTAGCCTTGTAAAAAGCTT

XHIM micro-Int4 Donor

5' Homology Arm:
CTTTACGTAACGTTTTTGCTGGGAGAGAAGACTACGAAGCACATTTTCCAGGAAGTGTGGGCTGCAACG
ATTGTGCGCTCTTAACTAATCCTGAGTAAGGTGGCCACTTTGACAGTCTTCTCATGCTGCCTCTGCCACCT
TCTCTGCCAGAAGATACCATTTCAACTTTAACACAGC Exon 1 (endogenous sequence):
ATGATCGAAACATACAACCAAACTTCTCCCCGATC Codon optimized cDNA (exons 1-4):
CGCCGCCACAGGCCTGCCTATCAGCATGAAGATCTTTATGTACCTGCTGACCGTGTTCCTGATCACCCAG
ATGATCGGCAGCGCCCTGTTCGCCGTGTACCTGCACAGACGGCTGGACAAGATCGAGGACGAGCGGAA
CCTGCACGAGGACTTCGTGTTCATGAAGACCATCCAGCGGTGCAACACCGGCGAGAGAAGCCTGAGCC
TGCTGAACTGCGAGGAAATCAAGAGCCAGTTCGAGGGCTTCGTGAAGGACATCATGCTGAACAAAGAG
GAAACTAAGAAAGAAAACAGCTTCGAGATGCAGAAGGGCGACCAGAACCCCCAGATTGCCGCCCACGT
GATCAGCGAGGCCAGCAGCAAGACCAC

Intron 4 (Micro):
atctgGTAAGTCACACAGCATCTGAGCGGTAGCCACCCAAGGGGAAAGGCTGGGATGCCGAAGTCATGT
TACCTAATGGTTAAACTCCTCTTTTCCCCTGGGACCCAATTTACAAACCTACCCCTACAGTAAAGGGCGA
GTCTTACCAGGTGGGATCTTGTGCCCTGATAGACCTAAGACTATCGAATAGGAATTATTTTTTAAAAAGC
TCAAGGAAGCAAACACATCAGTACTTTCACTTTTCCTCAACCCTCACCCCCATCAGTCAGTCTAGCTTTCT
GTGGGAGCTGAGATTTCAAGTCGGGTGCACACACTACTTTGAACCCACTCAACATCTCAGCCGAGAAAA
TGGCACACTGTTGGTGGGTACTCTGGCTTAGCCACAAGAATACTGGTACTTTCAAGTTGGTGGCGCCCA
CTACAATGGGAGATCAAAACATACCGTGAAATGAGCACACAGTTTATTTTCATACTTCCTTGCCTAATTTT
AGTCCTTGCTGGGGGAGGCAGATCAGGTTTGCAACAGCATGATCAGGTAGGAAGAAATGGGGTCTTTT
CTCTGTGCTGAGGCTGAGCTAGGTAGACTGACAACTCTCTGACTTTGTAAAATTCAAGGCAAGCAAGGT
ATTCATGGTAATATTAGCAAAAATTTGGTCCGAGTAATTTGGTATGTATAATTTATGATGTCAAATTTTGA
AATCATTTGTGCCTTCTTAAGTTCAAGGCAAATTGGCTATAAGAACTCTAACGAGAGAAAGAAACTCACT
GTGATCTCTTACTTTATTTAATCTTCACAAGTCTCTGAAATATGCTCCAATATGAGCCCCGTGTTGCAGAT
GAGGAACTGAAGCTCATGGAGATTTAGAGACTTGCCCAAGCTTAAATAGAGCCTAGATTGGAACATGG
CTCTGTCTGACTCTGAAGCCCATGGAAGGGGCCTTGAGAATCCATCCCTATACAAAGCCAATATCCAACA
TTAAACTATATTTTTTGTCAGAATGTGAACCATGCTCTGCTTCACCTCACCACAAACTTTCCCTTTCTTTGT
AACAGtgtta

Codon optimized cDNA (exon 5):
CAGTGGGCCGAGAAGGGCTACTACACCATGAGCAACAACCTCGTGACCCTGGAAAACGGCAAGCAGCT
GACAGTGAAGCGGCAGGGCCTGTACTACATCTACGCCCAAGTGACCTTCTGCAGCAACAGAGAGGCCA
GCTCCCAGGCCCCCTTTATCGCCAGCCTGTGCCTGAAGTCCCCCGGCAGATTCGAGAGAATCCTGCTGAG
AGCCGCCAACACCCACAGCAGCGCCAAGCCTTGTGGCCAGCAGTCTATCCACCTGGGCGGCGTGTTCGA
ACTGCAGCCTGGCGCCTCCGTGTTCGTGAACGTGACCGATCCTAGCCAGGTGTCCCACGGCACCGGCTT
CACAAGCTTCGGACTGCTGAAGCTGTGA

XHIM micro-Int4 Donor, cont'd.

CD40L 3'UTR:
ACAGTGTCACCTTGCAGGCTGTGGTGGAGCTGACGCTGGGAGTCTTCATAATACAGCACAGCGGTTAAG
CCCACCCCCTGTTAACTGCCTATTTATAACCCTAGGATCCTCCTTATGGAGAACTATTTATTATACACTCCA
AGGCATGTAGAACTGTAATAAGTGAATTACAGGTCACATGAAACCAAAACGGGCCCTGCTCCATAAGAG
CTTATATATCTGAAGCAGCAACCCCACTGATGCAGACATCCAGAGAGTCCTATGAAAAGACAAGGCCAT
TATGCACAGGTTGAATTCTGAGTAAACAGCAGATAACTTGCCAAGTTCAGTTTTGTTTCTTTGCGTGCAG
TGTCTTTCCATGGATAATGCATTTGATTTATCAGTGAAGATGCAGAAGGGAAATGGGGAGCCTCAGCTC
ACATTCAGTTATGGTTGACTCTGGGTTCCTATGGCCTTGTTGGAGGGGGCCAGGCTCTAGAACGTCTAA
CACAGTGGAGAACCGAAACCCCCCCCCCCCCCGCCACCCTCTCGGACAGTTATTCATTCTCTTTCAATCTC
TCTCTCTCCATCTCTCTCTTTCAGTCTCTCTCTCTCAACCTCTTTCTTCCAATCTCTCTTTCTCAATCTCTCTGT
TTCCCTTTGTCAGTCTCTTCCCTCCCCCAGTCTCTCTTCTCAATCCCCCTTTCTAACACACACACACACACAC
ACACACACACACACACACACACACACACACACAGAGTCAGGCCGTTGCTAGTCAGTTCTCTTCTTTCCAC
CCTGTCCCTATCTCTACCACTATAGATGAGGGTGAGGAGTAGGGAGTGCAGCCCTGAGCCTGCCCACTC
CTCATTACGAAATGACTGTATTTAAAGGAAATCTATTGTATCTACCTGCAGTCTCCATTGTTTCCAGAGTG
AACTTGTAATTATCTTGTTATTTATTTTTTGAATaataaagacctcttaacattatcg

3' Homology Arm:
TGCGGCCACTGGACTGCCCATCAGCATGAAAATTTTTATGTATTTACTTACTGTTTTTCTTATCACCCAGAT
GATTGGGTCAGCACTTTTTGCTGTGTATCTTCATAGAAGGTTGGACAAGGTAAGATGAACCACAAGCCTT
TATTAACTAAATTTGGGGTCCTTACTAATTCATAGGTTGGTTCTACCCAAATGATGGATGATGGTAGAAA
CCAAATAGAAGAATGGTCTTGTGGCATAATGTTTGTTGCCTAGTCAATGAAGTCTCATATTCTTGTCTCTG
GTTAGGATCTTGGGATCTGGAGTCAGACTGCCTGGGTTCAAATCTTGGCTCTGCCCATACCATCTCTGTT
ATCCTGGGGCAAGTGCCTCAGTTTCCACATCTGAGAAATGGGGATGGTATTGGTGTCCATTTCATAGATT
AAGTGAGTTTAGCCTTGTAAAAAGCTT

*Fig. 25, cont'd.*

GENE EDITING OF MONOGENIC DISORDERS IN HUMAN HEMATOPOIETIC STEM CELLS—CORRECTION OF X-LINKED HYPER-IGM SYNDROME (XHIM)

CROSS-REFERENCE TO RELATED APPLICATIONS

This application is a U.S. 371 National Phase of PCT/US2019/034713, filed May 30, 2019, which claims priority to and benefit of U.S. Ser. No. 62/678,218, filed on May 30, 2018, and U.S. Ser. No. 62/760,448, filed on Nov. 13, 2018, all of which are incorporated herein by reference in their entirety for all purposes.

SEQUENCE LISTING STATEMENT

This application contains references to nucleic acid sequences submitted as the sequence listing text file "P-633491-US1_ST25_08_27_2025.txt", file size 29,600 bytes, created on Aug. 27, 2025, which is incorporated by reference in its entirety pursuant to 37 C.F.R. § 1.52(e)(5).

BACKGROUND

X-linked hyper-IgM syndrome (XHIM) is a primary immunodeficiency characterized by the absence of IgG, IgA, and IgE with normal to elevated IgM resulting from defects in the CD40LG gene that encodes CD40 ligand (CD40L) expressed on the surface of activated T lymphocytes. CD40L binds to CD40 on B lymphocytes and is essential in the interaction between T and B cells that induces class switch recombination of the immunoglobulin heavy chain gene. Without proper CD40L expression, affected individuals are profoundly susceptible to bacterial and opportunistic infections with a propensity for autoimmunity and malignancies (see, e.g., Hayward et al. (1997) *J. Immunol.,* 158(2):977-983; Levy et al. (1997) *J. Pediatr.* 131(1 Pt 1): 47-54).

Long-term prognosis for XHIM remains poor with a median survival time of approximately 25 years from diagnosis (de la Morena et al. (2017) *J. Allergy Clin. Immunol.* 139(4): 1282-1292). Immunologic reconstitution with allogeneic hematopoietic stem cell transplant (HSCT) is a definitive treatment but has been associated with a high incidence of acute graft-versus-host disease (GvHD), hepatic sinusoidal obstruction syndrome, exacerbation of infections, and death (see, e.g., Gennery et al. (2014) *Blood,* 103: 1152-1157; Mitsui-Sekinaka et al. (2015) *J. Allergy Clin. Immunol.* 136(4): 1018-1024). Despite the curative nature of HSCT, there is no overall difference in survival between patients treated with or without HSCT, although those who undergo transplantation report improved general well-being as measured by Karnofsky/Lansky scores (de la Morena et al. supra.).

While gene addition of normal CD40L cDNA with constitutively expressed viral vectors can correct the immune deficiency in mouse models of XHIM, abnormal lymphoproliferation is a significant complication due to constitutive expression of the gene (Brown et al. (1998) *Nat Med.* 4(11): 1253-1260; Sacco et al. (2000) *Cancer Gene Ther.* 7(10): 1299-1306). This emphasizes the need for close regulation of CD40LG and that previous methods of gene therapy through non-regulated gene addition may not be safe in humans. In addition, efforts to create viral vectors that an express the CD40L gene in a physiologically regulated manner have not been successful (Romero et al. (2011) *Gene Therapy,* 18: 364-371). Retroviral vectors also pose a significant risk of insertional oncogenesis, emphasizing the need for other therapeutic options.

SUMMARY

As an alternative to uncontrolled, viral-mediated gene addition, targeted gene correction and in-frame-targeted gene addition that utilizes the endogenous promoter represents a major advancement in gene therapy. The discovery of meganucleases in the mid-1990's (e.g., Sce-I) marked the beginning of using endonucleases that could create double-strand breaks and promote homologous recombination by almost five orders of magnitude (Epinat et al. (2003) *Nucleic Acids Res.* 31: 2952-2962; Porteus & Baltimore (2003) *Science,* 300(5620): 763), and in the last decade, there has been a bloom in gene editing technologies, led by Zinc Finger Nucleases, Transcription Activator-Like Effector Nucleases (TALENs) and the Clustered Regularly Interspaced Short Palindromic Repeats (CRISPR)-associated protein 9 (Cas9) system with its ease of use and nearly limitless DNA sequences that can be targeted (Cong et al. (2013) *Science,* 339(6121): 819-823).

Although ideally 100% of XHIM hematopoietic stem cells (HSC) would be gene-corrected, only a low frequency of expression is sufficient to correct the immunodeficiencies in mice (Brown et al. (1998) supra.). In humans, female carriers who have X-inactivation in hematopoietic lineages that is skewed towards expression of the defective CD40LG are asymptomatic at even very low frequencies (12%) of peripheral blood mononuclear cells (PBMC) expressing CD40L (Hollenbaugh et al. (1994) *Clin Invest.* 94: 616-622). These data delineate a very feasible goal for gene correction frequencies that can result in significant clinical improvement or cure of these diseases.

As described herein, both TALEN and CRISPR/Cas9 platforms were used to achieve targeted insertion of a normal human CD40L cDNA at the CD40LG gene locus in both differentiated human T lymphocytes as well as CD34+ hematopoietic stem/progenitor cells (HSPC) at frequencies that exceed this goal.

Accordingly, various embodiments contemplated herein may include, but need not be limited to, one or more of the following:

Embodiment 1: A method of treating X-Linked Hyper-IgM Syndrome (XHIM) in a mammal, said method comprising:

- providing differentiated T cells and/or stem/progenitor cells from said mammal;
- performing a targeted insertion of a corrective CD40L cDNA at the CD40LG gene locus in said cells to provide a corrected CD40LG gene wherein said targeted insertion places said corrective CD40L cDNA downstream and operably linked to the endogenous CD40LG enhancer/promoter; and
- introducing said cells into said mammal where said corrected CD40LG gene is expressed in a physiologically regulated manner.

Embodiment 2: The method of embodiment 1, wherein said performing a targeted insertion comprises: transducing said cells with an AAV vector or a lentiviral vector containing a donor comprising a corrective CD40L cDNA flanked by homology arms; and transfecting said cells in vitro, with: a TALEN protein or a TALEN mRNA targeting the CD40L 5' UTR; or a nucleic acid encoding a guide RNA (gRNA) and CRISPR/Cas endonuclease where said gRNA targets the CD40L 5' UTR; or a ribonucleoprotein (RNP) complex comping a guide RNA complexed to a CRISPR/Cas endonuclease, where said gRNA targets the CD40L 5' UTR.

Embodiment 3: The method of embodiment 2, wherein said corrective CD40L cDNA comprises all or a portion of a corrected CD40L gene and comprises all or a portion or the 3' UTR of the CD40 L gene wherein said portion of the 3' UTR is sufficient to allow binding of a polypyrimidine track binding protein (PTB) to said 3' UTR.

Embodiment 4: The method of embodiment 3, wherein said corrective CD40L cDNA comprises all five exons (785 bp) along with the 3' UTR (944 bp) of the human CD40LG gene.

Embodiment 5: The method of embodiment 4, wherein said 3' UTR is followed by the bGH polyA signal (24 bp).

Embodiment 6: The method according to any one of embodiments 2-5, wherein said cDNA donor sequence is flanked by a 5' homology arm that begins at the TALEN or CRISPR/Cas cut site and extends at least 100 bp upstream.

Embodiment 7: The method of embodiment 6, wherein said 5' homology arm extends 162 bp upstream from said cut site.

Embodiment 8: The method of embodiment 6, wherein said 5' homology arm extends 177 bp upstream from said cut site.

Embodiment 9: The method according to any one of embodiments 2-8, wherein said cDNA donor sequence is flanked by a 3' homology arm that extends at least 200 bp, or at least 300 bp, or at least 350 bp, or at least 400 bp downstream of the TALEN or CRISPR/Cas cut site.

Embodiment 10: The method of embodiment 9, wherein said cDNA donor sequence is flanked by a 3' homology arm that extends 405 bp downstream of the TALEN or CRISPR/Cas cut site.

Embodiment 11: The method of embodiment 9, wherein said cDNA donor sequence is flanked by a 3' homology arm that extends 450 bp downstream of the TALEN or CRISPR/Cas cut site.

Embodiment 12: The method according to any one of embodiments 2-11, wherein said cDNA donor is codon-optimized/-divergent.

Embodiment 13: The method according to any one of embodiments 2-12, wherein said cDNA donor is modified to exclude protospacer adjacent motifs (PAMs).

Embodiment 14: The method according to any one of embodiments 2-13, wherein said cDNA is modified by modifying a PAM sequence TGG to TAA.

Embodiment 15: The method of embodiment 3, wherein said donor comprises a codon-optimized cDNA donor that includes about a region of intron 4 between exons 4 and 5 containing a DNase I hypersensitivity cluster and is flanked by the endogenous intron 4 splice machinery which includes a 5' splice donor and a 3' splice acceptor preceded by the branch point and AG exclusion zone.

Embodiment 16: The method of embodiment 15, wherein said donor comprises a 1058 bp region of intron 4.

Embodiment 17: The method of embodiment 16, wherein said donor comprises the intron 4 (micro) (SEQ ID NO:11).

Embodiment 18: The method of embodiment 15, wherein said donor comprises a 501 bp region of intron 4.

Embodiment 19: The method of embodiment 18, wherein said donor comprises the intron 4 (nano).

Embodiment 20: The method according to any one of embodiments 15-19, wherein said donor comprises Exon 1 (endogenous sequence) (SEQ ID NO:4), codon optimized cDNA (exons 1-4) (SEQ ID NO:5), codon optimized cDNA (exon 5) (SEQ ID NO:7), and CD40L 3'UTR (SEQ ID NO:8).

Embodiment 21: The method according to any one of embodiments 15-20, wherein said donor comprises a 5' Homology Arm (SEQ ID NO:3).

Embodiment 22: The method according to any one of embodiments 15-21, wherein said donor comprises a and 3' Homology Arm.

Embodiment 23: The method of embodiment 15, wherein said donor comprises or consists of the XHIM micro-Int4 Donor (SEQ ID NO:11).

Embodiment 24: The method of embodiment 15, wherein said donor comprises or consists of the XHIM nano-Int4 Donor (SEQ ID NO:9)

Embodiment 25: The method according to any one of embodiments 1-24, wherein said method comprises transducing said cells with a lentiviral vector containing said donor comprising a corrective CD40L cDNA flanked by homology arms.

Embodiment 26: The method of embodiment 25, wherein said lentiviral vector comprises an integrase-deficient lentivirus (IDLV).

Embodiment 27: The method according to any one of embodiments 1-24, wherein said method comprises transducing said cells with an AAV vector containing said donor comprising a corrective CD40L cDNA flanked by homology arms.

Embodiment 28: The method of embodiment 27, wherein said AAV vector wherein said AAV vector comprises a serotype selected from the group consisting of AAV1, AAV2, AAV4, AAV5, AAV6, AAV8, and AAV9.

Embodiment 29: The method of embodiment 28, wherein said AAV vector comprises an AAV6 serotype.

Embodiment 30: The method according to any one of embodiments 27-29, wherein an AAV helper protein is introduced into said cells.

Embodiment 31: The method of embodiment 30, wherein said AAV helper protein is introduced into said cell by transfection with an mRNA expressing said AAV helper protein.

Embodiment 32: The method of embodiment 31, wherein said AAV helper protein comprises a mutant adenoviral serotype 5 helper protein.

Embodiment 33: The method of embodiment 32, wherein said helper proteins comprise E4orf6 and/or Elb55k helper proteins.

Embodiment 34: The method according to any one of embodiments 1-33, wherein said method comprises transfecting said cells in vitro, with TALEN mRNA targeting the CD40L 5'UTR.

Embodiment 35: The method of embodiment 34, wherein said TALEN mRNA encodes a TALEN pair characterized by the binding sites selected from the group consisting of TALEN1, TALEN2, and TALEN3 as shown in FIG. 1, panel A.

Embodiment 36: The method of embodiment 35, wherein said TALEN mRNA encodes a TALEN pair characterized by the TALEN 2 binding sites.

Embodiment 37: The method according to any one of embodiments 1-33, wherein said method comprises transfecting said cells in vitro, with a nucleic acid encoding a guide RNA (gRNA) and CRISPR/Cas endonuclease where said gRNA targets the CD40L 5'UTR.

Embodiment 38: The method according to any one of embodiments 1-33, wherein said method comprises transfecting said cells in vitro, with a ribonucleoprotein (RNP) complex comping a guide RNA complexed to a CRISPR/Cas endonuclease.

Embodiment 39: The method according to any one of embodiments 37-38, wherein said gRNA comprises the sequence 5'-GTATCTTCTGGCAGAGAAGG-3' (SEQ ID NO:12).

Embodiment 40: The method according to any one of embodiments 37-39, wherein said donor comprises the sequence of SEQ ID NO:13.

Embodiment 41: The method according to any one of embodiments 37-40, wherein said CRISPR/Cas endonuclease comprises a class 2 CRISPR/Cas endonuclease and a guide RNA.

Embodiment 42: The method of embodiment 41, wherein said class 2 CRISPR/Cas endonuclease is a type II CRISPR/Cas endonuclease.

Embodiment 43: The method according to any one of embodiments 41-42, wherein the class 2 CRISPR/Cas endonuclease is a Cas9 polypeptide and the corresponding CRISPR/Cas guide RNA is a Cas9 guide RNA.

Embodiment 44: The method of embodiment 43, wherein said Cas9 protein is selected from the group consisting of a *Streptococcus pyogenes* Cas9 protein (spCas9) or a functional portion thereof, a *Staphylococcus aureus* Cas9 protein (saCas9) or a functional portion thereof, a *Streptococcus thermophilus* Cas9 protein (stCas9) or a functional portion thereof, a *Neisseria meningitides* Cas9 protein (nmCas9) or a functional portion thereof, and a *Treponema denticola* Cas9 protein (tdCas9) or a functional portion thereof.

Embodiment 45: The method of embodiment 44, wherein said Cas9 protein comprises a *Streptococcus pyogenes* Cas9 protein (spCas9).

Embodiment 46: The method of embodiment 44, wherein said Cas9 protein comprises a *Staphylococcus aureus* Cas9 protein (saCas9).

Embodiment 47: The method of embodiment 44, wherein said Cas9 protein comprises a *Streptococcus thermophilus* Cas9 protein.

Embodiment 48: The method of embodiment 44, wherein said Cas9 protein comprises a *Neisseria meningitides* Cas9 protein (nmCas9).

Embodiment 49: The method of embodiment 44, wherein said Cas9 protein comprises a *Treponema denticola* Cas9 protein (tdCas9).

Embodiment 50: The method according to any one of embodiments 37-40, wherein the class 2 CRISPR/Cas endonuclease is a type V or type VI CRISPR/Cas endonuclease.

Embodiment 51: The method of embodiment 50, wherein the class 2 CRISPR/Cas endonuclease is selected from the group consisting of a Cpf1 polypeptide or a functional portion thereof, a C2c1 polypeptide or a functional portion thereof, a C2c3 polypeptide or a functional portion thereof, and a C2c2 polypeptide or a functional portion thereof.

Embodiment 52: The method of embodiment 51, wherein the class 2 CRISPR/Cas endonuclease comprises a Cpf1 polypeptide.

Embodiment 53: The method according to any one of embodiments 37-52, wherein said guide RNA (gRNA) targets a region within the CD40L 5'UTR bracketed by binding sites for a TALEN pair selected from the group consisting of TALEN1, TALEN2, and TALEN3.

Embodiment 54: The method of embodiment 53, wherein said guide RNA (gRNA) targets a region within the CD40L 5'UTR bracketed by binding sites for TALEN2.

Embodiment 55: The method of embodiment 54, wherein said guide RNA (gRNA) targets a region within the CD40L 5'UTR illustrated by the gRNA shown in FIG. 5, panel A.

Embodiment 56: The method according to any one of embodiments 1-55, wherein said cells comprise hematopoietic stem and progenitor cells (HSPC).

Embodiment 57: The method of embodiment 56, wherein said cells comprise CD34+ hematopoietic stem and progenitor cells (HSPC).

Embodiment 58: The method according to any one of embodiments 1-55, wherein said cells comprise peripheral blood stem cells (PBSC).

Embodiment 59: The method of embodiment 58, wherein said cells comprise G-CSF mobilized peripheral blood stem cells (PBSC).

Embodiment 60: The method according to any one of embodiments 58-59, wherein said cells comprise CD34+ cells.

Embodiment 61: The method according to any one of embodiments 2-60, wherein said transfecting comprises a method selected from the group consisting of electroporation, sonoporation, lipofection, and transfection using cationic polymer.

Embodiment 62: The method of embodiment 61, wherein said transfecting comprises electroporation.

Embodiment 63: The method according to any one of embodiments 1-62, wherein said mammal is a human.

Embodiment 64: A system for the treatment of X-Linked Hyper-IgM Syndrome ((XHIM) in a mammal, said system comprising:

- a first component comprising an AAV vector or a lentiviral vector containing a donor comprising a corrective CD40L cDNA flanked by homology arms; and
- a second component comprising one or more of the following:
  - a TALEN mRNA targeting the CD40L 5' UTR; or
  - a nucleic acid encoding a guide RNA (gRNA) and CRISPR/Cas endonuclease where said gRNA targets the CD40L 5' UTR; or
  - a ribonucleoprotein (RNP) complex comping a guide RNA complexed to a CRISPR/Cas endonuclease, where said gRNA targets the CD40L 5' UTR.

Embodiment 65: The system of embodiment 64, wherein said corrective CD40L cDNA comprises all or a portion or the 3' UTR of the CD40 L gene wherein said portion of the 3' UTR is sufficient to allow binding of a polypyrimidine track binding protein (PTB) to said 3' UTR.

Embodiment 66: The system of embodiment 65, wherein said corrective CD40L cDNA comprises all five exons (785 bp) along with the 3' UTR (944 bp) of the human CD40LG gene.

Embodiment 67: The system of embodiment 66, wherein said 3' UTR is followed by the bGH polyA signal (24 bp).

Embodiment 68: The system according to any one of embodiments 64-67, wherein said cDNA donor sequence is flanked by a 5' homology arm that begins at the TALEN or CRISPR/Cas cut site and extends at least 100 bp upstream.

Embodiment 69: The system of embodiment 68, wherein said 5' homology arm extends 162 bp upstream from said cut site.

Embodiment 70: The system of embodiment 68, wherein said 5' homology arm extends 177 bp upstream from said cut site.

Embodiment 71: The system according to any one of embodiments 64-70, wherein said cDNA donor sequence is flanked by a 3' homology arm that extends at least 200 bp, or at least 300 bp, or at least 350 bp, or at least 400 bp downstream of the TALEN or CRISPR/Cas cut site.

Embodiment 72: The system of embodiment 71, wherein said cDNA donor sequence is flanked by a 3' homology arm that extends 405 bp downstream of the TALEN or CRISPR/Cas cut site.

Embodiment 73: The system of embodiment 71, wherein said cDNA donor sequence is flanked by a 3' homology arm that extends 450 bp downstream of the TALEN or CRISPR/Cas cut site.

Embodiment 74: The system according to any one of embodiments 64-73, wherein said cDNA donor is codon-optimized/-divergent.

Embodiment 75: The system according to any one of embodiments 64-74, wherein said cDNA donor modified to exclude protospacer adjacent motifs (PAMs).

Embodiment 76: The system according to any one of embodiments 64-75, wherein said cDNA is modified by modifying a PAM sequence TGG to TAA.

Embodiment 77: The system of embodiment 65, wherein said donor comprises a codon-optimized cDNA donor that includes about a region of intron 4 between exons 4 and 5 containing a DNase I hypersensitivity cluster and is flanked by the endogenous intron 4 splice machinery which includes a 5' splice donor and a 3' splice acceptor preceded by the branch point and AG exclusion zone.

Embodiment 78: The system of embodiment 77, wherein said donor comprises a 1058 bp region of intron 4.

Embodiment 79: The system of embodiment 78, wherein said donor comprises the intron 4 (micro) (SEQ ID NO:11).

Embodiment 80: The system of embodiment 77, wherein said donor comprises a 501 bp region of intron 4.

Embodiment 81: The system of embodiment 80, wherein said donor comprises the intron 4 (nano).

Embodiment 82: The system according to any one of embodiments 77-81, wherein said donor comprises Exon 1 (endogenous sequence) (SEQ ID NO:4), codon optimized cDNA (exons 1-4) (SEQ ID NO:5), codon optimized cDNA (exon 5) (SEQ ID NO:7), and CD40L 3'UTR (SEQ ID NO:8).

Embodiment 83: The system according to any one of embodiments 77-82, wherein said donor comprises a 5' Homology Arm (SEQ ID NO:3).

Embodiment 84: The system according to any one of embodiments 77-83, wherein said donor comprises a and 3' Homology Arm.

Embodiment 85: The system of embodiment 77, wherein said donor comprises or consists of the XHIM micro-Int4 Donor (SEQ ID NO:11).

Embodiment 86: The system of embodiment 77, wherein said donor comprises or consists of the XHIM nano-Int4 Donor (SEQ ID NO:9).

Embodiment 87: The system according to any one of embodiments 64-86, wherein said second component comprises a lentiviral vector containing said donor comprising a corrective CD40L cDNA flanked by homology arms.

Embodiment 88: The system of embodiment 87, wherein said lentiviral vector comprises an integrase-deficient lentivirus (IDLV).

Embodiment 89: The system according to any one of embodiments 64-86, wherein said second component t comprises an AAV vector containing said donor comprising a corrective CD40L cDNA flanked by homology arms.

Embodiment 90: The system of embodiment 89, wherein said AAV vector wherein said AAV vector comprises a serotype selected from the group consisting of AAV1, AAV2, AAV4, AAV5, AAV6, AAV8, and AAV9.

Embodiment 91: The system of embodiment 90, wherein said AAV vector comprises an AAV6 serotype.

Embodiment 92: The system according to any one of embodiments 89-91, wherein said system comprises a third component comprising an AAV helper protein or a nucleic acid encoding an AAV helper protein.

Embodiment 93: The system of embodiment 92, wherein said third component comprises an mRNA expressing said AAV helper protein.

Embodiment 94: The system of embodiment 93, wherein said AAV helper protein comprises a mutant adenoviral serotype 5 helper protein.

Embodiment 95: The system of embodiment 94, wherein said helper proteins comprise E4orf6 and/or Elb55k helper proteins.

Embodiment 96: The system according to any one of embodiments 64-76, wherein said second component comprises a TALEN mRNA targeting the CD40L 5'UTR.

Embodiment 97: The system of embodiment 96, wherein said TALEN mRNA encodes a TALEN pair characterized by the binding sites selected from the group consisting of TALEN1, TALEN2, and TALEN3 as shown in FIG. 1, panel A.

Embodiment 98: The system of embodiment 97, wherein said TALEN mRNA encodes a TALEN pair characterized by the TALEN 2 binding sites.

Embodiment 99: The system according to any one of embodiments 64-76, wherein said second component comprises a nucleic acid encoding a guide RNA (gRNA) and CRISPR/Cas endonuclease where said gRNA targets the CD40L 5'UTR.

Embodiment 100: The system according to any one of embodiments 64-76, wherein said second component comprises a ribonucleoprotein (RNP) complex comprising a guide RNA complexed to a CRISPR/Cas endonuclease.

Embodiment 101: The system according to any one of embodiments 99-100, wherein said gRNA comprises the sequence 5'-GTATCTTCTGGCAGAGAAGG -3' (SEQ ID NO:12).

Embodiment 102: The system according to any one of embodiments 99-101, wherein said donor comprises the sequence of SEQ ID NO:13.

Embodiment 103: The system according to any one of embodiments 99-102, wherein said CRISPR/Cas endonuclease comprises a class 2 CRISPR/Cas endonuclease and a guide RNA.

Embodiment 104: The system of embodiment 103, wherein said class 2 CRISPR/Cas endonuclease is a type II CRISPR/Cas endonuclease.

Embodiment 105: The system according to any one of embodiments 103-104, wherein the class 2 CRISPR/Cas endonuclease is a Cas9 polypeptide and the corresponding CRISPR/Cas guide RNA is a Cas9 guide RNA.

Embodiment 106: The system of embodiment 105, wherein said Cas9 protein is selected from the group consisting of a *Streptococcus pyogenes* Cas9 protein (spCas9) or a functional portion thereof, a *Staphylococcus aureus* Cas9 protein (saCas9) or a functional portion thereof, a *Streptococcus thermophilus* Cas9 protein (stCas9) or a functional portion thereof, a *Neisseria meningitides* Cas9 protein (nmCas9) or a functional portion thereof, and a *Treponema denticola* Cas9 protein (tdCas9) or a functional portion thereof.

Embodiment 107: The system of embodiment 106, wherein said Cas9 protein comprises a *Streptococcus pyogenes* Cas9 protein (spCas9).

Embodiment 108: The system of embodiment 106, wherein said Cas9 protein comprises a *Staphylococcus aureus* Cas9 protein (saCas9).

Embodiment 109: The system of embodiment 106, wherein said Cas9 protein comprises a *Streptococcus thermophilus* Cas9 protein.

Embodiment 110: The system of embodiment 106, wherein said Cas9 protein comprises a *Neisseria meningitides* Cas9 protein (nmCas9).

Embodiment 111: The system of embodiment 106, wherein said Cas9 protein comprises a *Treponema denticola* Cas9 protein (tdCas9).

Embodiment 112: The system according to any one of embodiments 99-102, wherein the class 2 CRISPR/Cas endonuclease is a type V or type VI CRISPR/Cas endonuclease.

Embodiment 113: The system of embodiment 112, wherein the class 2 CRISPR/Cas endonuclease is selected from the group consisting of a Cpf1 polypeptide or a functional portion thereof, a C2c1 polypeptide or a functional portion thereof, a C2c3 polypeptide or a functional portion thereof, and a C2c2 polypeptide or a functional portion thereof.

Embodiment 114: The system of embodiment 113, wherein the class 2 CRISPR/Cas endonuclease comprises a Cpf1 polypeptide.

Embodiment 115: The system according to any one of embodiments 99-114, wherein said guide RNA (gRNA) targets a region within the CD40L 5'UTR bracketed by binding sites for a TALEN pair selected from the group consisting of TALEN1, TALEN2, and TALEN3.

Embodiment 116: The system of embodiment 115, wherein said guide RNA (gRNA) targets a region within the CD40L 5' UTR bracketed by binding sites for TALEN2.

Embodiment 117: The system of embodiment 116, wherein said guide RNA (gRNA) targets a region within the CD40L 5' UTR illustrated by the gRNA shown in FIG. 5, panel A.

Embodiment 118: The system according to any one of embodiments 64-117, wherein said first component and second component, and third component when present, are disposed within a mammalian cell.

Embodiment 119: The system of embodiment 118, wherein said cell is a hematopoietic stem or progenitor cell (HSPC).

Embodiment 120: The system of embodiment 119, wherein said cell is a CD34+ hematopoietic stem or progenitor cell (HSPC).

Embodiment 121: The system of embodiment 120, wherein said cell is a peripheral blood stem cell (PBSC).

Embodiment 122: The system of embodiment 121, wherein said cell is a G-CSF mobilized peripheral blood stem cell (PBSC).

Embodiment 123: The system according to any one of embodiments 121-122, wherein said cell is a CD34+ cell.

Embodiment 124: The system according to any one of embodiment 118-123, wherein said cell is a human cell.

Embodiment 125: The system according to any one of embodiments 64-117, wherein said first component, second component, and when present, third component are components of a kit.

Embodiment 126: The system of embodiment 125, wherein each component is disposed within a container comprising said kit.

Embodiment 127: The system according to any one of embodiments 125-126, wherein said kit comprises instructional materials teaching the use of the components of a kit to insert a corrective cDNA into the CD40L gene.

Embodiment 128: A donor nucleic acid for the treatment of XHIM, said nucleic acid comprising all or a portion of a corrected CD40L gene and all or a portion or the 3' UTR of the CD40 L gene wherein said portion of the 3' UTR is sufficient to allow binding of a polypyrimidine track binding protein (PTB) to said 3' UTR.

Embodiment 129: The donor nucleic acid of embodiment 128, wherein said corrected CD40L gene comprises at least a portion that is codon optimized wherein said portion comprises Exon 1, and/or Exon 2, and/or Exon 3, and/or Exon 4, and/or Exon 5 and comprises all or a portion or the 3' UTR of the CD40 L gene wherein said portion of the 3' UTR is sufficient to allow binding of a polypyrimidine track binding protein (PTB) to said 3' UTR.

Embodiment 130: The donor nucleic acid of embodiment 128, wherein said corrective CD40L cDNA comprises all five exons (785 bp) along with the 3' UTR (944 bp) of the human CD40LG gene.

Embodiment 131: The donor nucleic acid of embodiment 130, wherein said 3' UTR is followed by the bGH polyA signal (24 bp).

Embodiment 132: The donor nucleic acid according to any one of embodiments 128-131, wherein said cDNA donor sequence is flanked by a 5' homology arm that begins at the TALEN or CRISPR/Cas cut site and extends at least 100 bp upstream.

Embodiment 133: The donor nucleic acid of embodiment 132, wherein said 5' homology arm extends 162 bp upstream from said cut site.

Embodiment 134: The donor nucleic acid of embodiment 132, wherein said 5' homology arm extends 177 bp upstream from said cut site.

Embodiment 135: The donor nucleic acid according to any one of embodiments 128-134, wherein said cDNA donor sequence is flanked by a 3' homology arm that extends at least 200 bp, or at least 300 bp, or at least 350 bp, or at least 400 bp downstream of the TALEN or CRISPR/Cas cut site.

Embodiment 136: The donor nucleic acid of embodiment 135, wherein said cDNA donor sequence is flanked by a 3' homology arm that extends 405 bp downstream of the TALEN or CRISPR/Cas cut site.

Embodiment 137: The donor nucleic acid of embodiment 135, wherein said cDNA donor sequence is flanked by a 3' homology arm that extends 450 bp downstream of the TALEN or CRISPR/Cas cut site.

Embodiment 138: The donor nucleic acid according to any one of embodiments 128-137, wherein said cDNA donor is codon-optimized/-divergent.

Embodiment 139: The donor nucleic acid according to any one of embodiments 128-138, wherein said cDNA donor is modified to exclude protospacer adjacent motifs (PAMs).

Embodiment 140: The donor nucleic acid according to any one of embodiments 128-139, wherein said cDNA is modified by modifying a PAM sequence TGG to TAA.

Embodiment 141: The donor nucleic acid of embodiment 128, wherein said donor comprises a codon-optimized cDNA donor that includes about a region of intron 4 between exons 4 and 5 containing a DNase I hypersensitivity cluster and is flanked by the endogenous intron 4 splice machinery which includes a 5' splice donor and a 3' splice acceptor preceded by the branch point and AG exclusion zone.

Embodiment 142: The donor nucleic acid of embodiment 141, wherein said donor comprises a 1058 bp region of intron 4.

Embodiment 143: The donor nucleic acid of embodiment 142, wherein said donor comprises the intron 4 (micro) (SEQ ID NO: 11).

Embodiment 144: The donor nucleic acid of embodiment 141, wherein said donor comprises a 450 to 550 bp region of intron 1, or a 501 bp region of intron 4.

Embodiment 145: The donor nucleic acid of embodiment 144, wherein said donor comprises the intron 4 (nano).

Embodiment 146: The donor nucleic acid according to any one of embodiments 141-145, wherein said donor comprises Exon 1 (endogenous sequence) (SEQ ID NO:4), codon optimized cDNA (exons 1-4) (SEQ ID NO:5), codon optimized cDNA (exon 5) (SEQ ID NO:7), and CD40L 3'UTR (SEQ ID NO:8).

Embodiment 147: The donor nucleic acid according to any one of embodiments 141-146, wherein said donor comprises a 5' Homology Arm (SEQ ID NO:3).

Embodiment 148: The donor nucleic acid according to any one of embodiments 141-147, wherein said donor comprises a and 3' Homology Arm).

Embodiment 149: The donor nucleic acid of embodiment 141, wherein said donor comprises or consists of the XHIM micro-Int4 Donor (SEQ ID NO:11).

Embodiment 150: The donor nucleic acid of embodiment 141, wherein said donor comprises or consists of the XHIM nano-Int4 Donor (SEQ ID NO:9).

Embodiment 151: A mammalian cell, wherein the genome of said cell comprises a corrected CD40L gene wherein said gene is modified to eliminate deleterious CD40L mutations.

Embodiment 152: The mammalian cell of embodiment 151, wherein said cell comprises all or a portion of a donor nucleic acid according to any one of embodiments 128-140.

Embodiment 153: The cell according to any one of embodiments 151-152, wherein said cell is a hematopoietic stem or progenitor cell (HSPC).

Embodiment 154: The cell of embodiment 153, wherein said cell is a CD34+ hematopoietic stem or progenitor cell (HSPC).

Embodiment 155: The cell according to any one of embodiments 151-152, wherein said cell is a peripheral blood stem cell.

Embodiment 156: The cell of embodiment 155, wherein said cell is a G-CSF mobilized peripheral blood stem cell (PBSC).

Embodiment 157: The cell according to any one of embodiments 155-156, wherein said cell is a CD34+ cells.

Definitions

The terms "subject," "individual," and "patient" may be used interchangeably and refer to humans, as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for a pathology described herein (e.g., XHIM).

The term "treat" when used with reference to treating, e.g., a pathology or disease refers to the mitigation and/or elimination of one or more symptoms of that pathology or disease, and/or a delay in the progression and/or a reduction in the rate of onset or severity of one or more symptoms of that pathology or disease, and/or the prevention of that pathology or disease. The term treat can refer to prophylactic treatment which includes a delay in the onset or the prevention of the onset of a pathology or disease.

A "host cell," as used herein, denotes an in vivo or in vitro eukaryotic cell, or a cell from a multicellular organism (e.g., a cell line) cultured as a unicellular entity, which eukaryotic cells can be, or have been, used as recipients for a nucleic acid (e.g., a donor template nucleic acid), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include, but are not limited to pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. Al. (1998) *Science,* 282(5391): 1145-1147) whereas induced pluripotent stem cells (iPSCs) are derived from somatic cells (Takahashi et. Al. (2007) Cell, 131(5): 861-872; Takahashi et. Al. (2007) *Nat. Protoc.* 2(12): 3081-3079; Yu et. Al. (2007) *Science,* 318(5858): 1917-1920). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein. In certain embodiments the methods described herein expressly exclude the use of embryonic stem cells or cells derived therefrom.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26al, TERT, and zfp42. Examples of methods of generating and characterizing iPSCs may be found in, for example, U.S. Patent Publication Nos. US20090047263, US20090068742, US20090191159, US20090227032, US20090246875, and US20090304646. Generally, to generate iPSCs, somatic cells are provided with reprogramming factors (e.g., Oct4, SOX2, KLF4, MYC, Nanog, Lin28, etc.) known in the art to reprogram the somatic cells to become pluripotent stem cells.

Hematopoietic stem cell transplantation (HSCT) is the transplantation of multipotent hematopoietic stem cells, usually derived from bone marrow, peripheral blood, or umbilical cord blood. In the methods described herein, the HSCT is typically autologous (the patient's own stem cells are used).

Peripheral blood stem cells (PBSCs) refers to hematopoietic stem and progenitor cells obtained from peripheral blood. Such cells are typically collected by apheresis or leukapheresis. The administered hematopoietic stem cells modified as described herein can be administered back into the subject where they then migrate to the recipient's bone marrow, a process known as stem cell homing. In In certain embodiments the PBSCs are "mobilized" by administration of G-CSF prior to collection of the cells.

As another illustrative example of cells that can be used in the methods described herein, hematopoietic stem cells (HSCs) can be harvested from the patient's bone marrow using well known techniques.

"CD34+ cells" refers to cells that display the CD34 antigen. CD34 is an antigen associated with hematopoietic stem cells, and isolation of CD34+ HSCs can readily be accomplished by well-known and clinically-validated methods. For example, a magnetic bead separation process that has been FDA-approved for use in various transplantation contexts is available commercially from Miltenyi Biotec, along with preparations for the handling and maintenance of such cells.

BRIEF DESCRIPTION OF THE DRAWINGS

FIG. 4, panels A-E. Viability and fold expansion of primary XHIM CD4 T cells after electroporation with TALEN mRNA and AAV6 cDNA transduction. Panel A) Viability and Panel B) Fold expansion of primary XHIM CD4 T cells treated with TALEN mRNA and AAV6 codon optimized cDNA donor. Panel C) Quantification of gene integration by ddPCR of T cells electroporated with TALEN mRNA and treated with a range of MOI of AAV6 cDNA donor. 24 hours after treatment, Panel D) viability and Panel E) fold expansion were measured by trypan blue (n=8-10 biological replicates). Bar graphs are presented as means±SD. Statistics were analyzed by Kruskal-Wallis test. NS=not significant.

FIG. 6, panels A-G, illustrates TALEN and CRISPR/Cas9 editing of the CD40L gene in primary human CD34+ peripheral blood stem cells (PBSC). Panel A) Gene integration rates in PBSC treated with TALEN mRNA and a CD40L cDNA AAV6 donor (n=8, 4 PBSC donor sources). Panel B) CD40L sequence (SEQ ID NO:2) binding sites and Panel C) allelic disruption rates measured by Surveyor nuclease assay of multiple CRISPR sgRNA targeting the CD40L 5'UTR in PBSC (n=8, 4 PBSC donor sources). Panel D) Gene integration rates of PBSC treated with CRISPR 3 gRNA co-electroporated with Cas9 mRNA or complexed to Cas9 protein as ribonucleoprotein (RNP) complexes and transduced with CD40L cDNA AAV6 donor. Effects of adenoviral E4orf6/Elb55k "helper" proteins co-expressed from mRNA on CD40L gene editing by Panel E) TALEN and Panel F) CRISPR/Cas9 delivered as mRNA or RNP were evaluated. Panel G) Gene modification as measured by ddPCR in LT-HSC (CD34+CD38−CD45RA−CD90+), MPP (CD34+CD38−CD45RA−CD90−), and progenitor (CD34+ CD38+) populations of PBSC modified with TALEN or CRISPR/Cas9 and AAV donor, with or without adenoviral helper protein. Statistics in panels A, D, E, and F were analyzed by Wilcoxon Rank-Sum Test. $p \leq 0.01$, $*p \leq 0.001$, NS=not significant.

FIG. 7, panels A-G, shows evaluation of nuclease reagents in primary human PBSC. Panel A) Gene integration rates in PBSC treated with TALENs and different MOI of the AAV6 cDNA donor is AAV6 dose responsive. Panel B) Viability and Panel C) fold expansion by trypan blue counting 24 hours after treatment. Viability and fold expansion by trypan blue in TALEN-(Panels D, E), and CRISPR-(Panels F, G) treated samples in PBSC 24 hours after electroporation and transduction. Samples treated with adenoviral helper proteins are depicted with checkered bars (n=6-20 biological replicates, 4 different PBSC donors). Statistics were analyzed by unpaired t test in A-C and Wilcoxon Rank-sum Test in D-G. $*p \leq 0.05$, $p \leq 0.01$, $*p \leq 0.001$, NS=not significant.

FIG. 9, panels A-F, show the results of an in vivo assay of CD34+ PBSC in NSG mice after treatment with TALEN or CRISPR, AAV6 CD40L cDNA donor and adenoviral helper proteins. Engraftment of human PBSC in the bone marrow (Panel A), spleen (Panel B), and peripheral blood (Panel C) of transplanted NSG mice, determined as the percentage of human CD45+ cells of all human and murine CD45+ cells. Panel D) Lineage distribution of human cells engrafted in NSG mice in the bone marrow 12 weeks post-transplant using fluorescent-labeled antibodies to human T cells (CD3), human B cells (CD19), human myeloid cells (CD33), human NK cells (CD56), and human progenitors (CD34). Gene editing determined by ddPCR in PBSC (Panel E) prior to transplant and in NSG bone marrow (Panel F) 12-20 weeks after transplant. Statistics were analyzed by Wilcoxon Rank-Sum Test. $**p \leq 0.01$, NS=not significant.

FIG. 10, panels A-D, shows and analysis of thymi harvested from NSG mice 12-20 weeks after transplant with gene modified PBSC. Panel A) Thymic engraftment analyzed at 3 and 5 months post-transplant. Panel B) Distribution of CD4+SP, CD8+SP, CD4+8+DP, and CD4-8-DN subsets in the thymi of mice with high levels of hCD45+ engraftment. Statistics were analyzed by Kruskal-Wallis test. NS=not significant. Panel C) Gene integration rates quantified by ddPCR in thymocytes sorted from mice at 5 months post-transplant. Panel D) TCR VP repertoire of human T lymphocytes isolated from the thymi of mice transplanted with gene-modified cells quantified by flow cytometry.

FIG. 11, panels A-C, shows the results of a surveyor nuclease assay (CEL I) of TALEN and CRISPR Off-Target Sites. Surveyor nuclease assay (CEL I) of off-target (OT) sites for TALEN 2 (Panel A) predicted in silico by PROGNOS or (Panel B) identified by GFP IDLV trapping experiments. For each OT, the first lane is from K562 cells treated with TALEN while the second lane is mock treated. Panel C) Cel-1 of CRISPR 3 off-target sites predicted in silico. For each site analyzed, the first lane is mock treated followed by CRISPR treated in biological replicates.

FIG. 12A discloses TAL1 and TAL2 as SEQ ID NOs: 50 (gcctctgcca ccttctctg) and 51 (caactttaac acagc) respectively. Panel B) Targeted re-sequencing of on-target and off-target sites by high-throughput sequencing in PBSC, XHIM CD4+ T cells, and K562 cells treated with TALEN mRNA (PBSC, XHIM T cell) or expression plasmids (K562). Statistics were analyzed by Wilcoxon Rank-Sum Test. $*p \leq 0.05$. Panel C) Off target analysis of CRISPR 3 by GUIDE-seq in K562 cells treated with CRISPR RNP and double-stranded oligodeoxynucleotides. FIG. 12C discloses SEQ ID NO: 52. Panel D) Characterization of HDR-mediated junctions between the endogenous CD40L genomic locus and the 5' end of the integrated donor cassette in samples treated with either TALEN or CRISPR and the codon-optimized donor.

Samples treated with CRISPR were also co-electroporated with a donor containing a PAM site modification to prevent re-binding of the CRISPR gRNA and repeat cleavage after cDNA integration depicted in Panel E).

Figure 13:
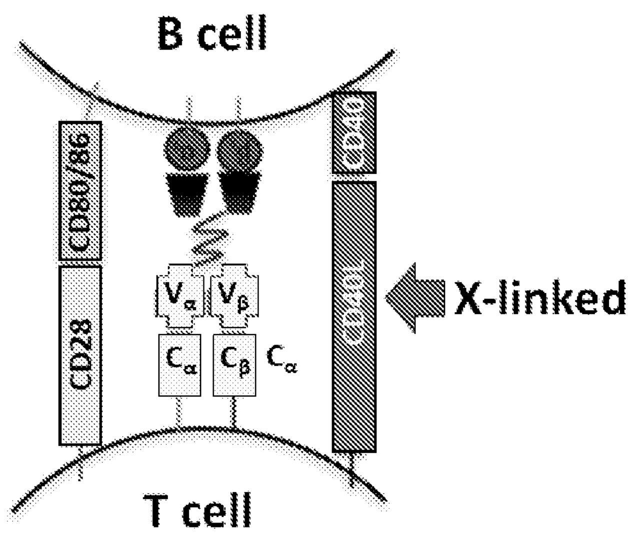

FIG. 13. Hyper-immunoglobulin M syndromes.

Figure 14:
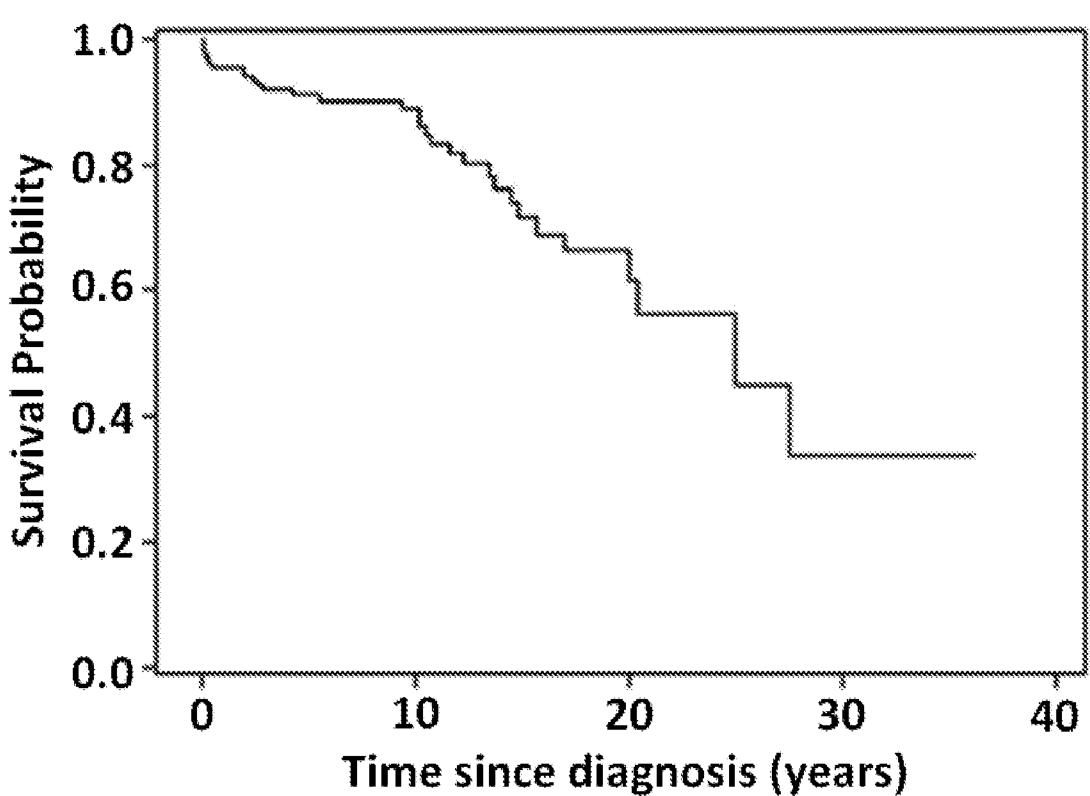

FIG. 14. XHIM prognosis and treatment.

FIG. 15 shows illustrative CD40 ligand gene mutations that lead to XHIM.

Figure 16:
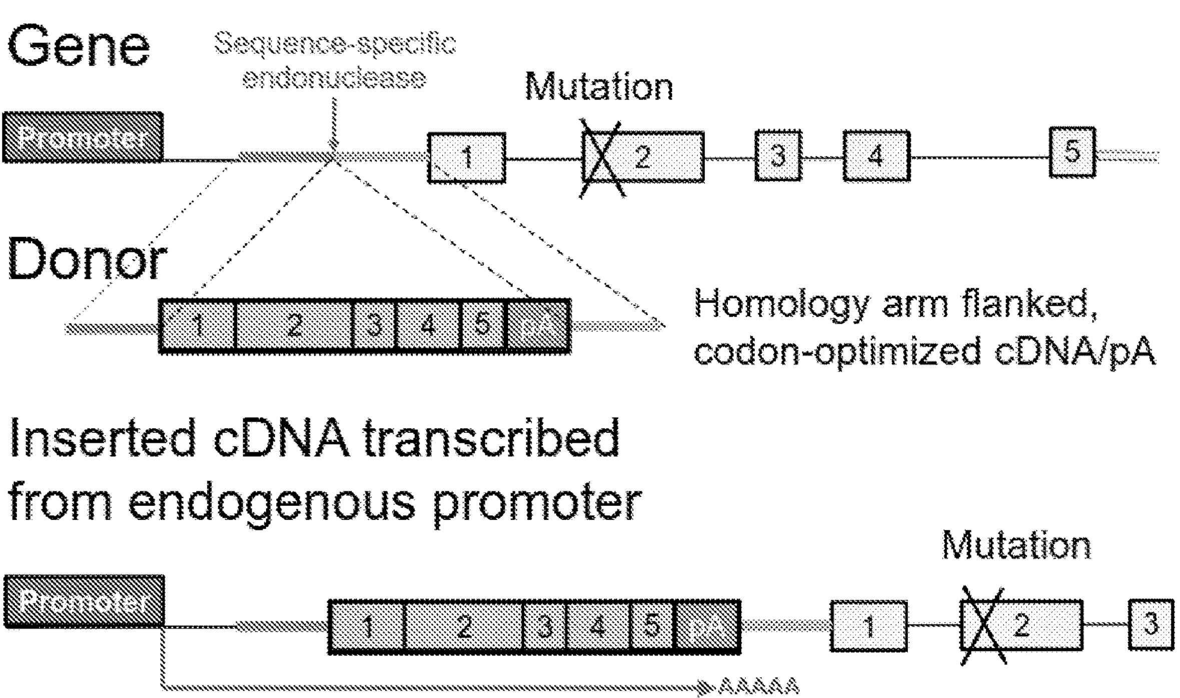

FIG. 16 illustrates one size fits all gene correction.

Figure 17:
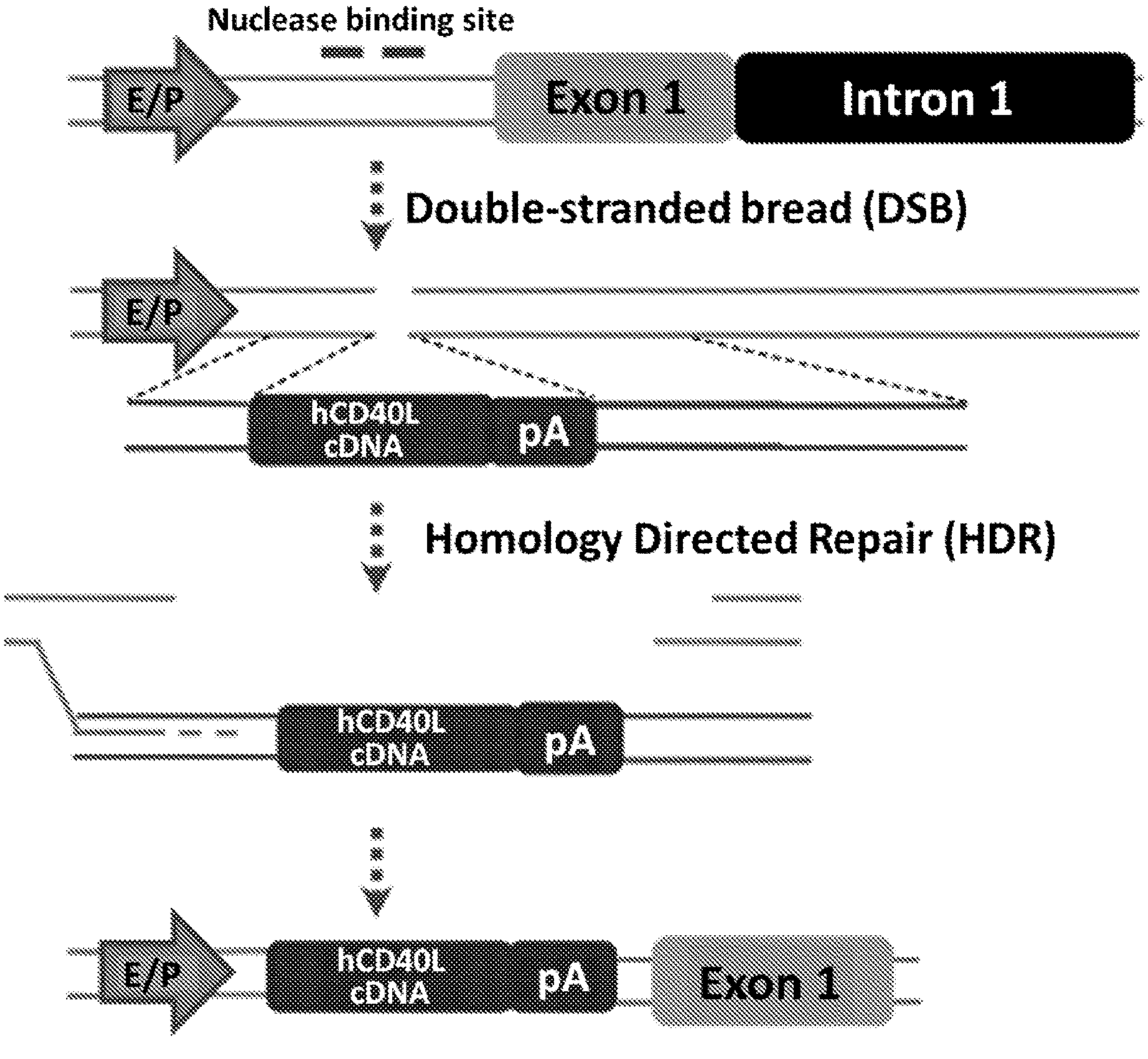

FIG. 17 shows targeted CD40L gene insertion.

Figure 18:
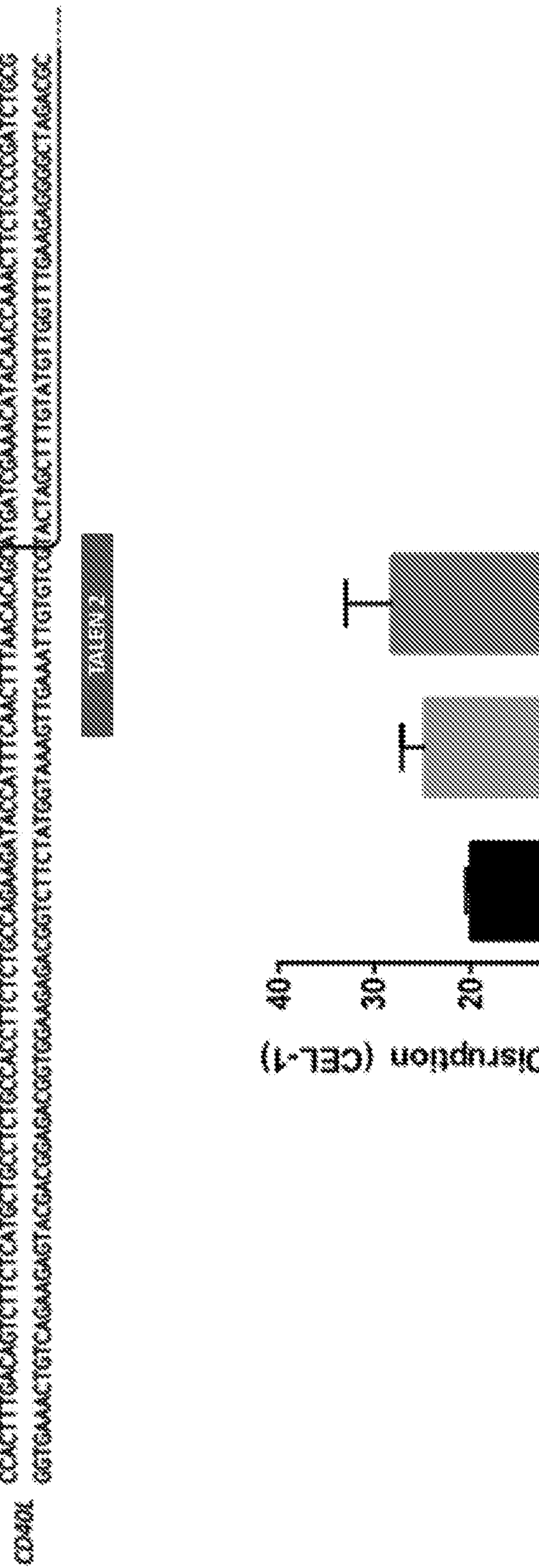

FIG. 18 illustrates the use of CRISPR/Cas in CD34+ HSC. The nucleotide sequence of the upper complementary polynucleotide strand is set forth in SEQ ID NO: 53 (ccactttgac agtcttctca tgctgcctct gccaccttct ctgccagaag atac-catttc aactttaaca cagcatgatc gaaacataca accaaacttc tccccgatct gcg). The second (lower) DNA sequence in FIG. 18 is the perfect complement to the first DNA sequence.

Figure 19:
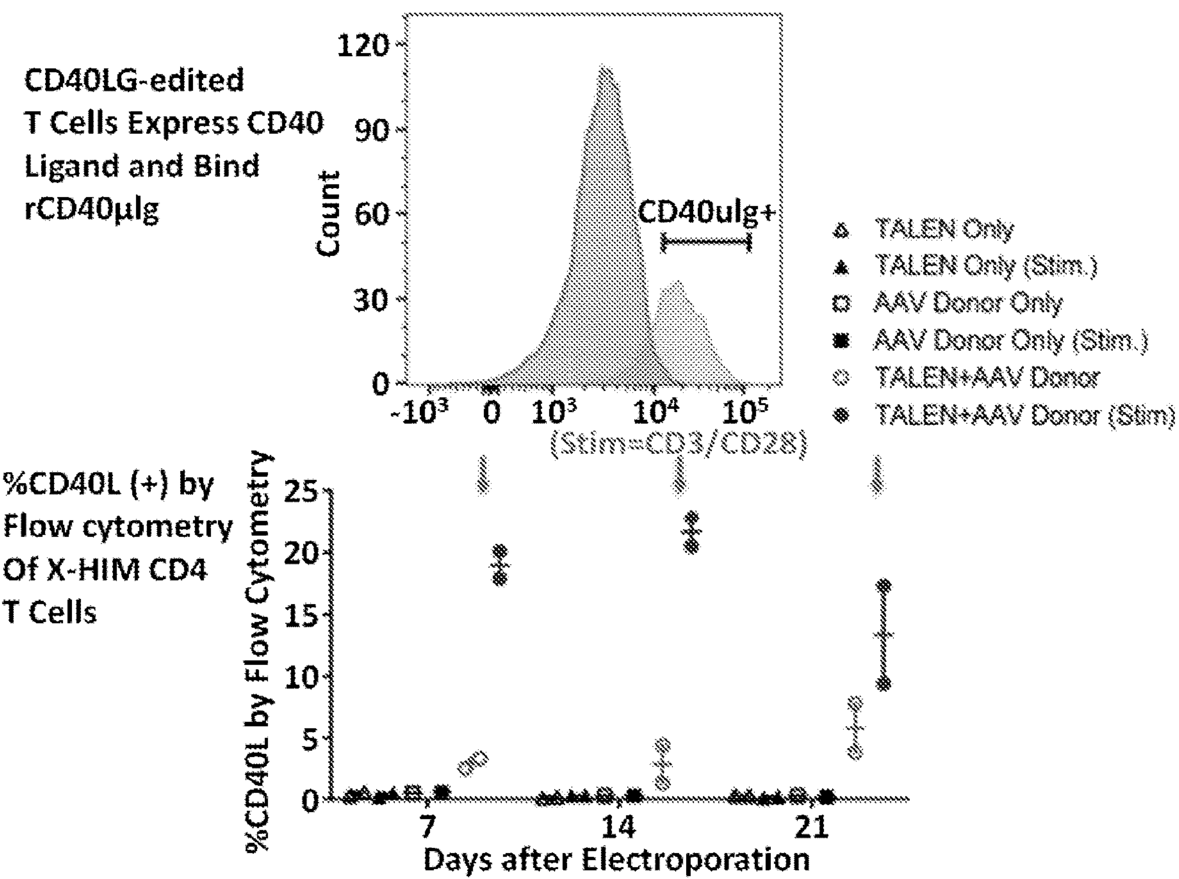

FIG. 19 illustrates characterization of CD40LG gene edited primary T cells.

Figure 20:
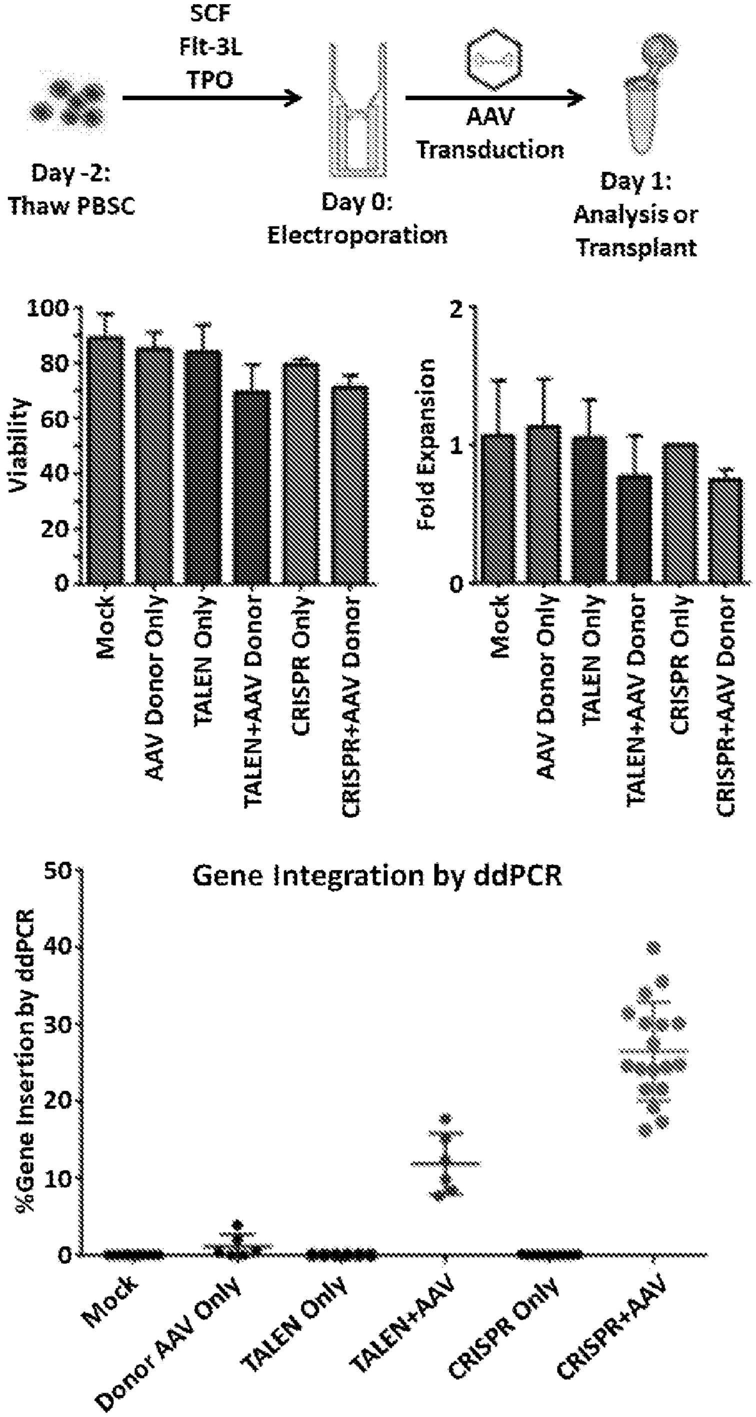

FIG. 20 shows that TALENS and CRISPRs achieve high rates of gene modification in CD34+ HSCs.

Figure 21:
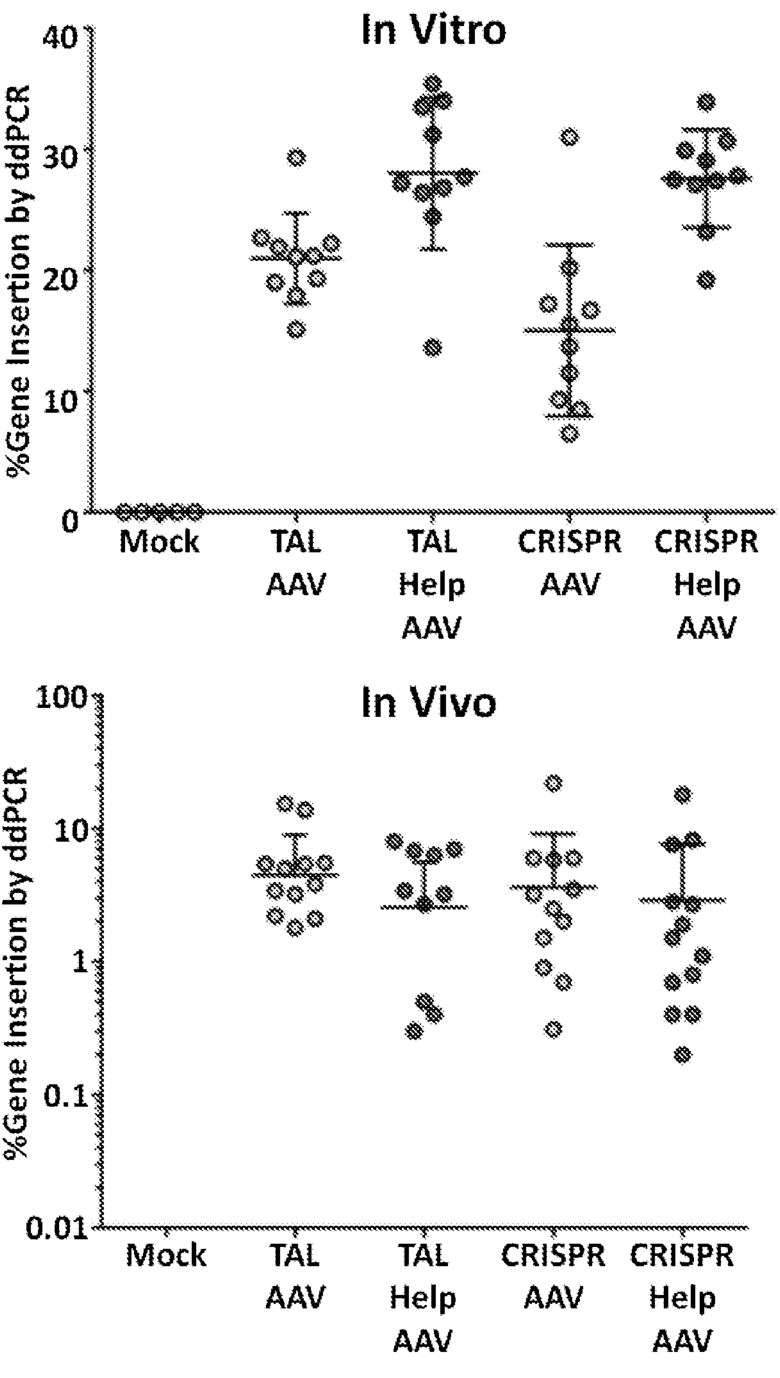

FIG. 21 illustrates site-specific CD40L cDNA insertion in human CD34+ PBSC.

Figure 22:
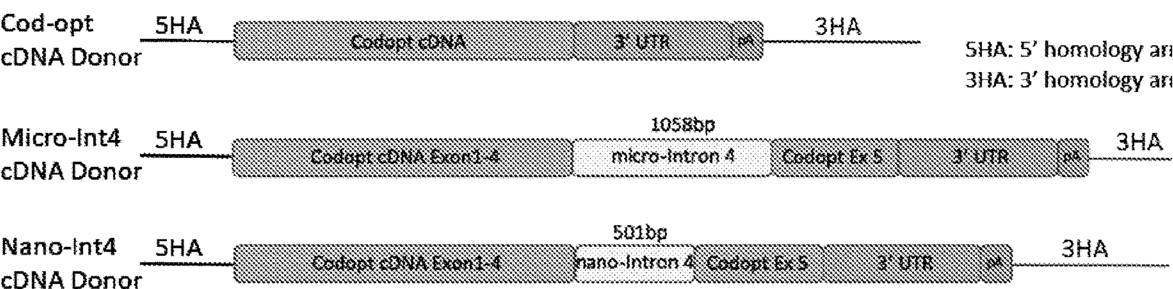

FIG. 22 shows schematics of CD40L codon-optimized cDNA donors. The first donor contains the codon optimized CD40L cDNA, 3'UTR, and poly-A signal flanked by 5' and 3' homology arms that parallel the TALEN or CRISPR/Cas9 cut site. The "micro-Int4 cDNA donor" includes the addition of a 1058 segment of intron 4 that contains a highly conserved DNaseI hypersensitivity cluster and is flanked by the endogenous intron 4 splicing machinery. The "Nano-Int4 cDNA donor" contains a similar region of intron 4 with shorter sequences flanking the DNase I hypersensitivity site.

Figure 23:
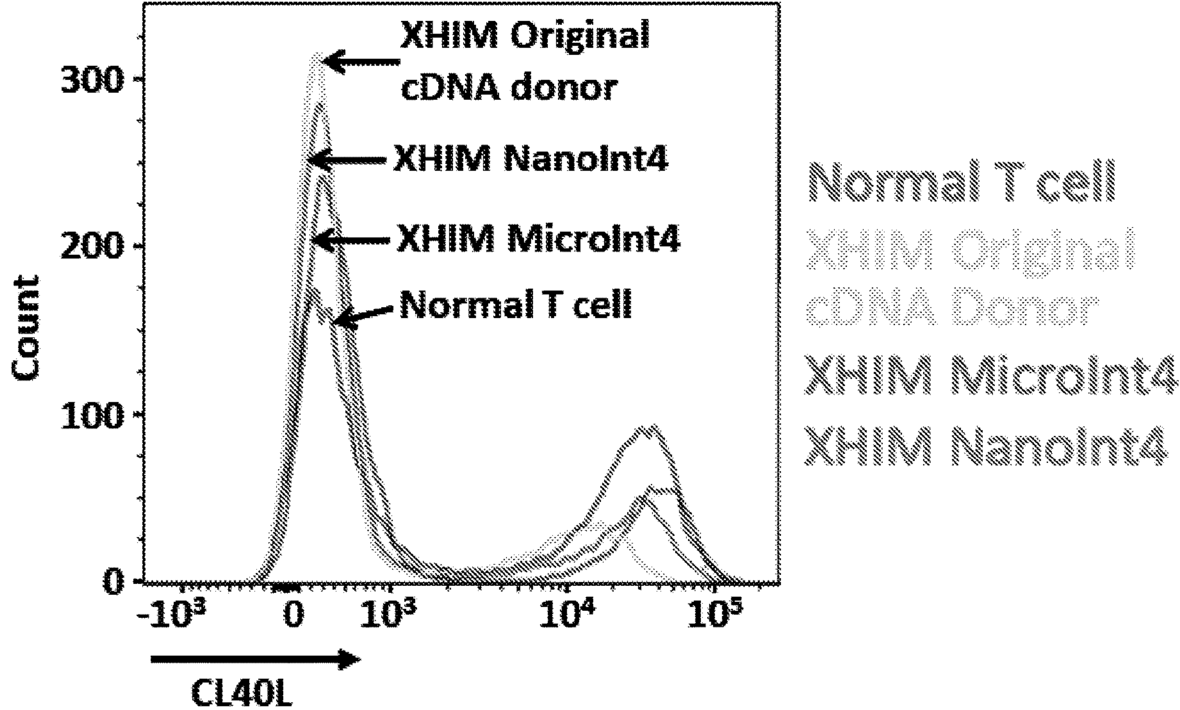

FIG. 23 shows CD40L expression by flow cytometric analysis. The base codon-optimized cDNA donor (green) achieves lower mean fluorescent intensity of CD40L expression compared to normal T cells (red). Addition of elements from the terminal intron 4 (blue and orange) increases CD40L expression to that of normal T cells.

Figure 24:
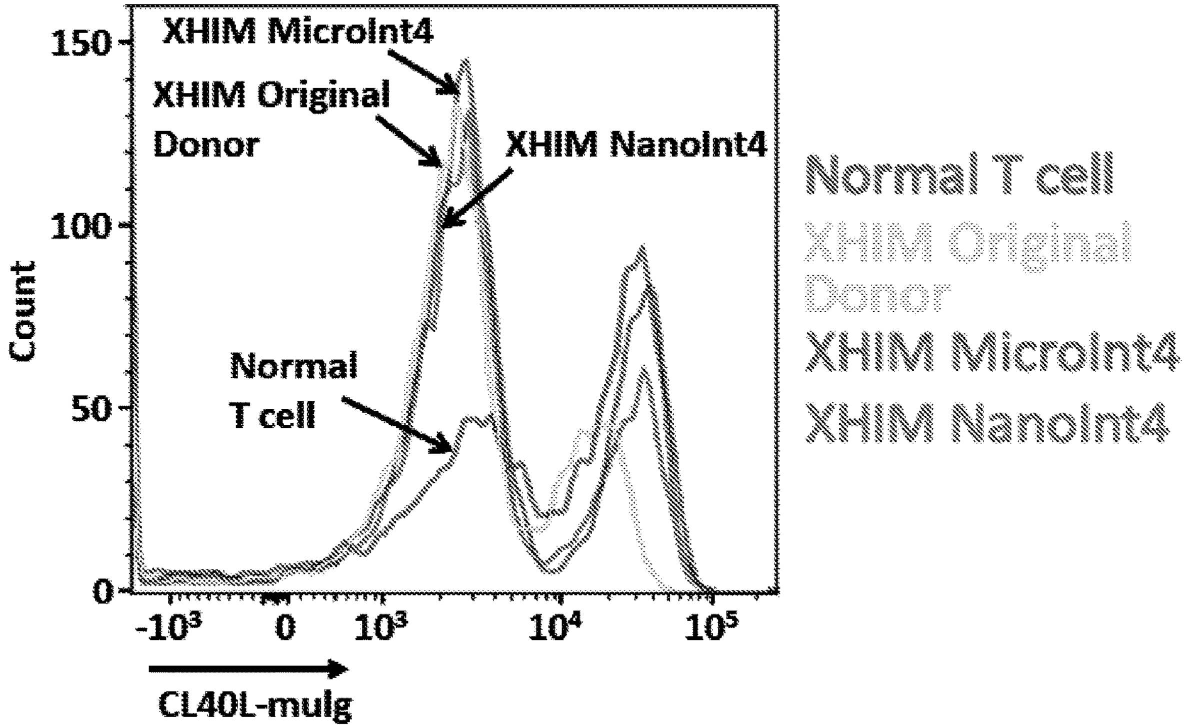

FIG. 24 shows CD40L function as measured by receptor-binding to chimeric CD40-muIg by flow cytometry. XHIM patient T cells treated with the base cDNA donor (green) had suboptimal CD40 binding compared to normal T cells. CD40 binding was restored to levels equivalent to healthy T cells with addition of micro-Int4 (blue) or nano-Int4 (orange).

FIG. 25, panels A-B, shows corrective CD40L-cDNA donor sequences. Panel A) XHIM nano-Int4 Donor which comprises a 5' Homology Arm (SEQ ID NO:3), Exon 1 (endogenous sequence) (SEQ ID NO:4), codon optimized cDNA (exons 1-4) (SEQ ID NO:5), intron 4 (Nano), codon optimized cDNA (exon 5) (SEQ ID NO:7), CD40L 3'UTR (SEQ ID NO:8), and 3' Homology Arm. These sequences are provided as a contiguous XHIM nano-Int4 Donor (SEQ ID NO: 9). Panel B) XHIM micro-Int4 Donor which comprises a 5' Homology Arm (SEQ ID NO:3), Exon 1 (endogenous sequence) (SEQ ID NO:4), codon optimized cDNA (exons 1-4) (SEQ ID NO:5), intron 4 (Micro) (SEQ ID NO: 10), codon optimized cDNA (exon 5) (SEQ ID NO:7), CD40L 3'UTR (SEQ ID NO:8), and 3' Homology Arm. These sequences are provided as a contiguous XHIM micro-Int4 Donor (SEQ ID NO:11).

DETAILED DESCRIPTION

In various embodiments methods and compositions are provided to effectively edit genes in cells (e.g., hematopoietic stem cells) to effectively correct various genetic diseases. The goal is to achieve efficient, precise gene integration and effective expression of cDNA cassettes to express normal versions of genes in hematopoietic stem cells. Applications may be for gene therapy of hemoglobinopathies, immune deficiencies, storage and metabolic diseases. In certain embodiments applications include treatment of X-Linked Hyper-IgM Syndrome (XHIM).

In certain embodiments we define optimal design features of homologous donors (cDNA expression cassettes and homology arms) and CRISPR/Cas target sites. Many of these same features may be used for gene correction, such as reversions of mutations e.g. correction of base-pair change causing SCD, replacement of deleted sequences. In various embodiments, illustrative features that were optimized include, but are not limited to one or more of the following:

a. length of homology arms;
b. modification of donor sequence and homology arms to minimize illegitimate recombination(s);
c. modification of donor sequence and homology arms to minimize targeted-recutting by a nuclease;
d. inclusion of necessary splice sites;
e. use of optimal 5' and 3' untranslated sequences that flank endogenous gene, as needed for most precise control of transgene expression;
f. optimal codon optimization algorithm for highest level expression;
g. strong polyadenylation signal;
h. editing reagents (CRISPR/Cas9/sgRNA RNP; TALEN), AAV6;
i. CRISPR/Cas9 targets in 5' UTR or early introns and avoiding splice signals are preferred targets over exons;
j. CD34+ cell processing—pre-stimulation culture conditions, times, electroporation parameters, cryopreservation;
k. Use of Geminin-Cas9 to decrease indels;
l. Selection of cells in S/G2 for editing followed by expansion; and
m. analytic methods to characterize gene editing effects at molecular (deep sequencing, TIDE, ddPCR, in-out PCR), immunologic (flow cytometry), cellular levels (CD34, primary T cells, CFU assay, NSG xenograft, artificial thymocyte assay and functional assays).

Correcting X-Linked Hyper-IgM Syndrome (XHIM) (CD40LG Pene correction)

In one illustrative, but non-limiting embodiment, methods and compositions are provided for correcting (treating) X-Linked Hyper-IgM Syndrome (XHIM) in a mammal. In various illustrative embodiments, the method comprises: i) providing differentiated T cells and/or stem/progenitor cells from said mammal; ii) performing a targeted insertion of a corrective CD40L cDNA at the CD40LG gene locus in said cells to provide a corrected CD40LG gene wherein said targeted insertion places said corrective CD40L cDNA downstream and operably linked to the endogenous CD40LG enhancer/promoter; and introducing the cells into the mammal where the corrected CD40LG gene is expressed in a physiologically regulated manner.

In certain embodiments the targeted integration of the corrective "donor" CD40L cDNA is accomplished by the use of targeted endonucleases that create targeted double-strand breaks (e.g., double strand breaks at predetermined location(s)) and promote homologous recombination of the corrective donor cDNA at the location of the double-strand breaks. In certain embodiments the targeted endonucleases comprise Zinc Finger Nucleases, Transcription Activator-Like Effector Nucleases (TALENs), or Clustered Regularly Interspaced Short Palindromic Repeats (CRISPR) associated protein (Cas) systems. Accordingly, in certain embodiments methods contemplated herein involve performing a targeted insertion (in the cells obtained from the subject or cells derived from the primary cells) by i) transducing the cells with an AAV vector or a lentiviral vector containing a donor comprising the corrective CD40L cDNA flanked by homology arms; and ii) transfecting the cells in vitro, with:

- a TALEN protein or a TALEN mRNA targeting the CD40L 5' UTR; or
- a nucleic acid encoding a guide RNA (gRNA) and CRISPR/Cas endonuclease where said gRNA targets the CD40L 5' UTR; or
- a ribonucleoprotein (RNP) complex comping a guide RNA complexed to a CRISPR/Cas endonuclease, where said gRNA targets the CD40L 5' UTR; or
- a Zinc finger endonuclease or a nucleic acid encoding a zinc finger endonuclease where the zinc finger endonuclease targets the CD40L 5' UTR.

An illustrative, but non-limiting example of a guide RNA targeting the 5'UTR of the CD40L gene and a corrective donor sequence is shown in Table 1.

TABLE 1

Illustrative, but non limiting example of guide RNA targeting the 5'UTR of the CD40L gene and a corrective donor sequence.

| | |
|---|---|
| 5UTR-2Up" guide RNA targeting the 5'UTR of the CD40L gene (SEQ ID NO: 13) | 5'-GTATCTTCTGGCAGAGAAGG-3' |
| 5UTR-2Up codon-optimized donor sequence with 3'UTR and homology arms (SEQ ID NO: 14) | CTTTACGTAACGTTTTTGCTGGGAGAGAAGA<br>CTACGAAGCACATTTTCCAGGAAGTGTGGGC<br>TGCAACGATTGTGCGCTCTTAACTAATCCTG<br>AGTAAGGTGGCCACTTTGACAGTCTTCTCAT<br>GCTGCCgCTGgaACCTTCTCTGCCAGAAGAT<br>ACCATTTCAACTTTAACACAGCATGATCGAG<br>ACATACAACCAGACCAGCCCCAGAAGCGCCG<br>CCACAGGCCTGCCTATCAGCATGAAGATCTT<br>TATGTACCTGCTGACCGTGTTCCTGATCACC<br>CAGATGATCGGCAGCGCCCTGTTCGCCGTGT<br>ACCTGCACAGACGGCTGGACAAGATCGAGGA<br>CGAGCGGAACCTGCACGAGGACTTCGTGTTC<br>ATGAAGACCATCCAGCGGTGCAACACCGGCG<br>AGAGAAGCCTGAGCCTGCTGAACTGCGAGGA<br>AATCAAGAGCCAGTTCGAGGGCTTCGTGAAG<br>GACATCATGCTGAACAAAGAGGAAACTAAGA<br>AAGAAAACAGCTTCGAGATGCAGAAGGGCGA<br>CCAGAACCCCCAGATTGCCGCCCACGTGATC<br>AGCGAGGCCAGCAGCAAGACCACCTCCGTGC<br>TGCAGTGGGCCGAGAAGGGCTACTACACCAT<br>GAGCAACAACCTCGTGACCCTGGAAAACGGC<br>AAGCAGCTGACAGTGAAGCGGCAGGGCCTGT<br>ACTACATCTACGCCCAAGTGACCTTCTGCAG<br>CAACAGAGAGGCCAGCTCCCAGGCCCCCTTT<br>ATCGCCAGCCTGTGCCTGAAGTCCCCCGGCA<br>GATTCGAGAGAATCCTGCTGAGAGCCGCCAA<br>CACCCACAGCAGCGCCAAGCCTTGTGGCCAG<br>CAGTCTATCCACCTGGGCGGCGTGTTCGAAC<br>TGCAGCCTGGCGCCTCCGTGTTCGTGAACGT<br>GACCGATCCTAGCCAGGTGTCCCACGGCACC<br>GGCTTCACAAGCTTCGGACTGCTGAAGCTGA<br>CAGTGTCACCTTGCAGGCTGTGGTGGAGCTG<br>ACGCTGGGAGTCTTCATAATACAGCACAGCG<br>GTTAAGCCCACCCCCTGTTAACTGCCTATTT<br>ATAACCCTAGGATCCTCCTTATGGAGAACTA<br>TTTATTATACACTCCAAGGCATGTAGAACTG<br>TAATAAGTGAATTACAGGTCACATGAAACCA<br>AAACGGGCCCTGCTCCATAAGAGCTTATATA<br>TCTGAAGCAGCAACCCCACTGATGCAGACAT<br>CCAGAGAGTCCTATGAAAAGACAAGGCCATT<br>ATGCACAGGTTGAATTCTGAGTAAACAGCAG<br>ATAACTTGCCAAGTTCAGTTTTGTTTCTTTG<br>CGTGCAGTGTCTTTCCATGGATAATGCATTT<br>GATTTATCAGTGAAGATGCAGAAGGGAAATG<br>GGGAGCCTCAGCTCACATTCAGTTATGGTTG<br>ACTCTGGGTTCCTATGGCCTTGTTGGAGGGG<br>GCCAGGCTCTAGAACGTCTAACACAGTGGAG<br>AACCGAAACCCCCCCCCCCCCCGCCACCCTC<br>TCGGACAGTTATTCATTCTCTTTCAATCTCT<br>CTCTCTCCATCTCTCTCTTTCAGTCTCTCTC<br>TCTCAACCTCTTTCTTCCAATCTCTCTTTCT<br>CAATCTCTCTGTTTCCCTTTGTCAGTCTCTT<br>CCCTCCCCCAGTCTCTCTTCTCAATCCCCCT<br>TTCTAACACACACACACACACACACACACAC<br>ACACACACACACACACACACACACAGAGTCA<br>GGCCGTTGCTAGTCAGTTCTCTTCTTTCCAC<br>CCTGTCCCTATCTCTACCACTATAGATGAGG<br>GTGAGGAGTAGGGAGTGCAGCCCTGAGCCTG<br>CCCACTCCTCATTACGAAATGACTGTATTTA<br>AAGGAAATCTATTGTATCTACCTGCAGTCTC<br>CATTGTTTCCAGAGTGAACTTGTAATTATCT<br>TGTTATTTATTTTTTGAATAATAAAGACCTC<br>TTAACATTATCGTCTCTGCCAGAAGATACCA<br>TTTCAACTTTAACACAGCATGATCGAAACAT<br>ACAACCAAACTTCTCCCCGATCTGCGGCCAC<br>TGGACTGCCCATCAGCATGAAAATTTTTATG<br>TATTTACTTACTGTTTTTCTTATCACCCAGA<br>TGATTGGGTCAGCACTTTTTGCTGTGTATCT<br>TCATAGAAGGTTGGACAAGGTAAGATGAACC<br>ACAAGCCTTTATTAACTAAATTTGGGGTCCT<br>TACTAATTCATAGGTTGGTTCTACCCAAATG<br>ATGGATGATGGTAGAAACCAAATAGAAGAAT<br>GGTCTTGTGGCATAATGTTTGTTGCCTAGTC<br>AATGAAGTCTCATATTCTTGTCTCTGGTTAG<br>GATCTTGGGATCTGGAGTCAGACTGCCTGGG<br>TTCAAATCTTGGCTCTGCCCATACCATCTCT<br>GTTATCCTGGGGCAAGTGCCTCAGTTTC |

The targeted endonuclease facilitates integration of the corrective cDNA in the CD40L 5'UTR thereby providing a corrected cell which can then be introduced back into the subject mammal.

Donor cDNA, Vectors, and Tar2Et Sites.

Corrective CD40L cDNA

In certain embodiments the corrective CD40L cDNA comprises all or a portion of a corrected CD40L gene and comprises all or a portion or the 3' UTR of the CD40 L gene wherein said portion of the 3' UTR is sufficient to allow binding of a polypyrimidine track binding protein (PTB) to the 3' UTR. In certain embodiments the CD40L cDNA comprises Exon 1, and/or Exon 2, and/or Exon 3, and/or Exon 4, and/or and Exon 5 of the CD40L gene. In certain embodiments the CD40L cDNA donor comprises all of the 3' UTR of the CD40L gene. In certain embodiments the CD40L cDNA donor comprises a portion of the 3' UTR sufficient to allow binding of a polypyrimidine track binding protein (PTB) to the 3' UTR.

In certain embodiments the corrective CD40L cDNA comprises all five exons (785 bp) of the CD40L gene along with the 3' UTR (944 bp) of the human CD40LG gene. In certain embodiments the 3' UTR is followed by the bGH polyA signal (24 bp). In certain embodiments the cDNA donor sequence is flanked by a 5' homology arm that begins at the TALEN or CRISPR/Cas cut site and extends at least 40 bp, or at least 50 bp, or at least 60 bp, or at least 70 bp, or at least 80 bp, or at least 90 bp at least 100 bp, or at least 110 bp, or at least 120 bp, or at least 130 bp, or at least 140 bp, or at least 150 bp, or at least 160 bp upstream from the cut site. In certain embodiments the 5' homology arm extends 162 bp upstream from said cut site. In certain embodiments the cDNA donor sequence is flanked by a 3' homology arm that extends at least 100 bp, or at least 150 bp, or at least 200 bp, or at least 250 bp, or at least 300 bp, or at least 350 bp, or at least 400 bp downstream of the TALEN or CRISPR/Cas cut site. In certain embodiments the cDNA donor sequence is flanked by a 3' homology arm that extends 405 bp downstream of the TALEN or CRISPR/Cas cut site.

Corrective cDNA Modifications and Introduction into Cells.

In certain embodiments the cDNA donor (e.g., CD40 L cDNA) is codon-optimized/-divergent. In certain embodiments this is accomplished by using algorithms to choose the most favored codon for each amino acid. Besides increasing the amount of protein made, it also makes the incoming homologous donor less sequence identical to the endogenous gene and less likely to recombine in unwanted ways In certain embodiments the cDNA donor is modified to exclude protospacer adjacent motifs (PAMs). In certain embodiments the cDNA donor is modified by modifying a PAM sequence TGG to TAA.

In certain embodiments the donor nucleic acid is introduced into the host cell 5 (e.g., PBSC) using a viral vector. Illustrative vectors include, but are not limited to adenoviral vectors, adeno-associated virus vectors, lentivirus vectors, vaccinia virus vectors, and RNA virus vectors (such as retroviral vectors). In certain embodiments vectors suitable for introduction of polynucleotides (e.g. nuclease-encoding polynucleotides and/or donor transgene polynucleotides) described herein include non-integrating lentivirus vectors (IDLV) (see, e.g., Ory et al. (1996) *Proc. Natl. Acad. Sci. USA,* 93: 11382-11388; Dull et al. (1998) *J. Virol.* 72: 8463-8471; Zuffery et al. (1998) *J. Virol.* 72: 9873-9880; Follenzi et al. (2000) *Nat. Genet.* 25: 217-222; U.S. Patent Publication No 2009/054985; and the like which are incorporated herein by reference for the IDLVs and methods of use thereof described therein. A number of IDLVs are also commercially available (see, e.g. TaKaRa LENTI-X™ HTX Packaging System (Integrase Deficient), and the like).

In certain embodiments the donor nucleic acid is introduced into the host cells using an adeno-associated virus (AAV). More than 30 naturally occurring serotypes of AAV are available. AAV viruses can be engineered by conventional molecular biology techniques, making it possible to optimize these particles for cell specific delivery of the desired nucleic acid sequences, for minimizing immunogenicity, for tuning stability and particle lifetime, for efficient degradation, for accurate delivery to the nucleus, etc.

The use of AAVs is a common mode of exogenous delivery of DNA as it is relatively non-toxic, provides efficient gene transfer, and can be easily optimized. Among the serotypes of AAVs isolated from human or non-human primates (NHP) and well characterized, human serotype 2 is the first AAV that was developed as a gene transfer vector. This serotype has been widely used for efficient gene transfer experiments in different target tissues and animal models. Other AAV serotypes include, but are not limited to, AAV1, AAV3, AAV4, AAV5, AAV 6, AAV7, AAVS and AAV9 (e.g., see, e.g., WO 2005/033321 for a discussion of various AAV serotypes).

In certain embodiments the AAV comprises an AAV serotype 6, e.g., as illustrated in Example 1.

Targeted Endonucleases.

In various embodiments, targeted endonucleases (e.g., TALENs, CRISPR/Cas, Zinc Finger endonucleases, etc.) are used to insert a corrective donor cDNA into the gene (e.g., CD40L 5' UTR) in a targeted manner. In various embodiments the targeted endonucleases can be introduced into the cell as a protein or as a nucleic acid (e.g., an mRNA, or a vector) encoding the protein. In the case of CRISPR/Cas, the endonuclease can be introduced as a single nucleic acid encoding the CRISPR/Cas endonuclease and a guide RNA, as separate nucleic acids encoding the CRISPR/Cas endonuclease and the guide protein, or as a ribonucleoprotein (RNP) complex comprising the CRISPR/Cas endonuclease and the guide RNA (gRNA). In certain embodiments the ribonucleoprotein (RNP) complex comprises the CRISPR/Cas endonuclease conjugated to the guide RNA (gRNA).

Methods of introducing targeted endonucleases (and guide RNAs when required) into the cells (transecting the cells) are well known to those of skill in the art. Such methods include, but are not limited to electroporation, sonoporation, cell squeezing, optical transfection, impalefection, and the like. Electroporation is a particularly suitable method (see, e.g., Example 1) where transient increase in the permeability of cell membrane is achieved when the cells are exposed to short pulses of an intense electric field. Cell squeezing enables delivery of molecules into cells via cell membrane deformation. It is a high throughput vector-free microfluidic platform for intracellular delivery. It reduces the possibility of toxicity or off-target effects as it does not rely on exogenous materials or electrical fields (e.g., Sharei et al. (2013) *Proc. Natd. Acad. Sci. USA,* 110 (6): 2082-2087). Sonoporation uses high-intensity ultrasound to induce pore formation in cell membranes. Optical transfection is a method where a tiny (~1 μm diameter) hole is transiently generated in the plasma membrane of a cell using a highly focused laser (see, e.g., Tsukakoshi et al. (1984) *Appl. Physics B: Photophysics and Laser Chem.* 35 (3): 135-140). Impalefection is a method of introducing a nucleic acid bound to a surface of a nanofiber that is inserted into a cell. This approach can also be implemented with arrays of nanofibers that are introduced into large numbers of cells and intact tissue.

Illustrative, but non-limiting, chemical-based transfection methods include, but are not limited to, calcium phosphate, transfection, dendrimers-based transfection, the use of cationic polymers (e.g., DEAE-dextran or polyethylenimine (PEI)), lipofection (e.g., using a positively charged (cationic) lipid or cationic liposomes, or mixtures thereof), or a non-liposomal transfection reagent such as FUGENE®.

Illustrative, but non-limiting, particle-based transfection methods include, but are not limited to the gene gun, where the DNA is coupled to a nanoparticle of an inert solid (commonly gold), which is then "shot" directly into the target cell's nucleus, magnetofection, or magnet-assisted transfection, where magnetic force is used to deliver nucleic acids into target cells, and the like.

These methods of introducing the endonuclease, and/or nucleic acid encoding an endonuclease, and/or a gRNA (where required) are illustrative and non-limiting. Using the teachings provided herein, numerous other approaches will be available to one of skill in the art.

TALENs

In certain embodiments the targeting endonuclease can be a Transcription Activator-Like Effector Nuclease (TALEN). TAL effector nucleases are a class of sequence-specific nucleases derived from Xanthomonas bacteria, that can be used to make double-strand breaks at specific target sequences in the genome of a prokaryotic or eukaryotic organism. The DNA binding domain of the TAL effector contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences (see, e.g., WO 2010/079430; Morbitzer et al. (2010) *Proc. Natl. Acad. Sci. USA,* 107(50): 21617-21622; Scholze & Boch (2010) *Virulence,* 1: 428-432; Christian et al. (2010) *Genetics,* 186:757-761; Li et al. (2010) *Nucl. Acids Res.* (1):359-372; and Miller et al. (2011) *Nat. Biotechl.* 29: 143-148).

To produce a TALEN, a TAL protein is fused to a nuclease, which is typically a wild-type or mutated FokI endonuclease. Several mutations to FokI have been made for its use in TALENs. These, for example, improve cleavage specificity or activity (see, e.g., Cermak et al. (2011) *Nucl. Acids Res.* 39: e82; Miller et al. (2011) *Nat. Biotech.* 29: 143-148; Hockemeyer et al. (2011) *Nat. Biotech.* 29: 731-734; Wood et al. (2011) *Science,* 333: 307; Doyon et al. (2010) *Nat. Meth.* 8: 74-79; Szczepek et al. (2007) *Nat. Biotech.* 25: 786-793; and Guo et al. (2010) *J. Mol. Biol.* 200: 96).

The FokI domain functions as a dimer, typically requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity (see, e.g., Miller et al. (2011) *Nat. Biotech.,* 29: 143-148).

Examples of suitable TAL nucleases, and methods for preparing suitable TAL nucleases, are disclosed, e.g., in US Patent Application Nos. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1. In various embodiments, TAL effector nucleases are engineered that cut in or near a target nucleic acid sequence in, e.g., a genomic locus of interest (e.g., in the CD40L 5' UTR), where the target nucleic acid sequence is at or near a sequence to be modified by a targeting vector (e.g., CD40L 5' UTR). The TAL nucleases suitable for use with the various methods and compositions provided herein include those that are specifically designed to bind at or near target nucleic acid sequences to be modified by targeting vectors as described herein (e.g., in the CD40L 5' UTR, see e.g., TALEN 1, TALEN2, and TALEN3 in FIG. 1, panel A).

In one illustrative, but non-limiting embodiment, each monomer of the TALEN comprises 10 or more DNA binding repeats, and in some cases 15 or more DNA binding repeats (e.g., in certain embodiments, 12-25 TAL repeats), wherein each TAL repeat binds a 1 bp subsite. In one embodiment, the nuclease agent is a chimeric protein comprising a TAL repeat-based DNA binding domain operably linked to an independent nuclease. In one embodiment, the independent nuclease is a Fok1 endonuclease (see e.g., Kim et al. (1996) *Proc. Natl. Acad. Sci. USA,* 93:1156-1160), however, other useful endonucleases may include, but are not limited to, for example, HhaI, HindIII, Nod, BbvCI, EcoRI, BglI, and AlwI.

In some embodiments, the TAL effector domain that binds to a specific nucleotide sequence within the target DNA (e.g., CD40L 5' UTR) comprises a plurality of repeat variable-diresidues (RVD) each of which determines recognition of a base pair in the target DNA sequence, where each DNA binding repeat is responsible for recognizing one base pair in the target DNA sequence, and wherein the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T.

Figure 1:
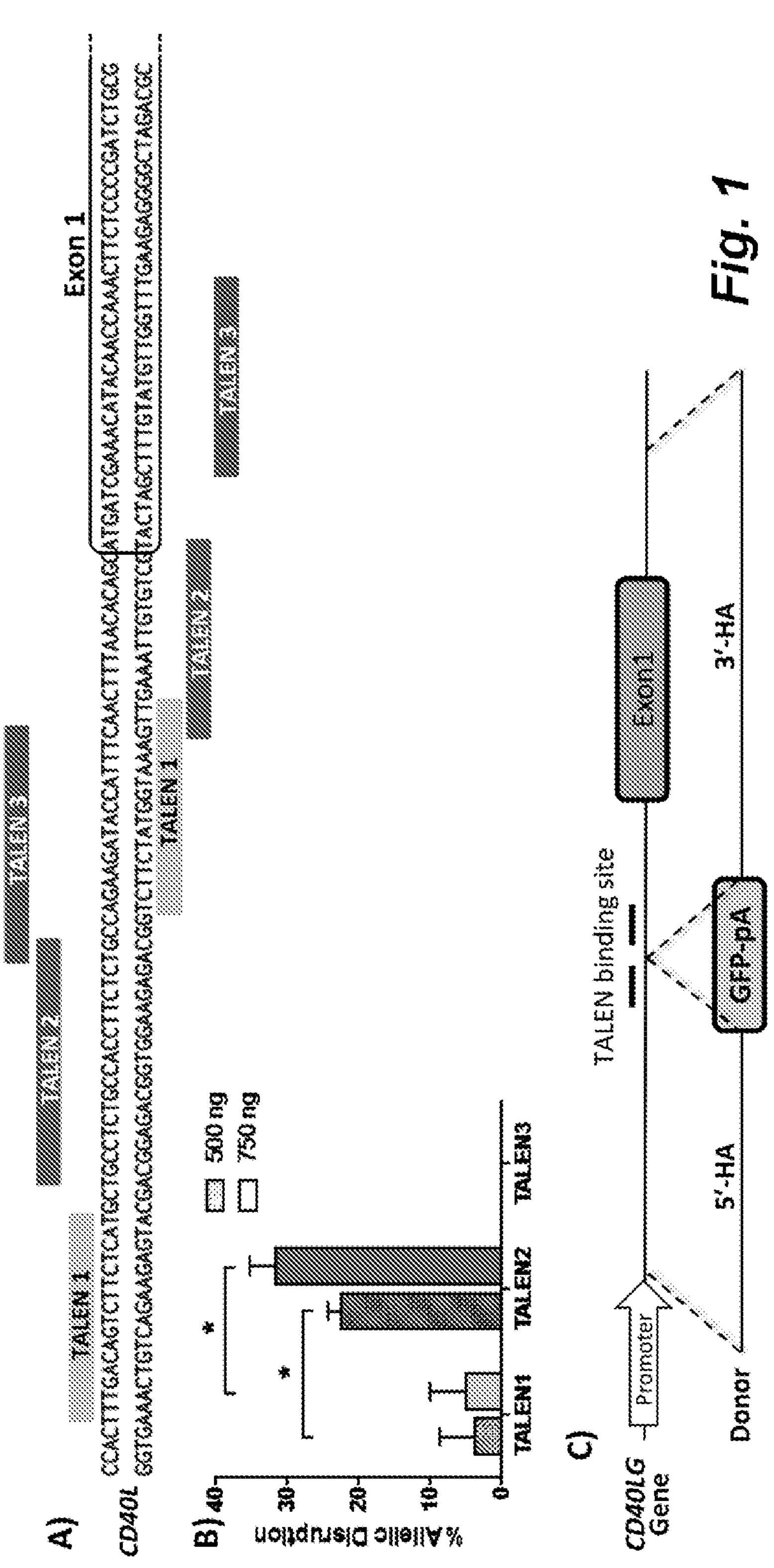
FIG. 1, panels A-G. Targeted integration in cell lines of a promoterless GFP cassette at the 5'UTR of the human CD40L gene. Panel A) Binding sites for three TALEN pairs that cleave within the 5'UTR sequence of CD40LG (SEQ ID NO:1). Panel B) Expression plasmids encoding TALEN pairs 1, 2 or 3 were electroporated into K562 cells using 500 ng or 750 ng of plasmid and allelic disruption at the CD40LG 5' UTR was quantified using surveyor nuclease assay. Statistics were analyzed by Kruskal-Wallis Test to assess overall significance and the Dwass-Steel-Critchlow-Fligner method for multiple pairwise tests. Data are presented as mean±SD. *p<0.05. n=4-6 biological replicates. C) Schematic of a promoterless GFP—polyadenylation signal (pA) cassette donor flanked by homology arms (HA) that parallel the TALEN cut site. Panel D) The schema and primer locations for 'In-Out' PCR to detect site-specific integration of the GFP donor in the CD40LG 5' UTR is shown at the top. K562 cells were electroporated with a dose range (250-750 ng) of TALEN plasmid and five- to ten-fold weight ratio of plasmid containing the GFP donor and assayed for site-specific integration by In-Out PCR. Panel E) Jurkat T cells, a CD40L expressing human T cell line, were electroporated with 250, 500 or 750 ng of the TALEN expression plasmid and ten-fold weight ratio of the GFP donor plasmid. Stability of GFP expression over one month and Panel F) response to immune stimulation with phytohemagglutinin (PHA) was determined by flow cytometry. (n=2 biological replicates) Panel G) Representative flow cytometric plots of Jurkat T cells treated with 500 ng TALEN plasmid and 5000 ng donor GFP plasmid with increasing doses of PHA.

If the genome editing endonuclease to be utilized is a TALEN, in some embodiments, optimal target sites may be selected in accordance with the methods described by Sanjana et al. (2012) *Nat. Protocol.,* 7: 171-192, which is hereby incorporated by reference in its entirety. In brief, in various embodiments, TALENs function as dimers, and a pair of TALENs, referred to as the left and right TALENs, target sequences on opposite strands of DNA. TALENs can be engineered as a fusion of the TALE DNA-binding domain and a monomeric FokI catalytic domain. In certain embodiments to facilitate FokI dimerization, the left and right TALEN target sites can be chosen with a spacing of approximately 14-20 bases. Therefore, for a pair of TALENs, each targeting 20-bp sequences, an optimal target site can have the form 5'-$TN^{19}N^{14-20}N^{19}$A-3', where the left TALEN targets 5'-$TN^{19}$-3' and the right TALEN targets the antisense strand of 5'-$N^{19}$A-3' (N=A, G, T or C). This is of course illustrative and non-limiting and examples of TALENs that bind to CD40L 5' UTR are illustrated in FIG. 1, panel A). For more information on TALENs, refer to U.S. Pat. No. 8,685,737, which is hereby incorporated by reference in its entirety.

The use of TALEN pairs to insert a donor cDNA into the CD40L 5' UTR) is illustrated in Example 1. It is noted, however, that the TALENs described therein are illustrative and non-limiting and, using the teachings provided herein other TALEN pairs can readily be utilized by one of skill in the art.

CRISPR/Cas Systems.

In certain embodiments the targeting endonuclease can comprise a CRISPR/Cas endonuclease which is typically guided to a target site by one or more guide RNAs (gRNAs). CRISPR-based endonucleases are RNA-guided endonucleases derived from CRISPR/Cas systems. Bacteria and archaea have evolved an RNA-based adaptive immune system that uses CRISPR (clustered regularly interspersed short palindromic repeat) and Cas (CRISPR-associated) proteins to detect and destroy invading viruses or plasmids. CRISPR/Cas endonucleases can be programmed to introduce targeted site-specific double-strand breaks by providing target-specific synthetic guide RNAs (see, e.g., Jinek et al. (2012) *Science,* 337: 816-821).

In various embodiments the CRISPR-based endonuclease can be derived from a CRISPR/Cas type I, type II, type III, type V, or type VI system. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

Type II CRISPR/Cas Endonucleases (e.g., Cas 9)

In certain embodiments, the CRISPR-based endonuclease is derived from a type II CRISPR/Cas system. In illustrative, but non-limiting embodiments, the CRISPR-based endonuclease is derived from a Cas9 protein. In certain embodiments the Cas9 protein can be from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus*, or *Acaryochloris marina*. In one specific illustrative embodiment, the CRISPR-based nuclease is derived from a Cas9 protein from *Streptococcus pyogenes.*

In general, CRISPR/Cas proteins comprise at least one RNA recognition and/or RNA binding domain. RNA recognition and/or RNA binding domains interact with the guide RNA such that the CRISPR/Cas protein is directed to a specific genomic or genomic sequence. CRISPR/Cas proteins can also comprise nuclease domains (i.e., DNase or RNase domains), DNA binding domains, helicase domains, protein-protein interaction domains, dimerization domains, as well as other domains.

The CRISPR-based endonuclease used herein can be a wild type CRISPR/Cas protein, a modified CRISPR/Cas protein, or a fragment of a wild type or modified CRISPR/Cas protein. In certain embodiments the CRISPR/Cas protein can be modified to increase nucleic acid binding affinity and/or specificity, alter an enzymatic activity, and/or change another property of the protein. For example, the CRISPR/Cas protein can be truncated to remove domains that are not essential for the function of the protein. The CRISPR/Cas protein also can be truncated or modified to optimize the activity of the protein or an effector domain fused with the CRISPR/Cas protein.

In some embodiments, the CRISPR-based endonuclease can be derived from a wild type Cas9 protein or fragment thereof. In other embodiments, the CRISPR-based endonuclease can be derived from a modified Cas9 protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-strand break in DNA (see, e.g., Jinek et al. (2012) *Science,* 337: 816-821). In one embodiment, the CRISPR-based endonuclease is derived from a Cas9 protein and comprises two function nuclease domains, which together introduce a double-stranded break into the targeted site.

The target sites recognized by naturally occurring CRISPR/Cas systems typically having lengths of about 14-15 bp (see, e.g., Cong et al. (2013) *Science,* 339: 819-823). The target site has no sequence limitation except that sequence complementary to the 5' end of the guide RNA (i.e., called a protospacer sequence) is typically immediately followed by (3' or downstream) a consensus sequence. This consensus sequence is also known as a protospacer adjacent motif (or PAM). Examples of PAM include, but are not limited to, NGG, NGGNG, and NNAGAAW (wherein N is defined as any nucleotide and W is defined as either A or T). At the typical length, only about 5-7% of the target sites would be unique within a target genome, indicating that off target effects could be significant. The length of the target site can be expanded by requiring two binding events. For example, CRISPR-based endonucleases can be modified such that they can only cleave one strand of a double-stranded sequence (i.e., converted to nickases). Thus, the use of a CRISPR-based nickase in combination with two different guide RNAs would essentially double the length of the target site, while still effecting a double stranded break.

The requirement of the crRNA-tracrRNA complex in a CRISPR/Cas system can be avoided by use of an engineered "single-guide RNA" (sgRNA) that comprises the hairpin normally formed by the annealing of the crRNA and the tracrRNA (see Jinek et al. (2012) *Science* 337:816; Cong et al. (2013) Sciencexpress/10.1126/science.1231143). In S. pyrogenes, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing and has been useful for zebrafish embryo genomic editing in vivo (see Hwang et al. (2013) *Nat. Biotechnol.,* 31(3):227) with editing efficiencies similar to ZFNs and TALENs.

Accordingly in certain embodiments, a CRISPR/Cas endonuclease complex used in the methods described herein comprises a Cas protein and at least one to two ribonucleic acids (e.g., gRNAs) that are capable of directing the Cas protein to and hybridizing to a target motif of a target polynucleotide sequence. In some embodiments, a CRISPR/Cas endonuclease complex used in the methods described herein comprises a Cas protein and one ribonucleic acid (e.g., gRNA) that us capable of directing the Cas protein to and hybridizing to a target motif of a target polynucleotide sequence.

As used herein, "protein" and "polypeptide" are used interchangeably to refer to a series of amino acid residues joined by peptide bonds (i.e., a polymer of amino acids) and include modified amino acids (e.g., phosphorylated, glycated, glycosolated, etc.) and amino acid analogs. Illustrative polypeptides or proteins include gene products, naturally occurring proteins, homologs, paralogs, fragments and other equivalents, variants, and analogs of the above.

In some embodiments, a Cas protein comprises a core Cas protein. Illustrative Cas core proteins include, but are not limited to, Cas1, Cas2, Cas3, Cas4, Cas5, Cas6, Cas7, Cas8 and Cas9. In some embodiments, a Cas protein comprises a Cas protein of an *E. coli* subtype (also known as CASS2). Illustrative Cas proteins of the *E. Coli* subtype include, but are not limited to Cse1, Cse2, Cse3, Cse4, and Cas5e. In some embodiments, a Cas protein comprises a Cas protein of the Ypest subtype (also known as CASS3). Illustrative Cas proteins of the Ypest subtype include, but are not limited to Csy1, Csy2, Csy3, and Csy4. In some embodiments, a Cas protein comprises a Cas protein of the Nmeni subtype (also known as CASS4). Illustrative Cas proteins of the Nmeni subtype include, but are not limited to Csn1 and Csn2. In some embodiments, a Cas protein comprises a Cas protein of the Dvulg subtype (also known as CASS1). Illustrative Cas proteins of the Dvulg subtype include Csd1, Csd2, and Cas5d. In some embodiments, a Cas protein comprises a Cas protein of the Tneap subtype (also known as CASS7). Illustrative Cas proteins of the Tneap subtype include, but are not limited to, Cst1, Cst2, Cas5t. In some embodiments, a Cas protein comprises a Cas protein of the Hmari subtype. Illustrative Cas proteins of the Hmari subtype include, but are not limited to Csh1, Csh2, and Cas5h. In some embodiments, a Cas protein comprises a Cas protein of the Apern subtype (also known as CASS5). Illustrative Cas proteins of the Apern subtype include, but are not limited to Csa1, Csa2, Csa3, Csa4, Csa5, and Cas5a. In some embodiments, a Cas protein comprises a Cas protein of the Mtube subtype (also known as CASS6). Illustrative Cas proteins of the Mtube subtype include, but are not limited to Csm1, Csm2, Csm3, Csm4, and Csm5. In some embodiments, a Cas protein comprises a RAMP module Cas protein. Illustrative RAMP module Cas proteins include, but are not limited to, Cmr1, Cmr2, Cmr3, Cmr4, Cmr5, and Cmr6.

In some embodiments, the Cas protein is a *Streptococcus pyogenes* Cas9 protein (spCas9) or a functional portion thereof (see, e.g., UniProtKB-Q99ZW2 (CAS9_STRP1)). In some embodiments, the Cas protein is a *Staphylococcus aureus* Cas9 protein (saCas9) or a functional portion thereof. In some embodiments, the Cas protein is a *Streptococcus thermophilus* Cas9 protein (stCas9) or a functional portion thereof. In some embodiments, the Cas protein is a *Neisseria meningitides* Cas9 protein (nmCas9) or a functional portion thereof. In some embodiments, the Cas protein is a *Treponema denticola* Cas9 protein (tdCas9) or a functional portion thereof. In some embodiments, the Cas protein is Cas9 protein from any other bacterial species or functional portion thereof.

Type V and Type VI CRISPR/Cas Endonucleases

In certain embodiments the CRISPR/Cas endonuclease systems contemplated herein include, but are not limited to a type V or type VI CRISPR/Cas endonuclease (e.g., the genome editing endonuclease is a type V or type VI CRISPR/Cas endonuclease) (e.g., Cpf1, C2c1, C2c2, C2c3). Type V and type VI CRISPR/Cas endonucleases are a type of class 2 CRISPR/Cas endonuclease. Examples of type V CRISPR/Cas endonucleases include but are not limited to: Cpf1, C2c1, and C2c3. An example of a type VI CRISPR/Cas endonuclease is C2c2. In some cases, a subject genome targeting composition includes a type V CRISPR/Cas endonuclease (e.g., Cpf1, C2c1, C2c3). In some cases, a Type V CRISPR/Cas endonuclease is a Cpf1 protein. In some cases, a subject genome targeting composition includes a type VI CRISPR/Cas endonuclease (e.g., C2c2)

Like type II CRISPR/Cas endonucleases, type V and VI CRISPR/Cas endonucleases form a complex with a corresponding guide RNA. The guide RNA provides target specificity to an endonuclease-guide RNA RNP complex by having a nucleotide sequence (a guide sequence) that is complementary to a sequence (the target site) of a target nucleic acid (as described elsewhere herein). The endonuclease of the complex provides the site-specific activity. In other words, the endonuclease is guided to a target site (e.g., stabilized at a target site) within a target nucleic acid sequence (e.g., a chromosomal sequence) by virtue of its association with the protein-binding segment of the guide RNA.

Examples and guidance related to type V and type VI CRISPR/Cas proteins (e.g., cpf1, C2c1, C2c2, and C2c3 guide RNAs) can be found in the art (see, e.g., Zetsche et al. (2015) *Cell,* 163(3):759-771; Makarova et al. (2015) *Nat. Rev. Microbiol.* 13(11): 722-736; Shmakov et al. (2015) *Mol. Cell,* 60(3):385-397; and the like).

In some cases, the Type V or type VI CRISPR/Cas endonuclease (e.g., Cpf1, C2c1, C2c2, C2c3) is enzymatically active, e.g., the Type V or type VI CRISPR/Cas polypeptide, when bound to a guide RNA, and cleaves a target nucleic acid. In some cases, the Type V or type VI CRISPR/Cas endonuclease (e.g., Cpf1, C2c1, C2c2, C2c3) exhibits reduced enzymatic activity relative to a corresponding wild-type a Type V or type VI CRISPR/Cas endonuclease (e.g., Cpf1, C2c1, C2c2, C2c3), and retains DNA binding activity.

In some cases a type V CRISPR/Cas endonuclease is a Cpf1 protein or a functional portion thereof (see, e.g., UniProtKB-A0Q7Q2 (CPF1_FRATN)). Cpf1 protein is a member of the type V CRISPR system and is a polypeptide comprising about 1300 amino acids. Cpf1 contains a RuvC-like endonuclease domain. Unlike Cas9, Cpf1 cleaves target DNA in a staggered pattern using a single ribonuclease domain. The staggered DNA double-stranded break results in a 4 or 5-nt 5' overhang.

The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see, e.g., Fagerlund et al. (2015) *Genom. Bio.* 16: 251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "Cas" includes both Cas9 and Cfp1 proteins. Accordingly, as used herein, a "CRISPR/Cas system" refers both CRISPR/Cas and/or CRISPR/Cfpl systems, including both nuclease and/or transcription factor systems.

Accordingly, in certain embodiments the methods described herein the Cas protein isCpf1 from any bacterial species or functional portion thereof. In some aspects, Cpf1 is a *Francisella novicida* U112 protein or a functional portion thereof. In some aspects, Cpf1 is a *Acidaminococcus* sp. BV3L6 protein or a functional portion thereof. In some aspects, Cpf1 is a Lachnospiraceae bacterium ND2006 protein or a function portion thereof.

In certain embodiments, Cas protein may be a "functional portion" or "functional derivative" of a naturally occurring Cas protein, or of a modified Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity (e.g., endonuclease activity) in common with a corresponding native sequence polypeptide. As used herein, "functional portion" refers to a portion of a Cas polypeptide that retains its ability to complex with at least one ribonucleic acid (e.g., guide RNA (gRNA)) and cleave a target polynucleotide sequence. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional portion comprises a combination of operably linked Cpf1 protein functional domains selected from the group consisting of a DNA binding domain, at least one RNA binding domain, a helicase domain, and an endonuclease domain. In some embodiments, the functional domains form a complex. In some embodiments, a functional portion of the Cas9 protein comprises a functional portion of a RuvC-like domain. In some embodiments, a functional portion of the Cas9 protein comprises a functional portion of the HNH nuclease domain. In some embodiments, a functional portion of the Cpf1 protein comprises a functional portion of a RuvC-like domain.

In certain embodiments a biological activity contemplated herein is the ability of the functional derivative to to introdncue a double strand break (DSB) at a desired target site in a genomic DNA. The term "derivative" encompasses both amino acid sequence variants of polypeptide, covalent modifications, and fusions thereof. In some aspects, a functional derivative may comprise a single biological property of a naturally occurring Cas protein. In other aspects, a function derivative may comprise a subset of biological properties of a naturally occurring Cas protein.

In view of the foregoing, the term "Cas polypeptide" as used herein encompasses a full-length Cas polypeptide, an enzymatically active fragment of a Cas polypeptide, and enzymatically active derivatives of a Cas polypeptide or fragment thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically, recombinantly expressed, or by a combination of these procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In some embodiments, a Cas protein comprises one or more amino acid substitutions or modifications. In some embodiments, the one or more amino acid substitutions comprises a conservative amino acid substitution. In some instances, substitutions and/or modifications can prevent or reduce proteolytic degradation and/or extend the half-life of the polypeptide in a cell. In some embodiments, the Cas protein can comprise a peptide bond replacement (e.g., urea, thiourea, carbamate, sulfonyl urea, etc.). In some embodiments, the Cas protein can comprise a naturally occurring amino acid. In some embodiments, the Cas protein can comprise an alternative amino acid (e.g., D-amino acids, beta-amino acids, homocysteine, phosphoserine, etc.). In some embodiments, a Cas protein can comprise a modification to include a moiety (e.g., PEGylation, glycosylation, lipidation, acetylation, end-capping, etc.).

In certain embodiments the Cas proteins used in the constructs described herein may be mutated to alter functionality. Illustrative selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227.

In certain embodiments the Cas proteins (e.g., Cas9 protein) comprise truncated Cas proteins. In one illustrative, but non-limiting, embodiment, the Cas9 comprises only the domain responsible for interaction with the crRNA or sgRNA and the target DNA.

In certain embodiments the Cas proteins comprising the constructs described herein comprise a Cas protein, or truncation thereof, fused to a different functional domain. In some aspects, the functional domain is an activation or a repression domain. In other aspects, the functional domain is a nuclease domain. In some embodiments, the nuclease domain is a FokI endonuclease domain (see, e.g. Tsai (2014) *Nat. Biotechnol.* doi:10.1038/nbt.2908). In some embodiments, the FokI domain comprises mutations in the dimerization domain.

Guide RNA (for CRISPR/Cas Endonucleases)

In various embodiments the constructs methods described herein involve the introduction into the desired cell(s) of one or more guide RNAs (gRNAs) along with the CRISPR/Cas endonuclease. In certain embodiments the CRISPR/Cas endonuclease and gRNA are encoded by a single nucleic acid that is introduced into the cell. In certain embodiments the CRISPR/Cas endonuclease and gRNA are introduced into the cell as a ribonucleoprotein complex. In certain embodiments the complex comprise a Cas protein attached to a single guide RNA.

A nucleic acid molecule that binds to a class 2 CRISPR/Cas endonuclease (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA."

In various embodiments the guide RNA provides target specificity to the complex (the RNP complex) by including a targeting segment, which includes a guide sequence (also referred to herein as a targeting sequence), which typically comprise a nucleotide sequence that is complementary to a sequence of a target nucleic acid A guide RNA can be referred to by the protein to which it corresponds. For example, when the class 2 CRISPR/Cas endonuclease is a Cas9 protein, the corresponding guide RNA can be referred to as a "Cas9 guide RNA." Likewise, as another example, when the class 2 CRISPR/Cas endonuclease is a Cpf1 protein, the corresponding guide RNA can be referred to as a "Cpf1 guide RNA."

In some embodiments, a guide RNA includes two separate nucleic acid molecules (or two sequenced within a single molecule): an "activator" and a "targeter" and is referred to herein as a "dual guide RNA", a "double-molecule guide RNA", a "two-molecule guide RNA", or a "dgRNA." In some embodiments, the guide RNA is one molecule (e.g., for some class 2 CRISPR/Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

Cas9 Guide RNA

A nucleic acid molecule that binds to a Cas9 protein and targets the complex to a specific location (e.g., CD40L 5' UTR) within a target nucleic acid is referred to herein as a "Cas9 guide RNA." In certain embodiments a Cas9 guide RNA (can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule.

In various embodiments the first segment (targeting segment) of a Cas9 guide RNA typically includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a Cas9 polypeptide. The protein-binding segment of a subject Cas9 guide RNA typically includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the Cas9 guide RNA (the guide sequence of the Cas9 guide RNA) and the target nucleic acid A Cas9 guide RNA and a Cas9 protein form a complex (e.g., bind via non-covalent interactions). The Cas9 guide RNA provides target specificity to the complex by including a targeting segment, which includes a guide sequence (a nucleotide sequence that is complementary to a sequence of a target nucleic acid). The Cas9 protein of the complex provides the site-specific activity (e.g., cleavage activity or an activity provided by the Cas9 protein when the Cas9 protein is a Cas9 fusion polypeptide, i.e., has a fusion partner). In other words, the Cas9 protein is guided to a target nucleic acid sequence (e.g., a target sequence in a chromosomal nucleic acid, e.g., a chromosome; a target sequence in an extrachromosomal nucleic acid, e.g., an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the Cas9 guide RNA.

The "guide sequence" also referred to as the "targeting sequence" of a Cas9 guide RNA can be modified so that the Cas9 guide RNA can target a Cas9 protein to any desired sequence of any desired target nucleic acid, with the exception that the protospacer adjacent motif (PAM) sequence can be taken into account. Thus, for example, a Cas9 guide RNA can have a targeting segment with a sequence (a guide sequence) that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a Cas9 guide RNA includes two separate nucleic acid molecules: an "activator" and a "targeter" and is referred to herein as a "dual Cas9 guide RNA", a "double-molecule Cas9 guide RNA", or a "two-molecule Cas9 guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

In various embodiments a Cas9 guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) typically comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator/tracrRNA) typically comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the Cas9 guide RNA. As such, each targeter molecule can be said to have a corresponding activator molecule (which has a region that hybridizes with the targeter). In various embodiments the targeter molecule additionally provides the targeting segment. Thus, in various embodiments, a targeter and an activator molecule (as a corresponding pair) can hybridize to form a Cas9 guide RNA. The exact sequence of a given crRNA or tracrRNA molecule is characteristic of the species in which the RNA molecules are found. A subject dual Cas9 guide RNA can include any corresponding activator and targeter pair.

The term "activator" or "activator RNA" is used herein to mean a tracrRNA-like molecule (tracrRNA: "trans-acting CRISPR RNA") of a Cas9 dual guide RNA (and therefore of a Cas9 single guide RNA when the "activator" and the "targeter" are linked together by, e.g., intervening nucleotides). Thus, for example, a Cas9 guide RNA (dgRNA or sgRNA) typically comprises an activator sequence (e.g., a tracrRNA sequence). A tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a Cas9 dual guide RNA (and therefore of a Cas9 single guide RNA when the "activator" and the "targeter" are linked together, e.g., by intervening nucleotides). Thus, for example, a Cas9 guide RNA (dgRNA or sgRNA) typically comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, in various embodiments, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

In various embodiments a Cas9 guide RNA can also be said to include 3 parts: (i) a targeting sequence (a nucleotide sequence that hybridizes with a sequence of the target nucleic acid); (ii) an activator sequence (as described above) (in some cases, referred to as a tracr sequence); and (iii) a sequence that hybridizes to at least a portion of the activator sequence to form a double stranded duplex. A targeter has (i) and (iii); while an activator has (ii).

A Cas9 guide RNA (e.g., a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter typically comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) typically comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a Cas9 guide RNA. The particular sequence of a given naturally existing crRNA or tracrRNA molecule is characteristic of the species in which the RNA molecules are found. Examples of suitable activator and targeter are well known in the art.

In various embodiments a Cas9 guide RNA (e.g., a dual guide RNA or a single guide RNA) can be comprised of any corresponding activator and targeter pair.

Targeting Segment of a Cas9 Guide RNA

The first segment of a subject guide nucleic acid typically includes a guide sequence (e.g., a targeting sequence)(a nucleotide sequence that is complementary to a sequence (a target site) in a target nucleic acid). In other words, the targeting segment of a subject guide nucleic acid can interact with a target nucleic acid (e.g., double stranded DNA (dsDNA)) in a sequence-specific manner via hybridization (i.e., base pairing). As such, the nucleotide sequence of the targeting segment may vary (depending on the target) and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid such as genomic DNA).

In certain embodiments the targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

The nucleotide sequence (the targeting sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 18 nt or more.

For example, in certain embodiments, the targeting sequence of the targeting segment that is complementary to a target sequence of the target nucleic acid can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 75 nt, from 18 to 60 nt, from 18 to 50 nt, from 18 to 35 nt, from 18 to 30 nt, from 18 to 25 nt, from 18 to 22 nt, or from 18 to 20 nt). In some cases, the targeting sequence of the targeting segment that is complementary to a target sequence of the target nucleic acid has a length of from 15 nt to 30 nt. In some cases, the targeting sequence of the targeting segment that is complementary to a target sequence of the target nucleic acid has a length of from 15 nt to 25 nt. In some cases, the targeting sequence of the targeting segment that is complementary to a target sequence of the target nucleic acid has a length of from 18 nt to 30 nt. In some cases, the targeting sequence of the targeting segment that is complementary to a target sequence of the target nucleic acid has a length of from 18 nt to 25 nt. In some cases, the targeting sequence of the targeting segment that is complementary to a target sequence of the target nucleic acid has a length of from 18 nt to 22 nt. In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

In certain embodiments the percent complementarity between the targeting sequence (guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 17 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 18 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the 17 contiguous 5'-most nucleotides of the target site of the target nucleic acid and as low as 0% or more over the remainder. In such a case, the targeting sequence can be considered to be 17 nucleotides in length. In some cases, the percent complementarity between the targeting sequence of the targeting segment and the target site of the target nucleic acid is 100% over the 18 contiguous 5'-most nucleotides of the target site of the target nucleic acid and as low as 0% or more over the remainder. In such a case, the targeting sequence can be considered to be 18 nucleotides in length.

Protein-Binding Segment of a Cas9 Wuide RNA

The protein-binding segment of a subject Cas9 guide RNA typically interacts with a Cas9 protein. The Cas9 guide RNA guides the bound Cas9 protein to a specific nucleotide sequence within target nucleic acid via the above mentioned targeting segment. The protein-binding segment of a Cas9 guide RNA typically comprises two stretches of nucleotides that are complementary to one another and hybridize to form a double stranded RNA duplex (dsRNA duplex). Thus, the protein-binding segment can include a dsRNA duplex. In some cases, the protein-binding segment also includes stem loop 1 (the "*nexus*") of a Cas9 guide RNA. For example, in some cases, the activator of a Cas9 guide RNA (dgRNA or sgRNA) includes (i) a duplex forming segment that contributes to the dsRNA duplex of the protein-binding segment; and (ii) nucleotides 3' of the duplex forming segment, e.g., that form stem loop 1 (the "nexus"). For example, in some cases, the protein-binding segment includes stem loop 1 (the "nexus") of a Cas9 guide RNA. In some cases, the protein-binding segment includes 5 or more nucleotides (nt) (e.g., 6 or more, 7 or more, 8 or more, 9 or more, 10 or more, 11 or more, 12 or more, 15 or more, 20 or more, 30 or more, 40 or more, 50 or more, 60 or more, 70 or more, 75 or more, or 80 or more nt) 3' of the dsRNA duplex (where 3' is relative to the duplex-forming segment of the activator sequence).

The dsRNA duplex of the guide RNA (sgRNA or dgRNA) that forms between the activator and targeter is sometimes referred to herein as the "stem loop". In addition, the activator (activator RNA, tracrRNA) of many naturally existing Cas9 guide RNAs (e.g., S. pygogenes guide RNAs) has 3 stem loops (3 hairpins) that are 3' of the duplex-forming segment of the activator. The closest stem loop to the duplex-forming segment of the activator (3' of the duplex forming segment) is called "stem loop 1" (and is also referred to herein as the "nexus"); the next stem loop is called "stem loop 2" (and is also referred to herein as the "hairpin 1"); and the next stem loop is called "stem loop 3" (and is also referred to herein as the "hairpin 2").

In some cases, a Cas9 guide RNA (sgRNA or dgRNA) (e.g., a full length Cas9 guide RNA) has stem loops 1, 2, and 3. In some cases, an activator (of a Cas9 guide RNA) has stem loop 1, but does not have stem loop 2 and does not have stem loop 3. In some cases, an activator (of a Cas9 guide RNA) has stem loop 1 and stem loop 2, but does not have stem loop 3. In some cases, an activator (of a Cas9 guide RNA) has stem loops 1, 2, and 3.

In some cases, the activator (e.g., tracr sequence) of a Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the additional nucleotides 3' of the duplex forming segment form stem loop 1. In some cases, the activator (e.g., tracr sequence) of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment. In some cases, the activator (activator RNA) of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment.

In some cases, the activator (e.g., tracr sequence) of a Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the stretch of nucleotides 3' of the duplex forming segment has a length in a range of from 5 to 200 nucleotides (nt) (e.g., from 5 to 150 nt, from 5 to 130 nt, from 5 to 120 nt, from 5 to 100 nt, from 5 to 80 nt, from 10 to 200 nt, from 10 to 150 nt, from 10 to 130 nt, from 10 to 120 nt, from 10 to 100 nt, from 10 to 80 nt, from 12 to 200 nt, from 12 to 150 nt, from 12 to 130 nt, from 12 to 120 nt, from 12 to 100 nt, from 12 to 80 nt, from 15 to 200 nt, from 15 to 150 nt, from 15 to 130 nt, from 15 to 120 nt, from 15 to 100 nt, from 15 to 80 nt, from 20 to 200 nt, from 20 to 150 nt, from 20 to 130 nt, from 20 to 120 nt, from 20 to 100 nt, from 20 to 80 nt, from 30 to 200 nt, from 30 to 150 nt, from 30 to 130 nt, from 30 to 120 nt, from 30 to 100 nt, or from 30 to 80 nt). In some cases, the nucleotides of the 3' tail of an activator RNA are wild type sequences. It will be recognized that a number of different alternative sequences can be used.

Examples of various Cas9 proteins and Cas9 guide RNAs (as well as information regarding requirements related to protospacer adjacent motif (PAM) sequences present in targeted nucleic acids) can be found in the art (see, e.g., Jinek et al. (2012) *Science,* 337(6096): 816-821; Chylinski et al. (2013) *RNA Biol.* 10(5):726-737; Ma et al., (2013) *Biomed. Res. Int.* 2013: 270805; Hou et al. (2013) *Proc. Natl. Acad. Sci. USA,* 110(39): 15644-15649; Pattanayak et al. (2013) *Nat. Biotechnol.* 31(9): 839-843; Qi et al. (2013) *Cell,* 152(5): 1173-1183; Wang et al. (2013) *Cell,* 153(4): 910-918; Chen et. al. (2013) *Nucl. Acids Res.* 41(20): e19; Cheng et. al. (2012) *Cell Res.* 23(10): 1163-1171; Cho et. al. (2013) *Genetics,* 195(3): 1177-1180; DiCarlo et al. (2013) *Nucl. Acids Res.* 41(7): 4336-4343; Dickinson et. al. (2013) *Nat. Meth.* 10(10): 1028-1034; Ebina et. al. (2013) *Sci. Rep.* 3: 2510; Fujii et. al. (2013) *Nucl. Acids Res.* 41(20): e187; Hu et. al. (2013) *Cell Res.* 23(11): 1322-1325; Jiang et. al. (2013) *Nucl. Acids Res.* 41(20): e188; Larson et. al. (2013) *Nat. Protoc.* 8(11): 2180-2196; Mali et. at. (2013) *Nat. Meth.* 10(10): 957-963; Nakayama et. al. (2013) *Genesis,* 51(12): 835-843; Ran et. al. (2013) *Nat. Protoc.* 8(11): 2281-2308; Ran et. al. (2013) *Cell* 154(6): 1380-1389; Walsh et. al. (2013) *Proc. Natl. Acad. Sci. USA,* 110(39): 15514-15515; Yang et. al. (2013) *Cell,* 154(6): 1370-1379; Briner et al. (2014) *Mol. Cell,* 56(2): 333-339; and U.S. Patents and Patent Applications: U.S. Pat. Nos. 8,906,616; 8,895,308; 8,889,418; 8,889,356; 8,871,445; 8,865,406; 8,795,965; 8,771,945; 8,697,359; 2014/0068797; 2014/0170753; 2014/0179006; 2014/0179770; 2014/0186843; 2014/0186919; 2014/0186958; 2014/0189896; 2014/0227787; 2014/0234972; 2014/0242664; 2014/0242699; 2014/0242700; 2014/0242702; 2014/0248702; 2014/0256046; 2014/0273037; 2014/0273226; 2014/0273230; 2014/0273231; 2014/0273232; 2014/0273233; 2014/0273234; 2014/0273235; 2014/0287938; 2014/0295556; 2014/0295557; 2014/0298547; 2014/0304853; 2014/0309487; 2014/0310828; 2014/0310830; 2014/0315985; 2014/0335063; 2014/0335620; 2014/0342456; 2014/0342457; 2014/0342458; 2014/0349400; 2014/0349405; 2014/0356867; 2014/0356956; 2014/0356958; 2014/0356959; 2014/0357523; 2014/0357530; 2014/0364333; and 2014/0377868; all of which are incorporated herein by reference in their entirety.

In certain embodiments alternative PAM sequences may also be utilized, where a PAM sequence can be NAG as an alternative to NGG (Hsu (2014) supra.) using an *S. pyogenes* Cas9. Additional PAM sequences may also include those lacking the initial G (see, e.g., Sander and Joung (2014) *Nature Biotech* 32(4):347). In addition to the *S. pyogenes* encoded Cas9 PAM sequences, other PAM sequences can be used that are specific for Cas9 proteins from other bacterial sources. For example, the PAM sequences shown below in Table 2 (adapted from Sander and Joung, supra., and Esvelt et al. (2013) *Nat. Meth.* 10(11): 1116) are specific for these Cas9 proteins:

TABLE 2

Illustrative PAM sequences from various species.

| Species | PAM | SEQ ID NO |
|---|---|---|
| *S. pyogenes* | NGG | |
| *S. pyogenes* | NAG | |
| *S. mutans* | NGG | |
| *S. thermophilius* | NGGNG | 15 |
| *S. thermophilius* | NNAAAW | 16 |
| *S. thermophilius* | NNAGAA | 17 |
| *S. thermophilius* | NNNGATT | 18 |
| *C. jejuni* | NNNNACA | 19 |
| *N. meningitides* | NNNNGATT | 20 |
| *P. multocida* | GNNNCNNA | 21 |
| *F. novicida* | NG | |

Thus, in certain embodiments, a suitable target sequence for use with a *S. pyogenes* CRISPR/Cas system can be chosen according to the following guideline: [n17, n18, n19, or n20](G/A)G (SEQ ID NO:22). Alternatively, in certain embodiments, the PAM sequence can follow the guideline G[n17, n18, n19, n20](G/A)G (SEQ ID NO:23). For Cas9 proteins derived from non-*S. pyogenes* bacteria, the same guidelines may be used where the alternate PAMs are substituted in for the *S. pyogenes* PAM sequences.

Guide RNAs Corresponding to Type V and Type VI CRISPR/Cas Endonucleases (e.g., Cpf1 Guide RNA)

A guide RNA that binds to a type V or type VI CRISPR/Cas protein (e.g., Cpf1, C2c1, C2c2, C2c3), and targets the complex to a specific location within a target nucleic acid is referred to herein generally as a "type V or type VI CRISPR/Cas guide RNA". An example of a more specific term is a "Cpf1 guide RNA."

In various embodiments a type V or type VI CRISPR/Cas guide RNA (e.g., cpf1 guide RNA) can have a total length of from 30 nucleotides (nt) to 200 nt, e.g., from 30 nt to 180 nt, from 30 nt to 160 nt, from 30 nt to 150 nt, from 30 nt to 125 nt, from 30 nt to 100 nt, from 30 nt to 90 nt, from 30 nt to 80 nt, from 30 nt to 70 nt, from 30 nt to 60 nt, from 30 nt to 50 nt, from 50 nt to 200 nt, from 50 nt to 180 nt, from 50 nt to 160 nt, from 50 nt to 150 nt, from 50 nt to 125 nt, from 50 nt to 100 nt, from 50 nt to 90 nt, from 50 nt to 80 nt, from 50 nt to 70 nt, from 50 nt to 60 nt, from 70 nt to 200 nt, from 70 nt to 180 nt, from 70 nt to 160 nt, from 70 nt to 150 nt, from 70 nt to 125 nt, from 70 nt to 100 nt, from 70 nt to 90 nt, or from 70 nt to 80 nt). In some cases, a type V or type VI CRISPR/Cas guide RNA (e.g., cpf1 guide RNA) has a total length of at least 30 nt (e.g., at least 40 nt, at least 50 nt, at least 60 nt, at least 70 nt, at least 80 nt, at least 90 nt, at least 100 nt, or at least 120 nt).

In some cases, a Cpf1 guide RNA has a total length of 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, or 50 nt.

Like a Cas9 guide RNA, a type V or type VI CRISPR/Cas guide RNA (e.g., cpf1 guide RNA) can include a target nucleic acid-binding segment and a duplex-forming region (e.g., in some cases formed from two duplex-forming segments, i.e., two stretches of nucleotides that hybridize to one another to form a duplex)

In various embodiments the target nucleic acid-binding segment of a type V or type VI CRISPR/Cas guide RNA (e.g., cpf1 guide RNA) can have a length of from 15 nt to 30 nt, e.g., 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt. In some cases, the target nucleic acid-binding segment has a length of 23 nt. In some cases, the target nucleic acid-binding segment has a length of 24 nt. In some cases, the target nucleic acid-binding segment has a length of 25 nt.

In certain embodiments the guide sequence of a type V or type VI CRISPR/Cas guide RNA (e.g., cpf1 guide RNA) can have a length of from 15 nt to 30 nt (e.g., 15 to 25 nt, 15 to 24 nt, 15 to 23 nt, 15 to 22 nt, 15 to 21 nt, 15 to 20 nt, 15 to 19 nt, 15 to 18 nt, 17 to 30 nt, 17 to 25 nt, 17 to 24 nt, 17 to 23 nt, 17 to 22 nt, 17 to 21 nt, 17 to 20 nt, 17 to 19 nt, 17 to 18 nt, 18 to 30 nt, 18 to 25 nt, 18 to 24 nt, 18 to 23 nt, 18 to 22 nt, 18 to 21 nt, 18 to 20 nt, 18 to 19 nt, 19 to 30 nt, 19 to 25 nt, 19 to 24 nt, 19 to 23 nt, 19 to 22 nt, 19 to 21 nt, 19 to 20 nt, 20 to 30 nt, 20 to 25 nt, 20 to 24 nt, 20 to 23 nt, 20 to 22 nt, 20 to 21 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt). In some cases, the guide sequence has a length of 17 nt. In some cases, the guide sequence has a length of 18 nt. In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt. In some cases, the guide sequence has a length of 24 nt.

In certain embodiments the guide sequence of a type V or type VI CRISPR/Cas guide RNA (e.g., cpf1 guide RNA) can have 100% complementarity with a corresponding length of target nucleic acid sequence. The guide sequence can have less than 100% complementarity with a corresponding length of target nucleic acid sequence. For example, the guide sequence of a type V or type VI CRISPR/Cas guide RNA (e.g., cpf1 guide RNA) can have 1, 2, 3, 4, or 5 nucleotides that are not complementary to the target nucleic acid sequence. For example, in some cases, where a guide sequence has a length of 25 nucleotides, and the target nucleic acid sequence has a length of 25 nucleotides, in some cases, the target nucleic acid-binding segment has 100% complementarity to the target nucleic acid sequence. As another example, in some cases, where a guide sequence has a length of 25 nucleotides, and the target nucleic acid sequence has a length of 25 nucleotides, in some cases, the target nucleic acid-binding segment has 1 non-complementary nucleotide and 24 complementary nucleotides with the target nucleic acid sequence. As another example, in some cases, where a guide sequence has a length of 25 nucleotides, and the target nucleic acid sequence has a length of 25 nucleotides, in some cases, the target nucleic acid-binding segment has 2 non-complementary nucleotides and 23 complementary nucleotides with the target nucleic acid sequence.

In certain embodiments the duplex-forming segment of a type V or type VI CRISPR/Cas guide RNA (e.g., cpf1 guide RNA) (e.g., of a targeter RNA or an activator RNA) can have a length of from 15 nt to 25 nt (e.g., 15 nt, 16 nt, 17 nt, 18 nt, 19 nt, 20 nt, 21 nt, 22 nt, 23 nt, 24 nt, or 25 nt).

The RNA duplex of a type V or type VI CRISPR/Cas guide RNA (e.g., cpf1 guide RNA) can have a length of from 5 base pairs (bp) to 40 bp (e.g., from 5 to 35 bp, 5 to 30 bp, 5 to 25 bp, 5 to 20 bp, 5 to 15 bp, 5-12 bp, 5-10 bp, 5-8 bp, 6 to 40 bp, 6 to 35 bp, 6 to 30 bp, 6 to 25 bp, 6 to 20 bp, 6 to 15 bp, 6 to 12 bp, 6 to 10 bp, 6 to 8 bp, 7 to 40 bp, 7 to 35 bp, 7 to 30 bp, 7 to 25 bp, 7 to 20 bp, 7 to 15 bp, 7 to 12 bp, 7 to 10 bp, 8 to 40 bp, 8 to 35 bp, 8 to 30 bp, 8 to 25 bp, 8 to 20 bp, 8 to 15 bp, 8 to 12 bp, 8 to 10 bp, 9 to 40 bp, 9 to 35 bp, 9 to 30 bp, 9 to 25 bp, 9 to 20 bp, 9 to 152 b9 to 12 bp, 9 to 10 bp, 10 to 40 bp, 10 to 35 bp, 10 to 30 bp, 10 to 25 bp, 10 to 20 bp, 10 to 15 bp, or 10 to 12 bp).

As an illustrative, but non-limiting example, a duplex-forming segment of a Cpf1 guide RNA can comprise a nucleotide sequence selected from (5' to 3'): AAUUUCUACUGUUGUAGAU (SEQ ID NO:24), AAUUUCUGCUGUUGCAGAU (SEQ ID NO:25), AAUUUCCACUGUUGUGGAU (SEQ ID NO:26), AAUUCCUACUGUUGUAGGU (SEQ ID NO:27), AAUUUCUACUAUUGUAGAU (SEQ ID NO:28), AAUUUCUACUGCUGUAGAU (SEQ ID NO:29), AAUUUCUACUUUGUAGAU (SEQ ID NO:30), AAUUUCUACUUGUAGAU (SEQ ID NO:31), and the like. The guide sequence can then follow (5' to 3') the duplex forming segment.

Examples and guidance related to type V or type VI CRISPR/Cas endonucleases and guide RNAs (as well as information regarding requirements related to protospacer adjacent motif (PAM) sequences present in targeted nucleic acids) can be found in the art (see, e.g., Zetsche et al. (2015) *Cell,* 163(3): 759-771; Makarova et al. (2015) *Nat. Rev. Microbiol.* 13(11): 722-736; Shmakov et al. (2015) *Mol. Cell,* 60(3): 385-397; and the like).

Methods of utilizing a CRISPR/Cas9 system to introduce a corrective donor nucleic acid into the CD40LG 5' UTR are illustrated in Example 1, and methods of utilizing a CRISPR/Cas9 system to introduce a corrective donor nucleic acid into the BTK gene are illustrated in Example 2. The constructs and methods described therein are illustrate and non-limiting. Using the teachings provided herein, methods utilizing different CRISPR/Cas endonucleases and gRNAs will be available to one of skill in the art.

Zinc Finger Endonucleases.

In certain embodiments the targeting endonuclease can be a zinc finger nuclease (ZFN). Typically, a zinc finger nuclease comprises a DNA binding domain (e.g., zinc finger) and a cleavage domain (e.g., nuclease), both of which are described below.

Zinc Finger Binding Domain.

Zinc finger binding domains may be engineered to recognize and bind to any nucleic acid sequence of choice (see, e.g., Beerli et al. (2002) *Nat. Biotechnol.* 20: 135-141; Pabo et al. (2001) *Ann. Rev. Biochem.* 70: 313-340; Isalan et al. (2001) *Nat. Biotechnol.* 19: 656-660; Segal et al. (2001) *Curr. Opin. Biotechnol.* 12: 632-637; Choo et al. (2000) *Curr. Opin. Struct. Biol.* 10: 411-416; Zhang et al. (2000) *J. Biol. Chem.* 275(43): 33850-33860; Doyon et al. (2008) *Nat. Biotechnol.* 26: 702-708; and Santiago et al. (2008) *Proc. Natl. Acad. Sci. USA,* 105: 5809-5814). An engineered zinc finger binding domain can have a novel binding specificity compared to a naturally-occurring zinc finger protein. Engineering methods include, but are not limited to, rational design and various types of selection. Rational design includes, for example, using databases comprising doublet, triplet, and/or quadruplet nucleotide sequences and individual zinc finger amino acid sequences, in which each doublet, triplet or quadruplet nucleotide sequence is associated with one or more amino acid sequences of zinc fingers which bind the particular triplet or quadruplet sequence (see, e.g., U.S. Pat. Nos. 6,453,242 and 6,534,261, and the like). As an example, the algorithm described in U.S. Pat. No. 6,453,242 may be used to design a zinc finger binding domain to target a preselected sequence. Alternative methods, such as rational design using a nondegenerate recognition code table can also be used to design a zinc finger binding domain to target a specific sequence (see, e.g., Sera et al. (2002) *Biochemistry* 41: 7074-7081; and the like). Publically available web-based tools for identifying target sites in DNA sequences and designing zinc finger binding domains are found, inter alia, at zincfingertools.org and zifit.partners.org/ZiFiT/(see also Mandell et al. (2006) *Nucl.*

*Acida Res.* 34: W516-W523; Sander et al. (2007) *Nucl. Acida Res.* 35: W599-W605; and the like).

A zinc finger binding domain may be designed to recognize and bind a DNA sequence ranging from about 3 nucleotides to about 21 nucleotides in length, for example, from about 9 to about 18 nucleotides in length. Each zinc finger recognition region (i.e., zinc finger) typically recognizes and binds three nucleotides. In certain embodiments, the zinc finger binding domains of suitable targeted zinc finger nucleases comprise at least three zinc finger recognition regions (i.e., zinc fingers). The zinc finger binding domain, however, may comprise four, or five, or six, or more zinc finger recognition regions. A zinc finger binding domain may be designed to bind to any suitable target DNA sequence (see, e.g., U.S. Pat. Nos. 6,607,882; 6,534,261, 6,453,242, and the like.

Illustrative methods of selecting a zinc finger recognition region include, but are not limited to phage display and two-hybrid systems, and are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237y. In addition, enhancement of binding specificity for zinc finger binding domains has been described, for example, in WO 02/077227.

Zinc finger binding domains and methods for design and construction of fusion proteins (and polynucleotides encoding same) are known to those of skill in the art and are described in detail in U.S. Patent Application Publication Nos. 2005/0064474 and 2006/0188987. Zinc finger recognition regions and/or multi-fingered zinc finger proteins may be linked together using suitable linker sequences, including for example, linkers of five or more amino acids in length (see, e.g., U.S. Pat. Nos. 6,479,626; 6,903,185; and 7,153, 949) for non-limiting examples of linker sequences of six or more amino acids in length.

Cleavage Domain.

A zinc finger nuclease also typically includes a cleavage domain. The cleavage domain portion of the zinc finger nuclease may be obtained from any endonuclease or exonuclease. Non-limiting examples of endonucleases from which a cleavage domain may be derived include, but are not limited to, restriction endonucleases and homing endonucleases (see, e.g., New England Biolabs catalog (neb-.com); Belfort et al. (1997) *Nucleic Acids Res.* 25:3379-3388; and the like). Additional enzymes that cleave DNA are known (e.g., S1 Nuclease; mung bean nuclease; pancreatic DNase I; micrococcal nuclease; yeast HO endonuclease). In certain embodiments one or more of these enzymes (or functional fragments thereof) may be used as a source of cleavage domains.

In certain embodiments, a cleavage domain also may be derived from an enzyme or portion thereof, as described above, that requires dimerization for cleavage activity. Two zinc finger nucleases may be required for cleavage, as each nuclease comprises a monomer of the active enzyme dimer. Alternatively, a single zinc finger nuclease can comprise both monomers to create an active enzyme dimer. As used herein, an "active enzyme dimer" is an enzyme dimer capable of cleaving a nucleic acid molecule. The two cleavage monomers may be derived from the same endonuclease (or functional fragments thereof), or each monomer may be derived from a different endonuclease (or functional fragments thereof).

In various embodiments when two cleavage monomers are used to form an active enzyme dimer, the recognition sites for the two zinc finger nucleases are preferably disposed such that binding of the two zinc finger nucleases to their respective recognition sites places the cleavage monomers in a spatial orientation to each other that allows the cleavage monomers to form an active enzyme dimer, e.g., by dimerizing. As a result, the near edges of the recognition sites may be separated by about 5 to about 18 nucleotides. For instance, the near edges may be separated by about 5, 6, 7, 8, 9, 10, 11, 12, 13, 14, 15, 16, 17 or 18 nucleotides. It will however be understood that any integral number of nucleotides or nucleotide pairs can intervene between two recognition sites (e.g., from about 2 to about 50 nucleotide pairs or more). The near edges of the recognition sites of the zinc finger nucleases, such as for example those described in detail herein, may be separated by 6 nucleotides. In general, the site of cleavage lies between the recognition sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other (see, e.g., U.S. Pat. Nos. 5,356,802; 5,436,150, and 5,487,994; Li et al. (1992) *Proc. Natl. Acad. Sci. USA,* 89: 4275-4279; Li et al. (1993) *Proc. Natl. Acad. Sci. USA,* 90: 2764-2768. Thus, a zinc finger nuclease can comprise the cleavage domain from at least one Type IIS restriction enzyme and one or more zinc finger binding domains, which may or may not be engineered. Illustrative type IIS restriction enzymes are described for example in International Patent Publication No: WO 07/014,275. Additional restriction enzymes also contain separable binding and cleavage domains, and these also are contemplated by the present disclosure (see, e.g., Roberts et al. (2003) *Nucleic Acids Res.* 31:418-420.

An illustrative Type IIS restriction enzyme, whose cleavage domain is separable from the binding domain, is FokI. This particular enzyme is active as a dimer (Bitinaite et al. (1998) Proc. Natl. Acad. Sci. USA 95: 10, 570-10, 575). Accordingly, for the purposes of the present disclosure, the portion of the FokI enzyme used in a zinc finger nuclease is considered a cleavage monomer. Thus, for targeted double-stranded cleavage using a FokI cleavage domain, two zinc finger nucleases, each comprising a FokI cleavage monomer, may be used to reconstitute an active enzyme dimer. Alternatively, a single polypeptide molecule containing a zinc finger binding domain and two FokI cleavage monomers can also be used.

In certain embodiments the cleavage domain may comprise one or more engineered cleavage monomers that minimize or prevent homodimerization, as described, for example, in U.S. Patent Publication Nos. 2005/0064474, 2006/0188987, 2008/0131962, and the like. By way of non-limiting example, amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains. Illustrative engineered cleavage monomers of FokI that form obligate heterodimers include a pair in which a first cleavage monomer includes mutations at amino acid residue positions 490 and 538 of FokI and a second cleavage monomer that includes mutations at amino-acid residue positions 486 and 499 (see, e.g., Miller et al. (2007) *Nat. Biotechnol.* 25: 778-785; Szczpek et al. (2007) *Nat. Biotechnol.* 25: 786-793). For example, the Glu (E) at position 490 may be changed to Lys (K) and the lie (I) at position 538 may be changed to K in one domain (E490K, 1538K), and the Gin (Q) at position 486 may be changed to E and the I at position 499 may be changed to Leu (L) in another cleavage domain (Q486E, 1499L). In other aspects, modified FokI cleavage domains can include three amino acid changes (see, e.g., Doyon et al. (2011) *Nat. Methods,* 8: 74-81). For example, one modified FokI domain (which is termed ELD) can comprise Q486E, 1499L, N496D mutations and the other modified FokI domain (which is termed KKR) can comprise E490K, 1538K, H537R mutations.

Additional Domains.

In certain embodiments the zinc finger nuclease further comprises at least one nuclear localization signal or sequence (NLS). A NLS is an amino acid sequence that facilitates transport of the zinc finger nuclease protein into the nucleus of eukaryotic cells. In general, an NLS comprise a stretch of basic amino acids. Nuclear localization signals are known in the art (see, e.g., Makkerh et al. (1996) Curr. Biol. 6: 1025-1027; Lange et al. (2007) J. Biol. Chem. 282: 5101-5105). For example, in one embodiment, the NLS can be a monopartite sequence, such as PKKKRKV (SEQ ID NO:32) or PKKKRRV (SEQ ID NO:33). In another embodiment, the NLS can be a bipartite sequence. In still another embodiment, the NLS can be KRPAATKKAGQAKKKK (SEQ ID NO:34). In various embodiments the NLS can be located at the N-terminus, the C-terminus, or in an internal location of the zinc finger nuclease.

Although not required in the methods described herein, in certain embodiments, the zinc finger nuclease can also comprise at least one cell-penetrating domain. In one embodiment, the cell-penetrating domain can be a cell-penetrating peptide sequence derived from the HIV-1 TAT protein. As an example, the TAT cell-penetrating sequence can be GRKKRRQRRRPPQPKKKRKV (SEQ ID NO:35). In another embodiment, the cell-penetrating domain can be TLM (PLSSIFSRIGDPPKKKRKV, SEQ ID NO:36), a cell-penetrating peptide sequence derived from the human hepatitis B virus. In still another embodiment, the cell-penetrating domain can be MPG (GALFLGWLGAAGSTMGAPKKKRKV, SEQ ID NO:37) or GALFLGFLGAAGSTMGAWSQPKKKRKV, SEQ ID NO:38). In an additional embodiment, the cell-penetrating domain can be Pep-1 (KETWWETWWTEWS-QPKKKRKV, SEQ ID NO:39), VP22, a cell penetrating peptide from Herpes simplex virus, or a polyarginine peptide sequence. In various embodiments the cell-penetrating domain can be located at the N-terminus, the C-terminus, or in an internal location of the protein.

Cells to be Modified

In certain embodiments the cells that are modified using the methods described herein include, but are not limited to T cells including but not limited to primary XHIM patient CD4+ T cells, peripheral blood stem cells including but not limited to GCSF mobilized peripheral blood stem cells (PBSC), and various hematopoietic stem and progenitor cells (HPSCs) including, but not limited to CD34+ HSPCs.

However the methods described herein need not be limited to these cells. In certain embodiments other suitable cells include, but are not limited to various adult stem cells, cord blood cells, and induced pluripotent stem cells (IPSCs).

Systems/Kits.

In various embodiments a system for the treatment of X-Linked Hyper-IgM Syndrome ((XHIM) in a mammal (e.g., a human) is provided. In certain embodiments the system comprises: i) a first component comprising an AAV vector or a lentiviral vector containing a donor comprising a corrective CD40L cDNA flanked by homology arms; and ii) and a second component comprising one or more of the following: a TALEN mRNA targeting the CD40L 5' UTR; or a nucleic acid encoding a guide RNA (gRNA) and CRISPR/Cas endonuclease where the gRNA targets the CD40L 5' UTR; or a ribonucleoprotein (RNP) complex comping a guide RNA complexed to a CRISPR/Cas endonuclease, where the gRNA targets the CD40L 5' UTR. In certain embodiments the corrective CD40L cDNA comprises a corrective CD40L cDNA as described herein. In certain embodiments the corrective CD40L cDNA comprises a corrective CD4L cDNA as described herein in a viral vector (e.g., lentiviral vector, AAV vector, etc.). In certain embodiments the second component comprises a targeted endonuclease as described herein and, when required by the endonuclease, a guide RNA as described herein. In certain embodiments the system comprises a third component comprising an AAV helper protein or a nucleic acid encoding an AAV helper protein as described herein.

In certain embodiments the first component and second component, and third component when present, are disposed within a mammalian cell as described herein. In certain embodiments the cell is a hematopoietic stem or progenitor cell (HSPC). In certain embodiments the cell is a CD34+ hematopoietic stem or progenitor cell (HSPC). In certain embodiments the cell is a peripheral blood stem cell (PBSC) (e.g., a G-CSF mobilized peripheral blood stem cell (PBSC)). In certain embodiments the cell is a CD34+ cell.

In certain embodiments the first component and second component, and third component when present, are components of a kit. In certain embodiments component is disposed within a container comprising said kit. In certain embodiments the kit comprises instructional materials teaching the use of the components of a kit to insert a corrective cDNA into the CD40L gene.

While the instructional materials in the various kits typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials

EXAMPLES

The following examples are offered to illustrate, but not to limit the claimed invention.

Example 1

Tar2Eted Gene Insertion for the Treatment of X-Linked Hyper-12M Syndrome

X-linked hyper-IgM syndrome (XHIM) is a primary immunodeficiency due to mutations in the CD40 ligand gene resulting in defects of immunoglobulin class switch recombination and somatic hypermutation. Previous gene therapy-based studies have investigated the use of retroviral vectors for delivery of CD40L cDNA, but abnormal lymphoproliferation was observed in mouse models due to uncontrolled expression of the gene, highlighting the need for alternative strategies. Here, we demonstrate the ability of both the Transcription Activator-Like Effector Nucleases and Clustered Regularly Interspaced Short Palindromic Repeats-associated protein 9 nuclease platforms to allow homology directed repair-mediated integration of a normal copy of the CD40L cDNA delivered by Adeno-Associated Virus at the 5'UTR of the gene. Site-specific insertion of the donor sequence downstream of the endogenous CD40L enhancer and promoter maintains physiologic expression of CD40L while overriding all reported downstream mutations responsible for the disease. Gene modification can be achieved at high levels in cell lines and XHIM patient-derived T cells, but importantly, comparable rates of site-specific integration can be attained in human hematopoietic stem and progenitor cells (HSPC), which are multipotent and self-renewing. Manipulated HSPC engraft in immunodeficient mice at rates similar to mock-treated cells with clinically-relevant frequencies of site-specific gene insertion providing the foundation for a permanent curative therapy in XHIM patients.

Results.

TALEN-Mediated Gene Modification at CD40L in Cell Lines

The CD40L locus was targeted using several TALEN pairs cleaving within the 5'UTR of the CD40LG gene (FIG. 1, panel A). In K562 cell lines, electroporation with TALEN expression plasmids resulted in 32±3% allelic disruption using TALEN 2 as measured by Surveyor nuclease assay (CEL I) and significantly less with TALEN 1 and TALEN 3 (FIG. 1, panel B). All additional studies were therefore performed using TALEN 2. As a model for targeted gene integration, a 1500 bp plasmid donor was developed containing green fluorescent protein (GFP) reporter gene, lacking its own promoter and flanked by 30 homology sequences that flank the TALEN cut site (FIG. 1, panel C). Co-electroporation of K562 cells with the TALEN and GFP donor plasmids resulted in targeted gene insertion as demonstrated by ‘In-Out’ PCR, designed with the forward primer binding upstream of the 5' homology arm and the reverse primer binding within the GFP sequence (FIG. 1, panel D). Introduction of the TALEN 2 expression plasmid and the GFP donor to Jurkat T cells, a CD40L-expressing T cell leukemia line, achieved up to 12% overall GFP expression by flow cytometry. GFP expression of gene-modified Jurkat cells was maintained long term in culture, demonstrating permanent and stable gene integration (FIG. 1, panel E). Incubation of treated cells with phytohemagglutinin (PHA) to stimulate lymphocyte proliferation and increase CD40L expression upregulated GFP expression in a dose responsive manner, suggesting that the GFP cassette was integrated under control of the endogenous CD40LG promoter (FIG. 1, panels F-G).

TALEN and CRISPR-Cas9 Mediated Gene Correction at CD40LG in XHIM Patient-Derived T Lymphocytes Following demonstration of targeted integration at CD40LG in cell lines, the potential to modify primary XHIM T lymphocytes and restore CD40L expression was evaluated in vitro. CD4+ T cells derived from XHIM patients were electroporated with in vitro transcribed TALEN mRNA and transduced with either an integrase-deficient lentivirus (IDLV) or adeno-associated virus serotype 6 (AAV6) vector containing a corrective hCD40L cDNA cassette flanked by homology arms. The cDNA donor is codon-optimized/-divergent and contains the 3' UTR of the CD40L gene, as stability of the CD40L mRNA transcript is dependent on binding of a polypyrimidine tract binding protein (PTB) to the 3'UTR (see, e.g., Anderson, 2010; Saifuddin, Yang, & Covey, 2013). Additionally, PTB binding to the 3'UTR plays an important role in activated T cell viability and proliferation (Covey, Porta, & Nicodemos, 2015), which must be maintained for long-lasting immune correction in vivo (Vavassori 2009).

Figure 2:
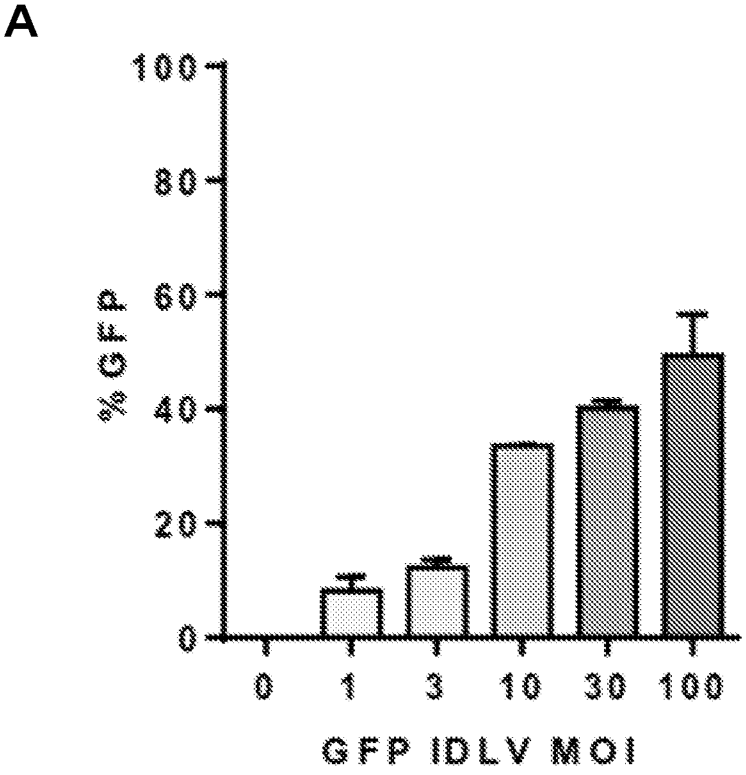
FIG. 2, panels A-D. Targeted integration in XHIM T cells of a CD40 ligand cDNA donor delivered by an integration-defective lentiviral vector (IDLV). Panel A) Primary XHIM patient CD4+ T cells were stimulated with antibodies to CD3/CD28 and assessed for permissiveness to IDLV transduction using a GFP-expressing IDLV at a range of MOI. Panel B) XHIM CD4+ T cells were electroporated with TALEN mRNA and transduced with an IDLV carrying a codon-optimized CD40L cDNA (MOI 100). CD40L expression was measured by flow cytometry 3-5 days later. Panel C) In-Out PCR using primers spanning two adjacent exons within the CD40L cDNA was used to detect the presence of site-specific cDNA integrants (n=4 biological replicates). Panel D) Site-specific integrations of the cDNA donor were quantified using ddPCR. Error bars represent mean±SD. *p<0.05, **p<0.01 (unpaired t-test). n=2-4 biological replicates.

To first evaluate the transduction efficiency of T cells by IDLV vectors, primary T cells were incubated with an IDLV expressing GFP at a range of multiplicity of infection (MOI). Flow cytometric analysis 24 hours later demonstrated GFP expression in a dose responsive manner, with >50% of cells positive for GFP at an MOI of 100 (FIG. 2, panel A). In experiments using a CD40L cDNA IDLV donor, control samples (mock treated, TALEN only, and cDNA donor IDLV only) demonstrated no CD40L expression by flow cytometric analysis with or without immune stimulation. XHIM T lymphocytes treated with both TALEN 2 mRNA and cDNA donor IDLV (MOI 100) expressed only minimal (<1%) CD40L expression by flow cytometry, even upon anti-hCD3/anti-hCD28 stimulation (FIG. 2, panel B). Exon-spanning PCR utilizing a reverse primer overlying two adjacent codons present only in the cDNA cassette demonstrated targeted integration through gel electrophoresis, quantified at rates of <0.5% by digital droplet PCR (ddPCR) (FIG. 2, panels C-D).

Figure 3:
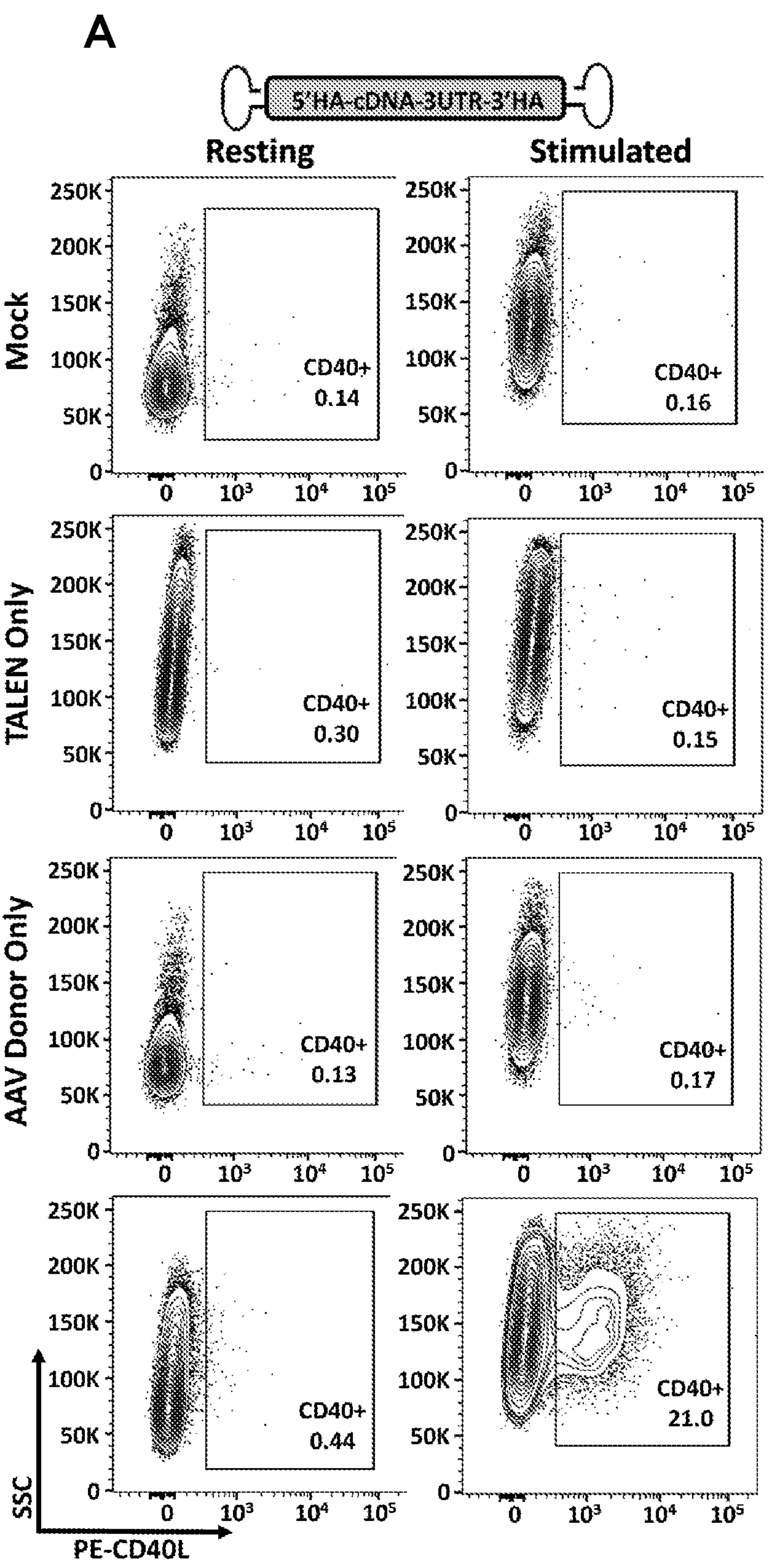
FIG. 3, panels A-E, illustrates targeted integration in XHIM T cells of the CD40L cDNA donor delivered by an adeno-associated virus virus (AAV6). Panel A) Primary XHIM patient CD4+ T-cells electroporated with TALEN mRNA and transduced with an AAV6 codon-divergent CD40L cDNA donor. Expression of CD40L was measured by flow cytometry in resting T cells and after stimulation with anti-hCD3/anti-hCD28 microbeads. Panel B) CD40L expression trends by flow cytometry in XHIM T cells electroporated with TALEN and AAV donor and re-stimulated over time in culture. Panel C) Average gene modification rates as measured by flow cytometry and ddPCR. n=8-10 biological replicates. Panel D) Comparison of gene integration as measured by ddPCR versus expression of CD40L by flow cytometry. Panel E) CD40L function was assessed by binding to a fluorescent-labeled chimeric CD40-muIg and flow cytometry. Statistics in C and D were analyzed by Wilcoxon Rank-Sum Test. NS=not significant.

In contrast, XHIM T cells transduced with an identical codon-optimized cDNA donor packaged as an AAV6 vector following TALEN 2 mRNA electroporation expressed low levels of CD40L at baseline, with upregulation to >20% CD40L expression upon anti-hCD3/anti-hCD28 immune stimulation (FIG. 3, panel A). Viability and fold expansion of treated T cells as measured by trypan blue was similar in control and treatment groups (FIG. 4, panels A-B). Additionally, when cells were rested in culture and analyzed at one week intervals, CD40L expression consistently returned to baseline levels and responded physiologically to re-stimulation (FIG. 3, panel B). In addition to measuring restoration of CD40L expression by flow cytometry, targeted cDNA integrants were directly quantified through ddPCR by using a forward primer upstream of both the CD40L gene and the 5' homology arm of the donor (to avoid amplification of non-integrated donor), a reverse primer binding the sequence spanning exons 1 and 2 of the codon-optimized donor, and a probe specific for the codon-optimized CD40LG exon 1 (FIG. 3, panel C). CD40L expression by flow cytometry and gene modification by ddPCR correlated very closely (FIG. 3, panel D), suggesting that ddPCR analysis could be used as a surrogate measurement for CD40L gene correction in experiments utilizing healthy donor cells. Restoration of CD40L was dose responsive at various AAV6 MOI without significantly affecting viability and fold expansion (FIG. 4, panels C-E). Furthermore, corrected XHIM T cells demonstrated normal receptor-binding activity to recombinant chimeric CD40-muIg, a functional assessment of CD40L used clinically to detect all patients with defects in CD40L (Abraham & Aubert, 2016; and (FIG. 3, panel E).

Figure 5:
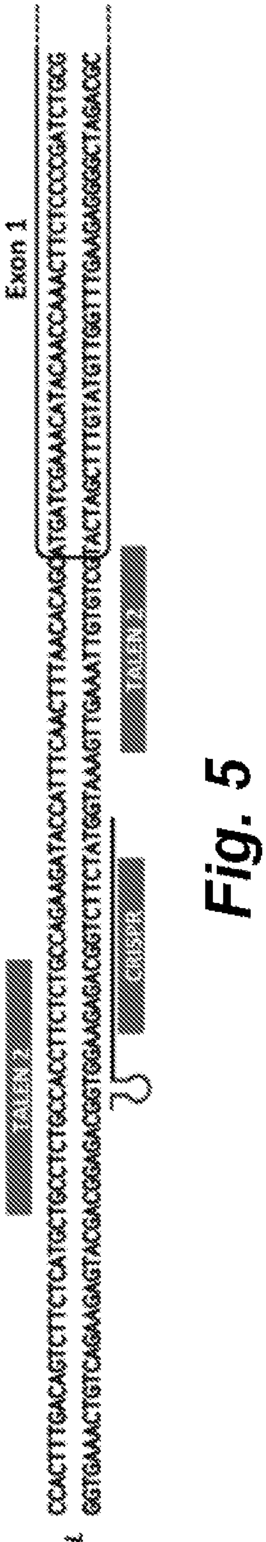
FIG. 5, panels A-E, illustrates CRISPR/Cas9 mediated gene editing of the CD40L gene in XHIM T cells. Panel A) CRISPR gRNA targeting a similar location in the 5'UTR sequence of the CD40LG gene (SEQ ID NO:1) as TALEN 2. Panel B) Allelic disruption rates in XHIM CD4+ T cells using gRNA with Cas9 mRNA or complexed to recombinant Cas9 protein as RNP were measured by Surveyor nuclease assay (n=6-10 biological replicates in primary T cells from 4 different XHIM patients). Panel C) Gene integration rates in primary XHIM T cells measured by flow cytometry and ddPCR (n=2-4 biological replicates, 2 XHIM T cell donors). Panel D) CD40-muIg binding by CRISPR/Cas9 modified XHIM T cells to assess CD40L protein function. Panel E) Expression of CD40L by flow cytometry in XHIM T cells treated with CRISPR/Cas9 RNA or RNP and AAV donor and re-stimulated over time in culture. Statistics in Panels B and C analyzed by Wilcoxon Rank-Sum Test. NS=not significant.

The CRISPR/Cas9 platform was also evaluated in XHIM primary T cells using a guide RNA (gRNA) targeting a similar region in the 5' UTR of CD40LG as targeted by TALEN 2 (FIG. 5, panel A). Allelic disruption rates in XHIM T cells averaged 30.6% and 33.7% delivered as either in vitro transcribed gRNA with Cas9 mRNA or complexed to Cas9 protein as ribonucleoproteins (RNP), respectively (FIG. 5, panel B). AAV6 cDNA donor transduction following gRNA/Cas9 electroporation resulted in slightly lower gene modification rates compared to those treated with TALEN mRNA (FIG. 5, panel C). Despite this, modified T cells showed restored CD40L function as measured by receptor-binding to chimeric CD40-muIg by flow cytometry (FIG. 5, panel D) and could be rested and re-stimulated for weeks after gene modification (FIG. 5, panel E).

TALEN- and CRISPR/Cas9-Mediated Gene Correction at CD40LG in Healthy Donor-Derived Mobilized Peripheral Blood CD34+ Cells Given the difficulty accessing XHIM CD34+ HSC, this work was translated into healthy donor-derived human granulocyte-colony stimulating factor (G-CSF) mobilized peripheral blood stem cells (PBSC) to evaluate the potential of this platform to be used as a curative therapy. Electroporation of peripheral blood CD34+ cells with TALEN mRNA resulted in allelic disruption rates of 29.1±7.8% (n=8 biological replicates, 4 PBSC donors). When transduced with the CD40L cDNA AAV6 donor, gene modification rates averaged 13.2±3.4% as measured by ddPCR (FIG. 6, panel A). Gene integration in PBSC was correlated with increasing AAV MOI up to le5 with decreasing viability and expansion of cells at higher vector concentrations (FIG. 7, panels A-C).

Additional CRISPR gRNA were also evaluated in PBSC with delivery of the gRNA/Cas9 as in vitro transcribed Cas9 mRNA or conjugated to Cas9 protein as RNP complexes through electroporation (FIG. 6, panel B). Allelic disruption rates of ~30-40% using CRISPR 3 were consistently achieved in HSC as measured by surveyor endonuclease assay and were used in all further CRISPR based experiments (FIG. 6, panel C). Coupled with AAV6 CD40L cDNA transduction, average targeted gene insertion rates of 16.2±4.2% (gRNA, Cas9 mRNA) and 20.8±6.6% (RNP) were attained irrespective of PBSC donor source (FIG. 6, panel D). Cell viability and fold expansion with trypan blue 24 hours after electroporation and transduction were generally decreased in samples treated with both nuclease and AAV. Decreased viability was more apparent in those treated with Cas9 mRNA compared to RNP (FIG. 7, panels D-G).

The role of adenovirus helper proteins in enhancing CRISPR-mediated gene targeting as well as increasing AAV transduction have been previously reported in cell lines and primary human T cells (Gwiazda et al., 2016; Lentz & Samulski, 2015). To evaluate if these proteins can augment targeted gene integration at CD40LG in HSC, E4Orf6 and E1B55K H354 mutant adenoviral serotype 5 helper proteins were co-introduced as in vitro transcribed mRNA during electroporation with TALENs or CRISPRs. Gene modification rates measured as CD40L expression by flow cytometry or quantified by ddPCR were increased in samples treated with helper protein ($p<0.0001$) regardless of nuclease platform (FIG. 6, panels E-F). Addition of the adenoviral helper protein mRNA did not significantly affect cell viability and fold expansion 24 hours post-electroporation (FIG. 7, panels D-G).

In Vitro Differentiation of Gene-Modified HSPC

Figure 8:
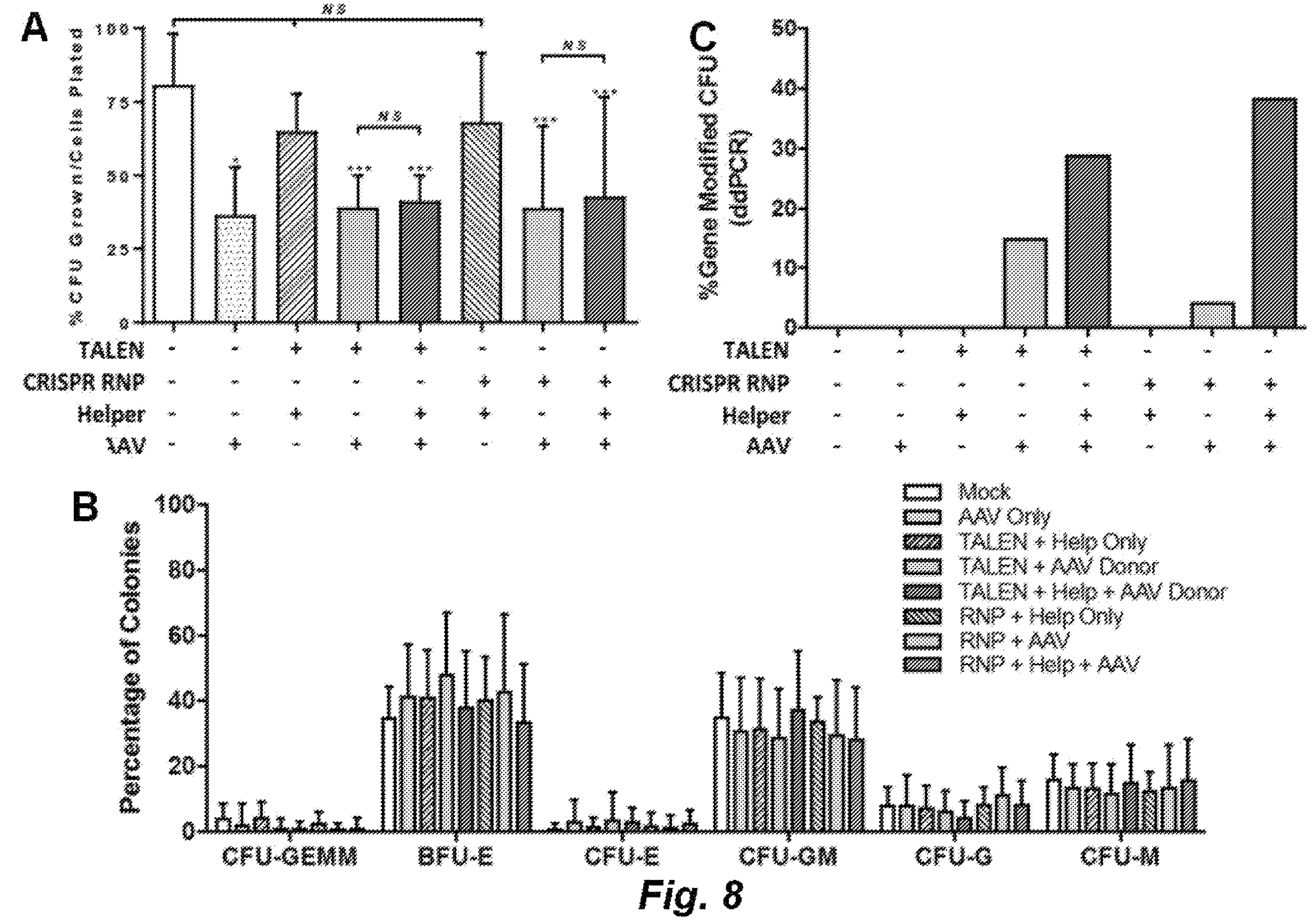
FIG. 8, panels A-C, show the results of a colony-forming unit (CFU) assay of CD34+ PBSC after treatment with TALEN or CRISPR, AAV6 CD40L cDNA donor and adenoviral helper proteins. Panel A) PBSC treated with combinations of TALEN mRNA or CRISPR RNP, AAV6 CD40L cDNA donor and the adenoviral E4orf6/Elb55k helper proteins plated in methylcellulose CFU assay. Numbers of colonies were enumerated after 12-14 days. Statistics were analyzed by Wilcoxon Rank-Sum Test. Data are presented as mean±SD. n=4 experiments, 3 PBSC donors. $*p \leq 0.05$, NS=not significant. Panel B) The percentages of the different colony types formed were enumerated. CFU-GEMM (CFU-granulocyte/erythroid/macrophage/megakaryocyte), BFU-E (burst-forming unit-erythroid), CFU-E (CFU-erythroid), CFU-GM (CFU-granulocyte/macrophage), CFU-G (CFU-granulocyte), CFU-GM (CFU-macrophage). Panel C) The percentages of CFU gene-modified at the CD40LG 5' UTR were determined by ddPCR analysis of genomic DNA from individual CFU.

To ensure that gene-modified CD34+ PBSC retain the capacity to differentiate into multiple erythro-myeloid lineages, TALEN mRNA and CRISPR RNP electroporated PBSC transduced with the AAV6 cDNA donor were cultured in methylcellulose medium containing cytokines that promote stem cell differentiation in the colony forming unit (CFU) progenitor cell assay. The clonogenic potential of samples treated with either TALENs or CRISPRs and also transduced with AAV6 was lower compared to mock treated, although there was no difference between the nuclease platforms. The addition of adenoviral helper proteins did not affect colony formation (FIG. 8, panel A). All control, TALEN-, and CRISPR-Cas9 treatment arms produced similar frequencies of myeloid and erythroid clones (FIG. 8, panel B). Gene integration analysis of individual clones demonstrated editing frequencies comparable to cells cultured in short term in myeloid conditions, with similar increases in those treated with adenoviral helper proteins (FIG. 8, panel C).

In Vivo Assessment of Hematopoietic Repopulating Potential in NSG Mice

PBSC electroporated with TALEN mRNA or CRISPR RNP followed by transduction with the AAV6 cDNA donor were transplanted into sub-lethally irradiated NSG mice through intrahepatic injection between days of life 3 and 7. Following 12 or 20 week engraftment, bone marrow was analyzed for human CD45 engraftment, lineage development, and gene integration by ddPCR while human T cell differentiation was quantified in the thymus. Human engraftment as measured by percentage of hCD45+ over total CD45+ cells (human and murine) and lineage distribution was equivalent amongst mock and treatment groups in the bone marrow with similar rates of engraftment in the spleen and peripheral blood (FIG. 9, panels A-D).

Gene modification rates in samples of the bulk transplanted PBSC cultured in vitro as determined by ddPCR were 0% in mock, 21.0±3.7% in TALEN/AAV donor, 28.0±6.3% in TALEN/helper/AAV donor, 15.0±7.1% in RNP/AAV donor, and 27.6±4.0% in RNP/helper/AAV donor samples (FIG. 9, panel E).

Quantification of targeted integration rates 12-20 weeks later in the bone marrow of transplanted mice were 0% in mock, 4.5±4.5% in TALEN/AAV donor, 2.6±3.1% in TALEN/helper/AAV donor, 3.6±5.5% in RNP/AAV donor, and 2.9±4.8% in RNP/helper/AAV donor samples (FIG. 9, panel F). While adenoviral helper protein augmented gene integration rates in vitro in short term cultures, this effect was not maintained long term in NSG mice. In fact, levels of gene insertion in samples containing helper protein trended lower than their equivalent counterparts without helper protein, although this difference was not statistically significant ($p=0.97$ TALENs, $p=0.59$ CRISPR RNP).

Given the heterogeneity of stem cell populations at various stages of lineage commitment, long-term (LT) HSC, multi-potent progenitor (MPP), and progenitor populations were FACs sorted on the basis of surface markers CD34+CD38−CD45RA−CD90+, CD34+CD38−CD45RA−CD90−, and CD34+CD38+ respectively to evaluate if adenoviral helper proteins had differential effects on each of these populations. The percentage of gene integration was quantified by ddPCR in each of the populations and compared to the bulk CD34+ culture 24 hours after electroporation and AAV transduction (FIG. 6, panel G). Except for the MPP population, which had lower rates of gene editing in some treatment group likely due to low cell recovery following sorting, integration rates in the immunophenotypic LT-HSC were similar to that of the bulk and progenitor populations.

Thymic reconstitution occurred in about 60% of mice, with frequency of engraftment trending higher in those analyzed at 5 months compared to 3 months post-transplant, although this was not statistically significant (FIG. 10, panel A). Physiologic ratios of CD4+ and CD8+ T cells were found in all thymi with T cell reconstitution (FIG. 10, panel B). In mice analyzed at 3 months post-transplant, one thymus from each experimental arm was FACs sorted for CD4+ single positive, CD8+ single positive, and CD4+CD8+ double positive thymocytes. Cells were expanded by co-culturing with anti-hCD3/anti-hCD28 beads and were harvested 7 days later for genomic DNA isolation. Gene integration by ddPCR was not detected in any of the thymocyte populations. To evaluate if T cells developing from gene modified HSC require a longer period in vivo, some mice were kept until 5 months post-transplant. FACs sorting was again performed on 5 mice with high levels of hCD45+ cells and cultured in a similar fashion. Gene integration was detectable in all three T cell populations in two of five mice analyzed (FIG. 10, panel C). T cell receptor V beta repertoire was quantified by flow cytometry in one mouse from each arm and found to be equivalent amongst all treatment groups compared to mice transplanted with mock treated PBSC (FIG. 10, panel D).

Assessment of Nuclease Specificity and Characterization of HDR-Mediated Junctions The specificities of both TALENs and CRISPR gRNA were assessed using in silico prediction algorithms as well as unbiased genome-wide assays. In silico predicted TALEN off-target sites were identified using the PROGNOS (Predicted Report Of Genome-wide Nuclease Off-target Sites) tool(Fine, Cradick, Zhao, Lin, & Bao, 2014) and evaluated in K562 cells treated with TALEN expression plasmids. Allelic disruption was only detected on-target, with no differences in banding patterns between mock and TALEN treated samples for each of the predicted five off-target sites analyzed by CEL I (FIG. 11, panel A). In silico predicted off-target sites for CRISPR 3 were identified using the CRISPR Design Tool (crispr.mit.edu/about) (Hsu et al., 2013), and interrogation of these predicted off-target sites by Surveyor nuclease assay demonstrated no detectable gene disruption at the top three sites listed (FIG. 11, panel C).

Figure 12:
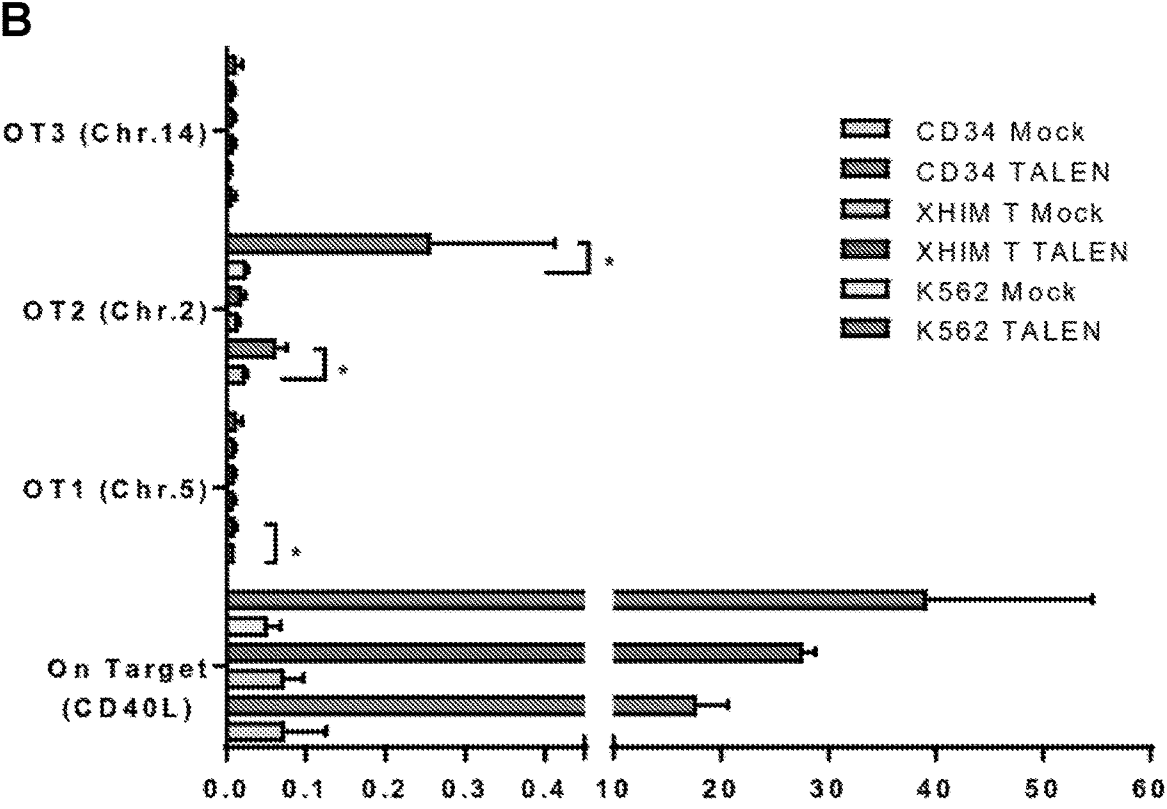
FIG. 12, panels A-E, shows the results of off-target analysis and characterization of HDR-Mediated Junctions. Panel A) Off-target sites as identified by GFP-IDLV trapping in TALEN-treated K562 cells. Allowing for homodimerization of TALEN arms, degree of homology to the on-target binding site is also illustrated.

Genome-wide profiling of off-target activity was also performed in TALEN and CRISPR treated K562 cells based on the propensity for exogenous DNA sequences to be trapped at sites of DSB, whether on- or off-target. For TALENs, a non-homologous IDLV was introduced to TALEN-treated cells in a method previously described (Gabriel et al., 2011). Clustered integration site analysis of captured IDLV revealed three off-target loci in chromosomes 5 (OT1), 2 (OT2), and 14 (OT3) at areas with relatively high levels of homology to the CD40L target (FIG. 12, panel A). While no allelic detection was detected by CEL I at these sites in K562 cells (FIG. 11, panel B), high-throughput sequencing of off-target sites in PBSC, XHIM CD4+ T cells, and K562 cells treated with TALEN mRNA (PBSC, XHIM T cell) or expression plasmids (K562) demonstrated statistically significant gene disruption at OT1 (chromosome 5) in PBSC and OT2 (chromosome 2) in PBSC and K562 cells compared to mock (FIG. 12, panel B). Off-target cleavage activities of CRISPR 3 were assessed similarly using capture of a short double-stranded oligodeoxynucleotide at DSBs through GUIDE-seq (Genome-Wide, Unbiased Identification of DSBs Enabled by Sequencing) (Tsai et al., 2015) with no off-target sites identified (FIG. 12, panel C).

Furthermore, the fidelity of editing the CD40LG locus was characterized by Sanger sequencing of the junctions between the homologous template and the endogenous DNA. Using a forward primer upstream of the 5' homology arm and a reverse primer spanning the codon-optimized donor, all TALEN and AAV6 cDNA donor treated samples were found to be sequence-perfect. In contrast, CRISPR-treated samples had only 33% of reads that were sequence perfect, with 51% containing indels in the 5'UTR and 16% with indels that extended into exon 1 (FIG. 12, panel D). To evaluate if this observation was due to re-cleavage of the integrated donor, cells were treated with a donor containing a modification of the PAM sequence from -TGG to -TAA (FIG. 12, panel E). With this change in the donor sequence, all integration events were found to be sequence perfect (FIG. 12, panel D).

DISCUSSION

Major advancements in the field of genome-editing over the last decade have allowed targeted gene therapy to become a realistic potential therapeutic option for monogenic diseases of the blood and immune systems. This is particularly applicable to defects in genes that require close regulation, and from a clinical standpoint, offers definitive treatment for individuals who are too chronically ill to undergo myeloablative doses of bone marrow conditioning and immune suppression or do not have an HLA-matched donor. Here we demonstrate an approach using both the TALEN and CRISPR/Cas9 platforms to allow site-specific incorporation of a human codon-divergent CD40L cDNA at the 5'UTR of the gene in both primary patient T lymphocytes and human CD34+ HSC, bypassing all known downstream disease-causing mutations and maintaining expression of the therapeutic gene under control of the endogenous CD40L promotor. In contrast to previous work using TALENs in differentiated T cells (Hubbard et al., 2016), we utilized XHIM patient T cells to validate gene editing reagents and focused on HSC-based genome-editing strategies which can provide permanent and robust immune reconstitution.

While either TALEN or CRISPR/Cas9 platforms can achieve good rates of gene editing in vitro, there have been to date no studies to deem one superior over the other. For this reason, both technologies were applied to primary T cells and HSC in short-term cultures followed by assessment of HSC long-term in vivo in NSG mice. As a first step, CD40L cDNA donor constructs and nuclease reagents were tested in primary XHIM patient-derived T lymphocytes. We were able to recapitulate the results of prior work using TALENs and also established that CRISPR/Cas9 could be used to reach high rates of targeted gene integration and restore physiologically-regulated CD40L expression and function in CD40L-deficient T cells.

In CD34+ HSC, even higher rates of targeted gene integration were consistently achieved, particularly using RNA-guided DNA endonucleases, across multiple G-CSF mobilized PBSC donors than could be attained in primary T cells. Cas9 delivered as either mRNA or as recombinant Cas9 protein directly complexed to the gRNA as RNP were equally efficient with similar effects on viability and fold expansion of cells when measured 24 hours after treatment. As recruitment of the Mre11/Rad51/NBS1 (MRN) DNA repair complex during AAV transduction is known to limit its activity, mutant adenoviral E4orf6 and Elb55k helper proteins were co-delivered to transiently degrade the MRN complex and allow AAV genomes to evade intranuclear detection (Lentz & Samulski, 2015; Yew, Kao, & Berk, 1990). Addition of adenoviral helper protein mRNA with the AAV CD40L cDNA donor consistently doubled cDNA donor integration rates in CD34+ PBSC assayed in vitro regardless of nuclease platform without changes to short-term viability, fold expansion, and clonogenic potential by CFU assay.

Despite significantly augmented rates of gene integration in HSC in vitro with the addition of adenoviral helper proteins, this benefit was not maintained long term in vivo in murine studies. In experiments sorting out LT-HSC (CD34+CD38−CD45RA−CD90+), MPP (CD34+CD38−CD45RA−CD90−), and progenitor (CD34+CD38+) stem cell populations, it appeared this result was not attributable to a lack of gene editing in the immunophenotypic LT-HSC population, with rates of targeted integration in the LT-HSC similar to those in the bulk stem cell population. Long-term engraftment in NSG may be from a more quiescent fraction of these cells that are more resistant to homologous recombination, which are unlikely affected by adenoviral helper proteins.

In general, CRISPRs showed higher on-target activity than TALENs targeting the 5'UTR of the CD40L gene. Additionally, the CRISPR sgRNA with the highest on target activity (CRISPR 3) also possessed higher specificity than TALEN 2, which had detectable levels of off-target activity at a relatively homologous site in the human genome. While there is currently no gold standard for detection of unwanted nuclease activity in clinical trials, we utilized cell-based assays such as IDLV capture and GUIDE-seq, which seem more physiologically relevant than purely in vitro assays. Additionally, high throughput sequencing results of TALEN OT1 and OT2 identified by IDLV capture demonstrated statistically significant off-target allelic disruption in PBSC treated with TALEN mRNA at OT1 and both PBSC and K562 samples treated with TALEN mRNA and expression plasmid, respectively, at OT2. The increased level of off-target activity in K562 cells may be due to the relatively prolonged presence of plasmid DNA compared to mRNA in cells and the ability of TALEN mRNA and protein to be continually transcribed and translated while the plasmid remains intact in the cell, illustrating that off-target activity can be directly affected by the reagents used. Careful titration of nuclease dose and use of RNPs in the case of CRISPR/Cas9 can be critical in minimizing unintended nuclease activity and important factors to consider in translating this work to the clinic.

Sequence analysis of the junction between the left homology arm and the endogenous 5' UTR demonstrated the presence of a high frequency of indels with CRISPRs but not with TALENs. The indels in association with gene insertion is likely due to re-cleavage of the nuclease target site after homologous recombination with the donor. The integrated donor would leave intact the PAM and gRNA recognition sequences, allowing a subsequent cycle of CRISPR/Cas9-mediated cutting. In contrast, targeted insertion of the cDNA donor would disrupt the proximity of the binding sites for the two members of the TALEN pair, avoiding re-cleavage. Indel formation after CRISPR-mediated targeted insertion could be completely eliminated by using a donor that had the PAM sequence eradicated by a two base-pair change, making the integrated gene resistant to CRISPR activity.

In the in vivo studies, G-CSF mobilized PBSC that were gene modified with either platform engrafted at levels equivalent to mock treated cells in the bone marrow, spleen, and peripheral blood of NSG mice analyzed at 3 months and 5 months post-transplantation. The fold decreases in gene modification from in vitro to in vivo studies are comparable to what has been reported by other groups using similar gene editing reagents in hematopoietic stem cells (De Ravin et al., 2016; Genovese et al., 2014; Hoban et al., 2015). Despite the decrease in editing rates in vivo, it is likely that the number of gene corrected T cells produced would be sufficient to allow some degree of class-switching to occur to significantly ameliorate or cure the disease, as only low levels of normal CD40L expression in vivo are needed to result in correction of the immune deficiency based on murine models(Brown et al., 1998; Sacco et al., 2000) and the observation of normal clinical phenotypes of female carriers with skewed lyonization towards the mutated CD40LG gene (Hollenbaugh et al., 1994).

While this work is limited to a single, rare primary immunodeficiency, successful translation to the clinic will have significant implications for all other monogenic diseases of the hematopoietic system. In all, the results reported here demonstrate the potential for developing a curative therapy for XHIM through site-specific gene editing. However, they also highlight many of the challenges in bringing targeted gene addition to the clinic. A key element will be to optimize the delivery of gene-editing reagents, all of which introduce some level of toxicity to hematopoietic stem cells. This is further complicated by inherent properties of the true, long-term HSC, which are most capable of bone marrow engraftment and long-term hematopoiesis, but are also fragile, rare, and relatively quiescent, favoring the non-homologous end joining pathway over homologous recombination during DNA damage. As we and others continue to address these issues, it is hoped that the high rates of gene modification currently achieved in vitro will be more directly translated to in vivo outcomes in animal models and ultimately in clinical trials of gene editing for XHIM affected individuals.

Methods

TALEN and CRISPR Construction

TALENs targeted to the CD40LG 5' untranslated region were designed with the online TAL Effector Nucleotide Targeter 2.0. program (Doyle 2012, Cermak 2011) and assembled using the Golden Gate TALEN kit (Addgene; Cambridge, MA) and Golden Gate TALEN assembly protocol. (Cermak 2011) TALENs were subsequently cloned into a pCAG mammalian expression vector. The T7 promoter was cloned into the vector preceding the TALEN sequence using a gene block containing the T7 promoter with the In-Fusion HD Cloning Kit (ClonTech Laboratories; Mountain View, CA). CRISPR single guide RNAs (sgRNA) were designed using the online design tool created by the Zhang Lab. Paired oligonucleotides for sgRNAs were synthesized (Integrated DNA Technologies; San Diego, CA), annealed, and cloned into the pX330-U6-Chimeric_BB-CBh-hSpCas9 expression vector (Addgene) as previously described (Cong L 2013) to express both the sgRNA and the *Streptococcus pyogenes* Cas9. For use as an in vitro mRNA transcription template, hSpCas9 from the pX330 plasmid was cloned into an in-house-modified pGEM-5Zf(+) plasmid (Promega; Madison, WI) that includes optimized 5' and 3' UTR sequences and a modified 3' UTR that encodes a run of 120 adenine nucleotides followed by an SpeI restriction site for linearization. (Warren L 2010).

In Vitro Transcription of TALEN mRNA, CRISPR gRNA, and Cas9 mRNA

TALEN expression plasmids were linearized with AgeI, purified with the PureLink PCR Purification Kit (Life Technologies; Waltham, MA), and used as the template for in vitro transcription using the mMESSAGE mMACHINE T7 Ultra Transcription Kit (ThermoFischer Scientific; Waltham, MA). The T7-Cas9 plasmid was linearized with SpeI and in vitro transcribed as above. gRNA were in vitro transcribed as single guide RNA (sgRNA) from a T7 promoter from either the pDR274 plasmid linearized with DraI using the MEGAshortscript T7 Transcription Kit (ThermoFisher Scientific) or from a PCR-generated DNA template using the HiScribe T7 Quick High Yield RNA Synthesis Kit (New England Biolabs; Ipswich, MA) (DeWitt & Wong, 2015).

Adenovirus 5 Helper Proteins

Adenovirus 5 helper proteins E4Orf6 and E1B55K H354 (Yew 1990) were ordered as commercially generated gblocks (Integrated DNA Technologies) and cloned into the modified pGEM-5Zf(+) plasmid downstream of the T7 promoter by Gibson Assembly (New England BioLabs). Expression plasmids were linearized with SpeI and used as templates for in vitro transcription as described above.

Donor Template Construction

The human codon-optimized CD40LG cDNA donor template was commercially synthesized (Integrated DNA Technologies) and contains all five exons (785 bp) along with the 3' UTR (944 bp) of the human CD40LG gene followed by the bGH polyA signal (24 bp). The cDNA donor sequence is flanked by a 5' homology arm that begins at the TALEN and CRISPR/Cas9 cut site and extends 162 bp upstream and a 3' homology arm that extends 405 bp downstream of the TALEN cut site. The 5' and 3' homology arms were amplified from human cord blood HSC-derived genomic DNA using primers 5'-ctttacgtaacgtttttgctgg-3' (SEQ ID NO:40) with 5'-agaagtttggttgtatgtttcgatcataaatggtatcttctggcagaga-3' (SEQ ID NO:41) and 5'-ccagaagataccatttcaactttaac-3' (SEQ ID NO:42) with 5'-gggcagagccaagatttga-3' (SEQ ID NO:43) respectively. Splice overlap PCR was used to stitch together the 5' homology arm and CD40LG cDNA with primers 5'-gccgccagtgtgctggaattcctttacgtaacgtttttgctgg-3' (SEQ ID NO:44) and 5'-cagcctgcaaggtgacactgttcagagtttgagtaagccaaagg-3' (SEQ ID NO:45). The 3'UTR and 3' homology arm fragment was incorporated similarly using primers 5'-acagtgtcaccttgcaggc-3' (SEQ ID NO:46) and 5'-gcagaattcgcccttgggcagagccaagatttga-3' (SEQ ID NO:47). The two PCR products were ligated and cloned into the PCR2.1 TOPO backbone using the In-Fusion HD Cloning Kit (Clontech). The entire CD40LG cDNA donor with flanking homology arms donor sequence was cloned into a previously established lentiviral backbone (Dull 1998) in reverse orientation to avoid splicing during packaging of the virus. Lentiviral vectors were packaged as integrase-defective lentiviral vectors using the p8.2(Int-) packaging plasmid and concentrated; titers were determined as described (Cooper 2011). The CD40LG cDNA donor with flanking homology arms was also cloned into an AAV vector plasmid (pX601, Addgene) and produced as an AAV serotype 6 (Virovek, Hayward CA).

Surveyor Nuclease Assay

Surveyor Nuclease Assay was used to determine TALEN induced site-specific allelic disruption at the 5'UTR of the CD40LG gene. A 400-500 base pair region surrounding the TALEN and CRISPR binding sites of the CD40LG gene 5' UTR was PCR amplified from 200 ng of genomic DNA from treated cells with primers 5'-gcaacgattgtgcgctctta-3' (SEQ ID NO:48) and 5'-acacagcaaaaagtgctgacc-3' (SEQ ID NO:49) using AccuPrime Taq Hi-Fi (ThermoFisher Scientific). Denaturation, reannealing, CEL I digestion, and electrophoretic and densitometry analysis were completed as described (Joglekar 2013).

Electroporation

K562 cells were cultured in RPMI 1640 (Mediatech; Tewksbury, MA) with 10% fetal bovine serum (Omega Scientific; Tarzana, CA), electroporated with the Lonza 4D-Nucleofector System (program FF-120) in SF Cell Line solution at a cell density of 2x105 cells per 20 uL reaction with 500-750 ng of either TALEN or CRISPR expression plasmids. XHIM patient derived peripheral blood mononuclear cells were obtained under a UCLA IRB-approved protocol (UCLA IRB #10-0011399) and cultured in RPMI with 20% fetal bovine serum, 1x glutamine/penicillin/streptomycin (Gemini Bio Products; Sacramento, CA), 10 ng/mL hIL-2 (R&D Systems; Minneapolis, MN) and Dynabeads Human T-Activator CD3/CD28 (ThermoFischer Scientific) to expand T lymphocytes for 5-7 days. One day prior to electroporation, CD4+ T lymphocytes were enriched from bulk CD3+ T cells by depletion of CD8+ lymphocytes using CD8 microbeads (Miltenyi Biotec 130-045-021; Bergisch Gladbach, Germany) passed through LD columns (Miltenyi Biotec). CD4+ T lymphocytes were electroporated using the ThermoFischer Neon Transfection System (1400V, lOms, 3 pulses) in Opti-MEM at a cell density of 4.5x107 cells/mL with either 1.5 ug of each TALEN arm as in vitro transcribed mRNA or 2.5 ug of in vitro transcribed CRISPR sgRNA and 2.5 ug Cas9 mRNA or 5 μg of CRISPR sgRNA and 50 pmol of Cas9 protein. Immediately post-electroporation, cells were transduced with codon-optimized cDNA IDLV or AAV6 vector. G-CSF mobilized peripheral blood CD34+ cells (HemaCare; Van Nuys, CA) were pre-stimulated for 48 hours in X-VIVO15 medium containing penicillin, streptomycin, glutamine, 50 ng/mL rhuSCF, 50 ng/mL rhuFlt-3 ligand, and 50 ng/mL rhuTPO (Peprotech; Rocky Hill, NJ). The CD34+ cells were then electroporated with the Harvard Apparatus BTX ECM 830 Square Wave Electroporator (255V, 5 msec, 1 pulse) in BTXpress buffer at a cell density of 2x106 cells/mL. Cells were transduced with donor AAV6 or IDLV after 10 minutes of rest at room temperature in X-VIVO15, penicillin, streptomycin, glutamine, and cytokines for 24 hours, at which point they were counted for viability and fold expansion and studied in vitro and in vivo.

Colony Forming Unit (CFU) Assay

CFU assays were performed using Methocult H4435 Enriched methylcellulose (StemCell Technologies, Vancouver, Canada. Cat. #04445) according to manufacturer's instructions with minor modifications. Briefly, 25 and 100 CD34+ PBSC were plated in duplicates into 35 mm gridded cell culture dishes. After 14 days of culture at 5% C02, 37° C. and humidified atmosphere, the different types of hematopoietic colonies were identified and counted. CFU were then plucked for genomic DNA isolation (NucleoSpin Tissue XS, Clontech Laboratories Inc., Mountain View, CA).

In vivo studies

NOD/SCID/γ-chainnull (NSG) mice (NOD.Cg.Prkdcscid Il2rgtm1Wjl/SzJ; stock no. 005557; Jackson Laboratory, Bar Harbor, ME) were housed in accordance with an approved protocol by the UCLA Office of Animal Research Committee. At all times animals were handled in laminar flow hoods and housed in a pathogen-free colony in a biocontainment vivarium. Newborn pups at 3-7 days of life of both genders were injected with 5-10×$10^5$ cells/pup via intrahepatic injection of unmodified or gene-modified human CD34-positive cells prepared as described above, one day after conditioning with 125cGy of sub-lethal body irradiation from a $^{137}$Ce source with attenuator, and allowed to engraft over 12-20 weeks as described (De Oliveira et al., 2013). At the end of each experiment, mice were sacrificed by $CO_2$ inhalation followed by cardiac puncture, and bone marrow, thymus, liver, spleen and bone marrow were harvested for assays.

Example 2

Optimization of the Corrective CD40L cDNA Donor Template

Site-specific gene integration of a codon-optimized CD40L cDNA sequence at either the 5'UTR or the 5' end of Exon 1 achieves correction of the CD40L defect by integrating a corrective cDNA cassette, overriding all downstream defects and maintaining regulated control of the transgene using the endogenous CD40L promoter. While integration of the codon-optimized cDNA donor in patient-derived XHIM T cells results in restored CD40L expression by flow cytometry, the level of expression, as measured by mean fluorescent intensity (MFI), is lower than that of stimulated T cells from healthy donors. Therefore, we investigated the addition of intronic elements that may be important for expression of the CD40L gene. In particular, DNase I hypersensitivity peak clusters were identified from ENCODE, as areas of open or accessible chromatin are functionally related to transcriptional activity. In addition, intronic elements can improve gene expression by impacting the rate of transcription, nuclear export, and transcript stability, termed "intron-mediated enhancement" (Shaul (2017) Int. J. Biochem. Cell. Biol. 91(Pt B):145-155.). It has also been reported that the terminal splice acceptor contained within the terminal intron provides RNA polymerase II with precise control over transcription termination in the beta-globin gene (Dye & Proudfoot (1999) Mol Cell. 3(3): 371-378. Combining these principles, we constructed a modified version of the original codon-optimized cDNA donor to include an approximately 1 kb region of intron 4 between exons 4 and 5. This region contains a DNase I hypersensitivity cluster that is highly conserved in vertebrates and is flanked by the endogenous intron 4 splice machinery which includes a 5' splice donor and a 3' splice acceptor preceded by the branch point and AG exclusion zone. A similar donor construct with a shorter segment of intron 4 but still containing the DNase I hypersensitivity site was also tested. The donor constructs are schematically illustrated in FIG. 22.

Each of the donors described above was cloned and packaged as AAV serotype 6 and evaluated in patient-derived XHIM patient T cells. Two to seven days after electroporation of nuclease and transduction with AAV6, XHIM T cells were stimulated with PMA/ionomycin and evaluated for CD40L expression by flow cytometry shown in FIG. 23.

Consistent with previous experiments, the base codon-optimized cDNA donor achieved restoration of CD40L expression in patient cells but at a lower level of expression compared to stimulated normal T cells from healthy donors. However, the addition of elements from the terminal intron significantly improved expression to levels of normal T cells.

In addition, the functionality of restored CD40L protein was also measured by receptor-binding to chimeric CD40-muIg by flow cytometry (FIG. 24).

As expected, CD40L function of XHIM T cells treated with the base cDNA donor was lower than that of normal T cells. In contrast, inclusion of intron 4 elements improved receptor binding to chimeric CD40-muIg to levels equivalent to that of healthy T cells.

In conclusion, we have identified that inclusion of intronic elements can improve expression of the transgene after site-specific gene integration. The micro-Int4 door has slightly improved CD40L expression and function, and can be used as an optimal donor cassette. The nano-Int4 donor, which has only slightly lower CD40L expression and function than micro-Int4 can be used in donor constructs that require addition of other elements (such as fluorescent markers) to keep the cassette within the packaging limit of adeno-associated viruses.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Sequence Listing
XHIM nano-Int4 Donor

SEQ ID NO: 6

```
CTTTACGTAACGTTTTTGCTGGGAGAGAAGACTACGAAGCACATTTTCCA
GGAAGTGTGGGCTGCAACGATTGTGCGCTCTTAACTAATCCTGAGTAAGG
TGGCCACTTTGACAGTCTTCTCATGCTGCCTCTGCCACCTTCTCTGCCAG
AAGATACCATTTCAACTTTAACACAGCATGATCGAAACATACAACCAAAC
TTCTCCCCGATCCGCCGCCACAGGCCTGCCTATCAGCATGAAGATCTTTA
TGTACCTGCTGACCGTGTTCCTGATCACCCAGATGATCGGCAGCGCCCTG
TTCGCCGTGTACCTGCACAGACGGCTGGACAAGATCGAGGACGAGCGGAA
CCTGCACGAGGACTTCGTGTTCATGAAGACCATCCAGCGGTGCAACACCG
GCGAGAGAAGCCTGAGCCTGCTGAACTGCGAGGAAATCAAGAGCCAGTTC
GAGGGCTTCGTGAAGGACATCATGCTGAACAAAGAGGAAACTAAGAAAGA
AAACAGCTTCGAGATGCAGAAGGGCGACCAGAACCCCCAGATTGCCGCCC
ACGTGATCAGCGAGGCCAGCAGCAAGACCACatctgGTAAGTCACACAGC
ATCTGAGCGGTAGCCACCCAAGGGGAAAGGCTGGGATGCCGGATCTTGTG
CCCTGATAGACCTAAGACTATCGAATAGGAATTATTTTTAAAAAGCTCA
AGGAAGCAAACACATCAGTACTTTCACTTTTCCTCAACCCTCACCCCCAT
CAGTCAGTCTAGCTTTCTGTGGGAGCTGAGATTTCAAGTCGGGTGCACAC
ACTACTTTGAACCCACTCAACATCTCAGCCGAGAAAATGGCACACTGTTG
GTGGGTACTCTGGCTTAGCCACAAGAATACTGGTACTTTCAAGTTGGTGG
CGCCCACTACAATGGGAGATCAAAACATACCGTGAAATGAGCACACAGTT
TATTTTCATACTTCCTTGCCTAATTTTAGTCCTTGCTGGGGGAGGCAGAT
CAGGTTTGCAACAGTTGTCAGAATGTGAACCATGCTCTGCTTCACCTCAC
CACAAACTTTCCCTTTCTTTGTAACAGtgttaCAGTGGGCCGAGAAGGGC
TACTACACCATGAGCAACAACCTCGTGACCCTGGAAAACGGCAAGCAGCT
GACAGTGAAGCGGCAGGGCCTGTACTACATCTACGCCCAAGTGACCTTCT
GCAGCAACAGAGAGGCCAGCTCCCAGGCCCCCTTTATCGCCAGCCTGTGC
CTGAAGTCCCCCGGCAGATTCGAGAGAATCCTGCTGAGAGCCGCCAACAC
CCACAGCAGCGCCAAGCCTTGTGGCCAGCAGTCTATCCACCTGGGCGGCG
TGTTCGAACTGCAGCCTGGCGCCTCCGTGTTCGTGAACGTGACCGATCCT
AGCCAGGTGTCCCACGGCACCGGCTTCACAAGCTTCGGACTGCTGAAGCT
GTGAACAGTGTCACCTTGCAGGCTGTGGTGGAGCTGACGCTGGGAGTCTT
CATAATACAGCACAGCGGTTAAGCCCACCCCCTGTTAACTGCCTATTTAT
AACCCTAGGATCCTCCTTATGGAGAACTATTTATTATACACTCCAAGGCA
TGTAGAACTGTAATAAGTGAATTACAGGTCACATGAAACCAAAACGGGCC
CTGCTCCATAAGAGCTTATATATCTGAAGCAGCAACCCCACTGATGCAGA
CATCCAGAGAGTCCTATGAAAAGACAAGGCCATTATGCACAGGTTGAATT
CTGAGTAAACAGCAGATAACTTGCCAAGTTCAGTTTTGTTTCTTTGCGTG
CAGTGTCTTTCCATGGATAATGCATTTGATTTATCAGTGAAGATGCAGAA
GGGAAATGGGGAGCCTCAGCTCACATTCAGTTATGGTTGACTCTGGGTTC
CTATGGCCTTGTTGGAGGGGGCCAGGCTCTAGAACGTCTAACACAGTGGA
```

-continued

GAACCGAAACCCCCCCCCCCCCCCGCCACCCTCTCGGACAGTTATTCATTC
TCTTTCAATCTCTCTCTCCATCTCTCTCTTTCAGTCTCTCTCTCTCAA
CCTCTTTCTTCCAATCTCTCTTTCTCAATCTCTCTGTTTCCCTTTGTCAG
TCTCTTCCCTCCCCCAGTCTCTCTTCTCAATCCCCCTTTCTAACACACAC
ACACACACACACACACACACACACACACACACACACACACACAGAGTCAG
GCCGTTGCTAGTCAGTTCTCTTCTTTCCACCCTGTCCCTATCTCTACCAC
TATAGATGAGGGTGAGGAGTAGGGAGTGCAGCCCTGAGCCTGCCCACTCC
TCATTACGAAATGACTGTATTTAAAGGAAATCTATTGTATCTACCTGCAG
TCTCCATTGTTTCCAGAGTGAACTTGTAATTATCTTGTTATTTATTTTTT
GAATaataaagacctcttaacattatcgTGCGGCCACTGGACTGCCCATC
AGCATGAAAATTTTTATGTATTTACTTACTGTTTTTCTTATCACCCAGAT
GATTGGGTCAGCACTTTTTGCTGTGTATCTTCATAGAAGGTTGGACAAGG
TAAGATGAACCACAAGCCTTTATTAACTAAATTTGGGGTCCTTACTAATT
CATAGGTTGGTTCTACCCAAATGATGGATGATGGTAGAAACCAAATAGAA
GAATGGTCTTGTGGCATAATGTTTGTTGCCTAGTCAATGAAGTCTCATAT
TCTTGTCTCTGGTTAGGATCTTGGGATCTGGAGTCAGACTGCCTGGGTTC
AAATCTTGGCTCTGCCCATACCATCTCTGTTATCCTGGGGCAAGTGCCTC
AGTTTCCACATCTGAGAAATGGGGATGGTATTGGTGTCCATTTCATAGAT
TAAGTGAGTTTAGCCTTGTAAAAAGCTT XHIM micro-Int4 Donor

SEQ ID NO: 11

CTTTACGTAACGTTTTTGCTGGGAGAGAAGACTACGAAGCACATTTTCCA
GGAAGTGTGGGCTGCAACGATTGTGCGCTCTTAACTAATCCTGAGTAAGG
TGGCCACTTTGACAGTCTTCTCATGCTGCCTCTGCCACCTTCTCTGCCAG
AAGATACCATTTCAACTTTAACACAGCATGATCGAAACATACAACCAAAC
TTCTCCCCGATCCGCCGCCACAGGCCTGCCTATCAGCATGAAGATCTTTA
TGTACCTGCTGACCGTGTTCCTGATCACCCAGATGATCGGCAGCGCCCTG
TTCGCCGTGTACCTGCACAGACGGCTGGACAAGATCGAGGACGAGCGGAA
CCTGCACGAGGACTTCGTGTTCATGAAGACCATCCAGCGGTGCAACACCG
GCGAGAGAAGCCTGAGCCTGCTGAACTGCGAGGAAATCAAGAGCCAGTTC
GAGGGCTTCGTGAAGGACATCATGCTGAACAAAGAGGAAACTAAGAAAGA
AAACAGCTTCGAGATGCAGAAGGGCGACCAGAACCCCCAGATTGCCGCCC
ACGTGATCAGCGAGGCCAGCAGCAAGACCACatctgGTAAGTCACACAGC
ATCTGAGCGGTAGCCACCCAAGGGGAAAGGCTGGGATGCCGAAGTCATGT
TACCTAATGGTTAAACTCCTCTTTTCCCCTGGGACCCAATTTACAAACCT
ACCCCTACAGTAAAGGGCGAGTCTTACCAGGTGGGATCTTGTGCCCTGAT
AGACCTAAGACTATCGAATAGGAATTATTTTTTAAAAAGCTCAAGGAAGC
AAACACATCAGTACTTTCACTTTTCCTCAACCCTCACCCCCATCAGTCAG
TCTAGCTTTCTGTGGGAGCTGAGATTTCAAGTCGGGTGCACACACTACTT
TGAACCCACTCAACATCTCAGCCGAGAAAATGGCACACTGTTGGTGGGTA
CTCTGGCTTAGCCACAAGAATACTGGTACTTTCAAGTTGGTGGCGCCCAC
TACAATGGGAGATCAAAACATACCGTGAAATGAGCACACAGTTTATTTTC -continued ATACTTCCTTGCCTAATTTTAGTCCTTGCTGGGGGAGGCAGATCAGGTTT
GCAACAGCATGATCAGGTAGGAAGAAATGGGGTCTTTTCTCTGTGCTGAG
GCTGAGCTAGGTAGACTGACAACTCTCTGACTTTGTAAAATTCAAGGCAA
GCAAGGTATTCATGGTAATATTAGCAAAAATTTGGTCCGAGTAATTTGGT
ATGTATAATTTATGATGTCAAATTTTGAAATCATTTGTGCCTTCTTAAGT
TCAAGGCAAATTGGCTATAAGAACTCTAACGAGAGAAAGAAACTCACTGT
GATCTCTTACTTTATTTAATCTTCACAAGTCTCTGAAATATGCTCCAATA
TGAGCCCCGTGTTGCAGATGAGGAACTGAAGCTCATGGAGATTTAGAGAC
TTGCCCAAGCTTAAATAGAGCCTAGATTGGAACATGGCTCTGTCTGACTC
TGAAGCCCATGGAAGGGGCCTTGAGAATCCATCCCTATACAAAGCCAATA
TCCAACATTAAACTATATTTTTTGTCAGAATGTGAACCATGCTCTGCTTC
ACCTCACCACAAACTTTCCCTTTCTTTGTAACAGtgttaCAGTGGGCCGA
GAAGGGCTACTACACCATGAGCAACAACCTCGTGACCCTGGAAAACGGCA
AGCAGCTGACAGTGAAGCGGCAGGGCCTGTACTACATCTACGCCCAAGTG
ACCTTCTGCAGCAACAGAGAGGCCAGCTCCCAGGCCCCCTTTATCGCCAG
CCTGTGCCTGAAGTCCCCCGGCAGATTCGAGAGAATCCTGCTGAGAGCCG
CCAACACCCACAGCAGCGCCAAGCCTTGTGGCCAGCAGTCTATCCACCTG
GGCGGCGTGTTCGAACTGCAGCCTGGCGCCTCCGTGTTCGTGAACGTGAC
CGATCCTAGCCAGGTGTCCCACGGCACCGGCTTCACAAGCTTCGGACTGC
TGAAGCTGTGAACAGTGTCACCTTGCAGGCTGTGGTGGAGCTGACGCTGG
GAGTCTTCATAATACAGCACAGCGGTTAAGCCCACCCCCTGTTAACTGCC
TATTTATAACCCTAGGATCCTCCTTATGGAGAACTATTTATTATACACTC
CAAGGCATGTAGAACTGTAATAAGTGAATTACAGGTCACATGAAACCAAA
ACGGGCCCTGCTCCATAAGAGCTTATATATCTGAAGCAGCAACCCCACTG
ATGCAGACATCCAGAGAGTCCTATGAAAAGACAAGGCCATTATGCACAGG
TTGAATTCTGAGTAAACAGCAGATAACTTGCCAAGTTCAGTTTTGTTTCT
TTGCGTGCAGTGTCTTTCCATGGATAATGCATTTGATTTATCAGTGAAGA
TGCAGAAGGGAAATGGGGAGCCTCAGCTCACATTCAGTTATGGTTGACTC
TGGGTTCCTATGGCCTTGTTGGAGGGGGGCCAGGCTCTAGAACGTCTAACA
CAGTGGAGAACCGAAACCCCCCCCCCCCCCGCCACCCTCTCGGACAGTTA
TTCATTCTCTTTCAATCTCTCTCTCCATCTCTCTCTTTCAGTCTCTCT
CTCTCAACCTCTTTCTTCCAATCTCTCTTTCTCAATCTCTCTGTTTCCCT
TTGTCAGTCTCTTCCCTCCCCCAGTCTCTCTTCTCAATCCCCCTTTCTAA
CACACACACACACACACACACACACACACACACACACACACACACACACA
GAGTCAGGCCGTTGCTAGTCAGTTCTCTTCTTTCCACCCTGTCCCTATCT
CTACCACTATAGATGAGGGTGAGGAGTAGGGAGTGCAGCCCTGAGCCTGC
CCACTCCTCATTACGAAATGACTGTATTTAAAGGAAATCTATTGTATCTA
CCTGCAGTCTCCATTGTTTCCAGAGTGAACTTGTAATTATCTTGTTATTT
ATTTTTTGAATaataaagacctcttaacattatcgTGCGGCCACTGGACT
GCCCATCAGCATGAAAATTTTTATGTATTTACTTACTGTTTTTCTTATCA -continued

CCCAGATGATTGGGTCAGCACTTTTTGCTGTGTATCTTCATAGAAGGTTG

GACAAGGTAAGATGAACCACAAGCCTTTATTAACTAAATTTGGGGTCCTT

ACTAATTCATAGGTTGGTTCTACCCAAATGATGGATGATGGTAGAAACCA

AATAGAAGAATGGTCTTGTGGCATAATGTTTGTTGCCTAGTCAATGAAGT

-continued

CTCATATTCTTGTCTCTGGTTAGGATCTTGGGATCTGGAGTCAGACTGCC

TGGGTTCAAATCTTGGCTCTGCCCATACCATCTCTGTTATCCTGGGGCAA

GTGCCTCAGTTTCCACATCTGAGAAATGGGGATGGTATTGGTGTCCATTT

CATAGATTAAGTGAGTTTAGCCTTGTAAAAAGCTT

What is claimed is:

1. A method of engraftment of edited T cells and/or stem/progenitor cells in a mammal, said method comprising:

providing differentiated T cells and/or stem/progenitor cells from said mammal;

performing a targeted insertion of a corrective CD40L cDNA donor at the CD40LG gene locus in said cells, downstream and operably linked to the endogenous CD40LG enhancer/promoter, to provide regulated control of the corrective CD40L cDNA donor, wherein said corrective CD40L cDNA donor comprises an optimized CD40L cDNA sequence and the 3' UTR of the CD40L gene, said donor comprising SEQ ID NO: 13, SEQ ID NO: 9, or SEQ ID NO: 11, and wherein said targeted insertion comprises transducing said cells with an AAV vector or a lentiviral vector comprising the corrective CD40L cDNA donor; and transfecting said cells in vitro, with a nucleic acid encoding a guide RNA (gRNA) and CRISPR/Cas endonuclease where said gRNA targets the CD40L 5' UTR; or a ribonucleoprotein (RNP) complex comprising a guide RNA complexed to a CRISPR/Cas endonuclease, where said gRNA targets the CD40L 5' UTR, and wherein said gRNA comprises the sequence set forth in SEQ ID NO: 12; and introducing said cells into said mammal;

wherein said method provides a corrected CD40LG gene expressed in a physiologically regulated manner.

2. The method of claim 1, wherein said corrective CD40L cDNA donor is flanked by homology arms.

3. The method of claim 1, wherein said corrective CD40L cDNA donor sequence is followed by the bGH polyA signal.

4. The method of claim 3, wherein said corrective CD40L cDNA donor sequence is flanked on its 5' end by a 5' homology arm that begins at the CRISPR/Cas cut site and extends at least 100 bp upstream; and/or following the bGH polyA signal it is flanked on its 3' end by a 3' homology arm that extends at least 200 bp, or at least 300 bp, or at least 350 bp, or at least 400 bp downstream of the CRISPR/Cas cut site.

5. The method of claim 1, wherein said cells comprise hematopoietic stem and progenitor cells (HSPC).

* * * * *

SEQUENCE LISTING

<160> NUMBER OF SEQ ID NOS: 53

<210> SEQ ID NO 1
<211> LENGTH: 113
<212> TYPE: DNA
<213> ORGANISM: Homo sapiens

<400> SEQUENCE: 1
ccactttgac agtcttctca tgctgcctct gccaccttct ctgccagaag ataccatttc 60
aactttaaca cagcatgatc gaaacataca accaaacttc tccccgatct gcg 113

<210> SEQ ID NO 2
<211> LENGTH: 113
<212> TYPE: DNA
<213> ORGANISM: Homo sapiens

<400> SEQUENCE: 2
ccactttgac agtcttctca tgctgcctct gccaccttct ctgccagaag ataccatttc 60
aactttaaca cagcatgatc gaaacataca accaaacttc tccccgatct gcg 113

<210> SEQ ID NO 3
<211> LENGTH: 177
<212> TYPE: DNA
<213> ORGANISM: Artificial
<220> FEATURE:
<223> OTHER INFORMATION: Fragment of CRISPR donor sequence

<400> SEQUENCE: 3
ctttacgtaa cgtttttgct gggagagaag actacgaagc acattttcca ggaagtgtgg 60
gctgcaacga ttgtgcgctc ttaactaatc ctgagtaagg tggccacttt gacagtcttc 120
tcatgctgcc tctgccacct tctctgccag aagataccat ttcaacttta acacagc 177

<210> SEQ ID NO 4
<211> LENGTH: 369
<212> TYPE: DNA
<213> ORGANISM: Artificial
<220> FEATURE:
<223> OTHER INFORMATION: Fragment of CRISPR donor sequence

<400> SEQUENCE: 4
cgccgccaca ggcctgccta tcagcatgaa gatctttatg tacctgctga ccgtgttcct 60
gatcacccag atgatcggca gcgccctgtt cgccgtgtac ctgcacagac ggctggacaa 120
gatcgaggac gagcggaacc tgcacgagga cttcgtgttc atgaagacca tccagcggtg 180
caacaccggc gagagaagcc tgagcctgct gaactgcgag gaaatcaaga gccagttcga 240
gggcttcgtg aaggacatca tgctgaacaa agaggaaact aagaaagaaa acagcttcga 300
gatgcagaag ggcgaccaga acccccagat tgccgcccac gtgatcagcg aggccagcag 360
caagaccac 369

```
<210> SEQ ID NO 5
<211> LENGTH: 501
<212> TYPE: DNA
<213> ORGANISM: Artificial
<220> FEATURE:
<223> OTHER INFORMATION: Fragment of CRISPR donor sequence

<400> SEQUENCE: 5

atctggtaag tcacacagca tctgagcggt agccacccaa ggggaaaggc tgggatgccg      60

gatcttgtgc cctgatagac ctaagactat cgaataggaa ttattttttta aaaagctcaa    120

ggaagcaaac acatcagtac tttcactttt cctcaaccct cacccccatc agtcagtcta     180

gctttctgtg ggagctgaga tttcaagtcg ggtgcacaca ctactttgaa cccactcaac     240

atctcagccg agaaaatggc acactgttgg tgggtactct ggcttagcca caagaatact     300

ggtactttca agttggtggc gcccactaca atgggagatc aaaacatacc gtgaaatgag     360

cacacagttt attttcatac ttccttgcct aattttagtc cttgctgggg gaggcagatc     420

aggtttgcaa cagttgtcag aatgtgaacc atgctctgct tcacctcacc acaaactttc     480

cctttctttg taacagtgtt a                                               501


<210> SEQ ID NO 6
<211> LENGTH: 372
<212> TYPE: DNA
<213> ORGANISM: Artificial
<220> FEATURE:
<223> OTHER INFORMATION: Fragment of CRISPR donor sequence

<400> SEQUENCE: 6

cagtgggccg agaagggcta ctacaccatg agcaacaacc tcgtgaccct ggaaaacggc      60

aagcagctga cagtgaagcg gcagggcctg tactacatct acgcccaagt gaccttctgc     120

agcaacagag aggccagctc ccaggccccc tttatcgcca gcctgtgcct gaagtccccc     180

ggcagattcg agagaatcct gctgagagcc gccaacaccc acagcagcgc caagccttgt     240

ggccagcagt ctatccacct gggcggcgtg ttcgaactgc agcctggcgc ctccgtgttc     300

gtgaacgtga ccgatcctag ccaggtgtcc cacggcaccg gcttcacaag cttcggactg     360

ctgaagctgt ga                                                         372


<210> SEQ ID NO 7
<211> LENGTH: 974
<212> TYPE: DNA
<213> ORGANISM: Homo sapiens

<400> SEQUENCE: 7

acagtgtcac cttgcaggct gtggtggagc tgacgctggg agtcttcata atacagcaca      60

gcggttaagc ccaccccctg ttaactgcct atttataacc ctaggatcct ccttatggag     120

aactatttat tatacactcc aaggcatgta gaactgtaat aagtgaatta caggtcacat     180

gaaaccaaaa cgggccctgc tccataagag cttatatatc tgaagcagca accccactga     240

tgcagacatc cagagagtcc tatgaaaaga caaggccatt atgcacaggt tgaattctga     300

gtaaacagca gataacttgc caagttcagt tttgtttctt tgcgtgcagt gtctttccat     360

ggataatgca tttgatttat cagtgaagat gcagaaggga aatggggagc ctcagctcac     420

attcagttat ggttgactct gggttcctat ggccttgttg gagggggcca ggctctagaa     480

cgtctaacac agtggagaac cgaaaccccc cccccccccg ccaccctctc ggacagttat     540

tcattctctt tcaatctctc tctctccatc tctctctttc agtctctctc tctcaacctc     600
```

tttcttccaa tctctctttc tcaatctctc tgtttccctt tgtcagtctc ttccctcccc 660
cagtctctct tctcaatccc cctttctaac acacacacac acacacacac acacacacac 720
acacacacac acacacacag agtcaggccg ttgctagtca gttctcttct ttccaccctg 780
tccctatctc taccactata gatgagggtg aggagtaggg agtgcagccc tgagcctgcc 840
cactcctcat tacgaaatga ctgtatttaa aggaaatcta ttgtatctac ctgcagtctc 900
cattgtttcc agagtgaact tgtaattatc ttgttattta ttttttgaat aataaagacc 960
tcttaacatt atcg 974

<210> SEQ ID NO 8
<211> LENGTH: 450
<212> TYPE: DNA
<213> ORGANISM: Artificial
<220> FEATURE:
<223> OTHER INFORMATION: Fragment of CRISPR donor sequence

<400> SEQUENCE: 8
tgcggccact ggactgccca tcagcatgaa aatttttatg tatttactta ctgtttttct 60
tatcacccag atgattgggt cagcactttt tgctgtgtat cttcatagaa ggttggacaa 120
ggtaagatga accacaagcc tttattaact aaatttgggg tccttactaa ttcataggtt 180
ggttctaccc aaatgatgga tgatggtaga aaccaaatag aagaatggtc ttgtggcata 240
atgtttgttg cctagtcaat gaagtctcat attcttgtct ctggttagga tcttgggatc 300
tggagtcaga ctgcctgggt tcaaatcttg gctctgccca taccatctct gttatcctgg 360
ggcaagtgcc tcagtttcca catctgagaa atggggatgg tattggtgtc catttcatag 420
attaagtgag tttagccttg taaaaagctt 450

<210> SEQ ID NO 9
<211> LENGTH: 2878
<212> TYPE: DNA
<213> ORGANISM: Artificial
<220> FEATURE:
<223> OTHER INFORMATION: Fragment of CRISPR donor sequence

<400> SEQUENCE: 9
ctttacgtaa cgtttttgct gggagagaag actacgaagc acattttcca ggaagtgtgg 60
gctgcaacga ttgtgcgctc ttaactaatc ctgagtaagg tggccacttt gacagtcttc 120
tcatgctgcc tctgccacct tctctgccag aagataccat ttcaacttta acacagcatg 180
atcgaaacat acaaccaaac ttctccccga tccgccgcca caggcctgcc tatcagcatg 240
aagatcttta tgtacctgct gaccgtgttc ctgatcaccc agatgatcgg cagcgccctg 300
ttcgccgtgt acctgcacag acggctggac aagatcgagg acgagcggaa cctgcacgag 360
gacttcgtgt tcatgaagac catccagcgg tgcaacaccg gcgagagaag cctgagcctg 420
ctgaactgcg aggaaatcaa gagccagttc gagggcttcg tgaaggacat catgctgaac 480
aaagaggaaa ctaagaaaga aaacagcttc gagatgcaga agggcgacca gaacccccag 540
attgccgccc acgtgatcag cgaggccagc agcaagacca catctggtaa gtcacacagc 600
atctgagcgg tagccaccca aggggaaagg ctgggatgcc ggatcttgtg ccctgataga 660
cctaagacta tcgaatagga attatttttt aaaaagctca aggaagcaaa cacatcagta 720
ctttcacttt tcctcaaccc tcacccccat cagtcagtct agctttctgt gggagctgag 780
atttcaagtc gggtgcacac actactttga acccactcaa catctcagcc gagaaaatgg 840
cacactgttg gtgggtactc tggcttagcc acaagaatac tggtactttc aagttggtgg 900

```
cgcccactac aatgggagat caaaacatac cgtgaaatga gcacacagtt tattttcata    960

cttccttgcc taattttagt ccttgctggg ggaggcagat caggtttgca acagttgtca   1020

gaatgtgaac catgctctgc ttcacctcac cacaaacttt ccctttcttt gtaacagtgt   1080

tacagtgggc cgagaagggc tactacacca tgagcaacaa cctcgtgacc ctggaaaacg   1140

gcaagcagct gacagtgaag cggcagggcc tgtactacat ctacgcccaa gtgaccttct   1200

gcagcaacag agaggccagc tcccaggccc cctttatcgc cagcctgtgc ctgaagtccc   1260

ccggcagatt cgagagaatc ctgctgagag ccgccaacac ccacagcagc gccaagcctt   1320

gtggccagca gtctatccac ctgggcggcg tgttcgaact gcagcctggc gcctccgtgt   1380

tcgtgaacgt gaccgatcct agccaggtgt cccacggcac cggcttcaca agcttcggac   1440

tgctgaagct gtgaacagtg tcaccttgca ggctgtggtg gagctgacgc tgggagtctt   1500

cataatacag cacagcggtt aagcccaccc cctgttaact gcctatttat aaccctagga   1560

tcctccttat ggagaactat ttattataca ctccaaggca tgtagaactg taataagtga   1620

attacaggtc acatgaaacc aaaacgggcc ctgctccata agagcttata tatctgaagc   1680

agcaacccca ctgatgcaga catccagaga gtcctatgaa aagacaaggc cattatgcac   1740

aggttgaatt ctgagtaaac agcagataac ttgccaagtt cagttttgtt tctttgcgtg   1800

cagtgtcttt ccatggataa tgcatttgat ttatcagtga agatgcagaa gggaaatggg   1860

gagcctcagc tcacattcag ttatggttga ctctgggttc ctatggcctt gttggagggg   1920

gccaggctct agaacgtcta acacagtgga gaaccgaaac cccccccccc cccgccaccc   1980

tctcggacag ttattcattc tctttcaatc tctctctctc catctctctc tttcagtctc   2040

tctctctcaa cctctttctt ccaatctctc tttctcaatc tctctgtttc cctttgtcag   2100

tctcttccct cccccagtct ctcttctcaa tcccccttc taacacacac acacacacac   2160

acacacacac acacacacac acacacacac acagagtcag gccgttgcta gtcagttctc   2220

ttctttccac cctgtcccta tctctaccac tatagatgag ggtgaggagt agggagtgca   2280

gccctgagcc tgcccactcc tcattacgaa atgactgtat ttaaaggaaa tctattgtat   2340

ctacctgcag tctccattgt ttccagagtg aacttgtaat tatcttgtta tttatttttt   2400

gaataataaa gacctcttaa cattatcgtg cggccactgg actgcccatc agcatgaaaa   2460

tttttatgta tttacttact gtttttctta tcacccagat gattgggtca gcactttttg   2520

ctgtgtatct tcatagaagg ttggacaagg taagatgaac cacaagcctt tattaactaa   2580

atttggggtc cttactaatt cataggttgg ttctacccaa atgatggatg atggtagaaa   2640

ccaaatagaa gaatggtctt gtggcataat gtttgttgcc tagtcaatga agtctcatat   2700

tcttgtctct ggttaggatc ttgggatctg gagtcagact gcctgggttc aaatcttggc   2760

tctgcccata ccatctctgt tatcctgggg caagtgcctc agtttccaca tctgagaaat   2820

ggggatggta ttggtgtcca tttcatagat taagtgagtt tagccttgta aaaagctt     2878
```

<210> SEQ ID NO 10
<211> LENGTH: 1058
<212> TYPE: DNA
<213> ORGANISM: Artificial
<220> FEATURE:
<223> OTHER INFORMATION: Fragment of CRISPR donor sequence

<400> SEQUENCE: 10

```
atctggtaag tcacacagca tctgagcggt agccacccaa ggggaaaggc tgggatgccg     60
```

```
aagtcatgtt acctaatggt taaactcctc ttttcccctg ggacccaatt tacaaaccta    120

cccctacagt aaagggcgag tcttaccagg tgggatcttg tgccctgata gacctaagac    180

tatcgaatag gaattatttt ttaaaaagct caaggaagca aacacatcag tactttcact    240

tttcctcaac cctcaccccc atcagtcagt ctagctttct gtgggagctg agatttcaag    300

tcgggtgcac acactacttt gaacccactc aacatctcag ccgagaaaat ggcacactgt    360

tggtgggtac tctggcttag ccacaagaat actggtactt tcaagttggt ggcgcccact    420

acaatgggag atcaaaacat accgtgaaat gagcacacag tttattttca tacttccttg    480

cctaatttta gtccttgctg gggaggcag atcaggtttg caacagcatg atcaggtagg    540

aagaaatggg gtcttttctc tgtgctgagg ctgagctagg tagactgaca actctctgac    600

tttgtaaaat tcaaggcaag caaggtattc atggtaatat tagcaaaaat ttggtccgag    660

taatttggta tgtataattt atgatgtcaa attttgaaat catttgtgcc ttcttaagtt    720

caaggcaaat tggctataag aactctaacg agagaaagaa actcactgtg atctcttact    780

ttatttaatc ttcacaagtc tctgaaatat gctccaatat gagccccgtg ttgcagatga    840

ggaactgaag ctcatggaga tttagagact tgcccaagct taaatagagc ctagattgga    900

acatggctct gtctgactct gaagcccatg gaaggggcct tgagaatcca tccctataca    960

aagccaatat ccaacattaa actatatttt ttgtcagaat gtgaaccatg ctctgcttca   1020

cctcaccaca aactttccct ttctttgtaa cagtgtta                           1058
```

<210> SEQ ID NO 11
<211> LENGTH: 3435
<212> TYPE: DNA
<213> ORGANISM: Artificial
<220> FEATURE:
<223> OTHER INFORMATION: Fragment of CRISPR donor sequence

<400> SEQUENCE: 11

```
ctttacgtaa cgtttttgct gggagagaag actacgaagc acattttcca ggaagtgtgg     60

gctgcaacga ttgtgcgctc ttaactaatc ctgagtaagg tggccacttt gacagtcttc    120

tcatgctgcc tctgccacct tctctgccag aagataccat ttcaacttta acacagcatg    180

atcgaaacat acaaccaaac ttctccccga tccgccgcca caggcctgcc tatcagcatg    240

aagatcttta tgtacctgct gaccgtgttc ctgatcaccc agatgatcgg cagcgccctg    300

ttcgccgtgt acctgcacag acggctggac aagatcgagg acgagcggaa cctgcacgag    360

gacttcgtgt tcatgaagac catccagcgg tgcaacaccg gcgagagaag cctgagcctg    420

ctgaactgcg aggaaatcaa gagccagttc gagggcttcg tgaaggacat catgctgaac    480

aaagaggaaa ctaagaaaga aaacagcttc gagatgcaga agggcgacca gaacccccag    540

attgccgccc acgtgatcag cgaggccagc agcaagacca catctggtaa gtcacacagc    600

atctgagcgg tagccaccca aggggaaagg ctgggatgcc gaagtcatgt tacctaatgg    660

ttaaactcct cttttcccct gggacccaat ttacaaacct acccctacag taaagggcga    720

gtcttaccag gtgggatctt gtgccctgat agacctaaga ctatcgaata ggaattattt    780

tttaaaaagc tcaaggaagc aaacacatca gtactttcac ttttcctcaa ccctcacccc    840

catcagtcag tctagctttc tgtgggagct gagatttcaa gtcgggtgca cacactactt    900

tgaacccact caacatctca gccgagaaaa tggcacactg ttggtgggta ctctggctta    960

gccacaagaa tactggtact ttcaagttgg tggcgcccac tacaatggga gatcaaaaca   1020

taccgtgaaa tgagcacaca gtttattttc atacttcctt gcctaatttt agtccttgct   1080
```

```
gggggaggca gatcaggttt gcaacagcat gatcaggtag gaagaaatgg ggtcttttct   1140
ctgtgctgag gctgagctag gtagactgac aactctctga ctttgtaaaa ttcaaggcaa   1200
gcaaggtatt catggtaata ttagcaaaaa tttggtccga gtaatttggt atgtataatt   1260
tatgatgtca aattttgaaa tcatttgtgc cttcttaagt tcaaggcaaa ttggctataa   1320
gaactctaac gagagaaaga aactcactgt gatctcttac tttatttaat cttcacaagt   1380
ctctgaaata tgctccaata tgagccccgt gttgcagatg aggaactgaa gctcatggag   1440
atttagagac ttgcccaagc ttaaatagag cctagattgg aacatggctc tgtctgactc   1500
tgaagcccat ggaaggggcc ttgagaatcc atccctatac aaagccaata tccaacatta   1560
aactatattt tttgtcagaa tgtgaaccat gctctgcttc acctcaccac aaactttccc   1620
tttctttgta acagtgttac agtgggccga gaagggctac tacaccatga gcaacaacct   1680
cgtgaccctg gaaaacggca agcagctgac agtgaagcgg cagggcctgt actacatcta   1740
cgcccaagtg accttctgca gcaacagaga ggccagctcc caggccccct ttatcgccag   1800
cctgtgcctg aagtcccccg gcagattcga gagaatcctg ctgagagccg ccaacaccca   1860
cagcagcgcc aagccttgtg gccagcagtc tatccacctg ggcggcgtgt tcgaactgca   1920
gcctggcgcc tccgtgttcg tgaacgtgac cgatcctagc caggtgtccc acggcaccgg   1980
cttcacaagc ttcggactgc tgaagctgtg aacagtgtca ccttgcaggc tgtggtggag   2040
ctgacgctgg gagtcttcat aatacagcac agcggttaag cccacccccct gttaactgcc   2100
tatttataac cctaggatcc tccttatgga gaactattta ttatacactc caaggcatgt   2160
agaactgtaa taagtgaatt acaggtcaca tgaaaccaaa acgggccctg ctccataaga   2220
gcttatatat ctgaagcagc aaccccactg atgcagacat ccagagagtc ctatgaaaag   2280
acaaggccat tatgcacagg ttgaattctg agtaaacagc agataacttg ccaagttcag   2340
ttttgtttct ttgcgtgcag tgtctttcca tggataatgc atttgattta tcagtgaaga   2400
tgcagaaggg aaatggggag cctcagctca cattcagtta tggttgactc tgggttccta   2460
tggccttgtt ggagggggcc aggctctaga acgtctaaca cagtggagaa ccgaaacccc   2520
cccccccccc gccaccctct cggacagtta ttcattctct ttcaatctct ctctctccat   2580
ctctctcttt cagtctctct ctctcaacct ctttcttcca atctctcttt ctcaatctct   2640
ctgtttccct ttgtcagtct cttccctccc ccagtctctc ttctcaatcc ccctttctaa   2700
cacacacaca cacacacaca cacacacaca cacacacaca cacacacaca gagtcaggcc   2760
gttgctagtc agttctcttc tttccaccct gtccctatct ctaccactat agatgagggt   2820
gaggagtagg gagtgcagcc ctgagcctgc ccactcctca ttacgaaatg actgtattta   2880
aaggaaatct attgtatcta cctgcagtct ccattgtttc cagagtgaac ttgtaattat   2940
cttgttattt attttttgaa taataaagac ctcttaacat tatcgtgcgg ccactggact   3000
gcccatcagc atgaaaattt ttatgtattt acttactgtt tttcttatca cccagatgat   3060
tgggtcagca ctttttgctg tgtatcttca tagaaggttg gacaaggtaa gatgaaccac   3120
aagcctttat taactaaatt tggggtcctt actaattcat aggttggttc tacccaaatg   3180
atggatgatg gtagaaacca aatagaagaa tggtcttgtg gcataatgtt tgttgcctag   3240
tcaatgaagt ctcatattct tgtctctggt taggatcttg ggatctggag tcagactgcc   3300
tgggttcaaa tcttggctct gcccatacca tctctgttat cctggggcaa gtgcctcagt   3360
ttccacatct gagaaatggg gatggtattg gtgtccattt catagattaa gtgagtttag   3420
```

```
ccttgtaaaa agctt                                                   3435


<210> SEQ ID NO 12
<211> LENGTH: 20
<212> TYPE: DNA
<213> ORGANISM: Artificial
<220> FEATURE:
<223> OTHER INFORMATION: CRISPR guide sequence

<400> SEQUENCE: 12

gtatcttctg gcagagaagg                                                20


<210> SEQ ID NO 13
<211> LENGTH: 2384
<212> TYPE: DNA
<213> ORGANISM: Artificial
<220> FEATURE:
<223> OTHER INFORMATION: Fragment of CRISPR donor sequence

<400> SEQUENCE: 13

ctttacgtaa cgtttttgct gggagagaag actacgaagc acattttcca ggaagtgtgg     60

gctgcaacga ttgtgcgctc ttaactaatc ctgagtaagg tggccacttt gacagtcttc    120

tcatgctgcc gctggaacct tctctgccag aagataccat ttcaacttta acacagcatg    180

atcgagacat acaaccagac cagccccaga agcgccgcca caggcctgcc tatcagcatg    240

aagatcttta tgtacctgct gaccgtgttc ctgatcaccc agatgatcgg cagcgccctg    300

ttcgccgtgt acctgcacag acggctggac aagatcgagg acgagcggaa cctgcacgag    360

gacttcgtgt tcatgaagac catccagcgg tgcaacaccg gcgagagaag cctgagcctg    420

ctgaactgcg aggaaatcaa gagccagttc gagggcttcg tgaaggacat catgctgaac    480

aaagaggaaa ctaagaaaga aaacagcttc gagatgcaga agggcgacca gaacccccag    540

attgccgccc acgtgatcag cgaggccagc agcaagacca cctccgtgct gcagtgggcc    600

gagaagggct actacaccat gagcaacaac ctcgtgaccc tggaaaacgg caagcagctg    660

acagtgaagc ggcagggcct gtactacatc tacgcccaag tgaccttctg cagcaacaga    720

gaggccagct cccaggcccc ctttatcgcc agcctgtgcc tgaagtcccc cggcagattc    780

gagagaatcc tgctgagagc cgccaacacc cacagcagcg ccaagccttg tggccagcag    840

tctatccacc tgggcggcgt gttcgaactg cagcctggcg cctccgtgtt cgtgaacgtg    900

accgatccta gccaggtgtc ccacggcacc ggcttcacaa gcttcggact gctgaagctg    960

acagtgtcac cttgcaggct gtggtggagc tgacgctggg agtcttcata atacagcaca   1020

gcggttaagc ccacccccctg ttaactgcct atttataacc ctaggatcct ccttatggag   1080

aactatttat tatacactcc aaggcatgta gaactgtaat aagtgaatta caggtcacat   1140

gaaaccaaaa cgggccctgc tccataagag cttatatatc tgaagcagca accccactga   1200

tgcagacatc cagagagtcc tatgaaaaga caaggccatt atgcacaggt tgaattctga   1260

gtaaacagca gataacttgc caagttcagt tttgtttctt tgcgtgcagt gtctttccat   1320

ggataatgca tttgatttat cagtgaagat gcagaaggga aatggggagc ctcagctcac   1380

attcagttat ggttgactct gggttcctat ggccttgttg gagggggcca ggctctagaa   1440

cgtctaacac agtggagaac cgaaaccccc cccccccccg ccaccctctc ggacagttat   1500

tcattctctt tcaatctctc tctctccatc tctctctttc agtctctctc tctcaacctc   1560

tttcttccaa tctctctttc tcaatctctc tgtttccctt tgtcagtctc ttccctcccc   1620

cagtctctct tctcaatccc cctttctaac acacacacac acacacacac acacacacac   1680
```

```
acacacacac acacacacag agtcaggccg ttgctagtca gttctcttct ttccaccctg   1740

tccctatctc taccactata gatgagggtg aggagtaggg agtgcagccc tgagcctgcc   1800

cactcctcat tacgaaatga ctgtatttaa aggaaatcta ttgtatctac ctgcagtctc   1860

cattgtttcc agagtgaact tgtaattatc ttgttattta tttttgaat aataaagacc    1920

tcttaacatt atcgtctctg ccagaagata ccatttcaac tttaacacag catgatcgaa   1980

acatacaacc aaacttctcc ccgatctgcg gccactggac tgcccatcag catgaaaatt   2040

tttatgtatt tacttactgt ttttcttatc acccagatga ttgggtcagc actttttgct   2100

gtgtatcttc atagaaggtt ggacaaggta agatgaacca caagccttta ttaactaaat   2160

ttggggtcct tactaattca taggttggtt ctacccaaat gatggatgat ggtagaaacc   2220

aaatagaaga atggtcttgt ggcataatgt ttgttgccta gtcaatgaag tctcatattc   2280

ttgtctctgg ttaggatctt gggatctgga gtcagactgc ctgggttcaa atcttggctc   2340

tgcccatacc atctctgtta tcctggggca agtgcctcag tttc                    2384
```

<210> SEQ ID NO 14

<400> SEQUENCE: 14

000

<210> SEQ ID NO 15
<211> LENGTH: 5
<212> TYPE: DNA
<213> ORGANISM: Streptococcus thermophilus
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 15 nggng 5

<210> SEQ ID NO 16
<211> LENGTH: 6
<212> TYPE: DNA
<213> ORGANISM: Streptococcus thermophilus
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: misc_feature
<222> LOCATION: (1)..(2)
<223> OTHER INFORMATION: n is a, c, g, or t

<400> SEQUENCE: 16 nnaaaw 6

<210> SEQ ID NO 17
<211> LENGTH: 6

<212> TYPE: DNA
<213> ORGANISM: Streptococcus thermophilus
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: misc_feature
<222> LOCATION: (1)..(2)
<223> OTHER INFORMATION: n is a, c, g, or t

<400> SEQUENCE: 17 nnagaa 6

<210> SEQ ID NO 18
<211> LENGTH: 7
<212> TYPE: DNA
<213> ORGANISM: Streptococcus thermophilus
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: misc_feature
<222> LOCATION: (1)..(3)
<223> OTHER INFORMATION: n is a, c, g, or t

<400> SEQUENCE: 18 nnngatt 7

<210> SEQ ID NO 19
<211> LENGTH: 7
<212> TYPE: DNA
<213> ORGANISM: Campylobacter jejuni
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 19 nnnnaca 7

<210> SEQ ID NO 20
<211> LENGTH: 8
<212> TYPE: DNA
<213> ORGANISM: Neisseria meningitidis
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 20 nnnngatt 8

<210> SEQ ID NO 21
<211> LENGTH: 8
<212> TYPE: DNA
<213> ORGANISM: Pasteurella multocida
<220> FEATURE:
<221> NAME/KEY: modified_base
<222> LOCATION: (2)..(4)
<223> OTHER INFORMATION: a, c, t, g, unknown or other
<220> FEATURE:

<221> NAME/KEY: misc_feature
<222> LOCATION: (2)..(4)
<223> OTHER INFORMATION: n is a, c, g, or t
<220> FEATURE:
<221> NAME/KEY: modified_base
<222> LOCATION: (6)..(7)
<223> OTHER INFORMATION: a, c, t, g, unknown or other
<220> FEATURE:
<221> NAME/KEY: misc_feature
<222> LOCATION: (6)..(7)
<223> OTHER INFORMATION: n is a, c, g, or t

<400> SEQUENCE: 21 gnnncnna 8

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(20)
<223> OTHER INFORMATION: a, c, t, g, unknown or other
<220> FEATURE:
<221> NAME/KEY: misc_feature
<222> LOCATION: (1)..(20)
<223> OTHER INFORMATION: This region may encompass 17-20 nucleotides

<400> SEQUENCE: 22
nnnnnnnnnn nnnnnnnnnn rg 22

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (2)..(21)
<223> OTHER INFORMATION: a, c, t, g, unknown or other
<220> FEATURE:
<221> NAME/KEY: misc_feature
<222> LOCATION: (2)..(21)
<223> OTHER INFORMATION: This region may encompass 17-20 nucleotides

<400> SEQUENCE: 23
gnnnnnnnnn nnnnnnnnnn nrg 23

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 24
aauuucuacu guuguagau 19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 25
aauuucugcu guugcagau 19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 26
aauuuccacu guuguggau 19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 27
aauuccuacu guuguaggu 19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 28
aauuucuacu auuguagau 19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 29
aauuucuacu gcuguagau 19

<210> SEQ ID NO 30
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 30
aauuucuacu uuguagau 18

<210> SEQ ID NO 31
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 31
aauuucuacu uguagau 17

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Pro Lys Lys Lys Arg Lys Val
1 5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Pro Lys Lys Lys Arg Arg Val
1 5

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Lys Arg Pro Ala Ala Thr Lys Lys Ala Gly Gln Ala Lys Lys Lys Lys
1 5 10 15

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Gly Arg Lys Lys Arg Arg Gln Arg Arg Arg Pro Pro Gln Pro Lys Lys
1 5 10 15

Lys Arg Lys Val
20

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Pro Leu Ser Ser Ile Phe Ser Arg Ile Gly Asp Pro Pro Lys Lys Lys
1 5 10 15

Arg Lys Val

<210> SEQ ID NO 37
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

```
Gly Ala Leu Phe Leu Gly Trp Leu Gly Ala Ala Gly Ser Thr Met Gly
1               5                   10                  15

Ala Pro Lys Lys Lys Arg Lys Val
            20
```

<210> SEQ ID NO 38
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

```
Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25
```

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

```
Lys Glu Thr Trp Trp Glu Thr Trp Trp Thr Glu Trp Ser Gln Pro Lys
1               5                   10                  15

Lys Lys Arg Lys Val
            20
```

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40

```
ctttacgtaa cgtttttgct gg                                              22
```

<210> SEQ ID NO 41
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41

```
agaagtttgg ttgtatgttt cgatcataaa tggtatcttc tggcagaga                 49
```

<210> SEQ ID NO 42

<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
ccagaagata ccatttcaac tttaac 26

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
gggcagagcc aagatttga 19

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
gccgccagtg tgctggaatt cctttacgta acgtttttgc tgg 43

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
cagcctgcaa ggtgacactg ttcagagttt gagtaagcca aagg 44

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
acagtgtcac cttgcaggc 19

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
gcagaattcg cccttgggca gagccaagat ttga 34

<210> SEQ ID NO 48
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48

gcaacgattg tgcgctctta                                                   20


<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49

acacagcaaa aagtgctgac c                                                 21


<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50

gcctctgcca ccttctctg                                                    19


<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51

caactttaac acagc                                                        15


<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: misc_feature
<222> LOCATION: (21)..(21)
<223> OTHER INFORMATION: n is a, c, g, or t

<400> SEQUENCE: 52

gtatcttctg gcagagaagg ngg                                               23


<210> SEQ ID NO 53
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
```

-continued

```
<400> SEQUENCE: 53

ccactttgac agtcttctca tgctgcctct gccaccttct ctgccagaag ataccatttc     60

aactttaaca cagcatgatc gaaacataca accaaacttc tccccgatct gcg           113
```